(12) United States Patent
Luo et al.

(10) Patent No.: US 11,384,400 B2
(45) Date of Patent: Jul. 12, 2022

(54) METHODS OF TREATING CANCERS CONTAINING FUSION GENES

(71) Applicant: UNIVERSITY OF PITTSBURGH—OF THE COMMONWEALTH SYSTEM OF HIGHER EDUCATION, Pittsburgh, PA (US)

(72) Inventors: Jianhua Luo, Wexford, PA (US); Zhanghui Chen, Huzhou (CN); Yanping Yu, Wexford, PA (US); George Michalopoulos, Pittsburgh, PA (US); Joel B. Nelson, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/427,185

(22) Filed: May 30, 2019

(65) Prior Publication Data
US 2020/0032346 A1 Jan. 30, 2020

Related U.S. Application Data

(63) Continuation of application No. PCT/US2017/066191, filed on Dec. 13, 2017.

(60) Provisional application No. 62/433,600, filed on Dec. 13, 2016.

(51) Int. Cl.
| | |
|---|---|
| *A61K 31/45* | (2006.01) |
| *C12Q 1/6886* | (2018.01) |
| *A61P 35/00* | (2006.01) |
| *A61K 31/4545* | (2006.01) |
| *A61K 31/5377* | (2006.01) |
| *A61N 7/00* | (2006.01) |
| *C12N 15/113* | (2010.01) |

(52) U.S. Cl.
CPC ........ *C12Q 1/6886* (2013.01); *A61K 31/4545* (2013.01); *A61K 31/5377* (2013.01); *A61N 7/00* (2013.01); *A61P 35/00* (2018.01); *C12N 15/1137* (2013.01); *C12N 2310/14* (2013.01); *C12Q 2600/106* (2013.01)

(58) Field of Classification Search
CPC .................................................. A61K 31/4545
See application file for complete search history.

(56) References Cited

U.S. PATENT DOCUMENTS

2016/0024588 A1  1/2016 Sigurdsson et al.

FOREIGN PATENT DOCUMENTS

| WO | WO 2009/019708 A2 | 2/2009 |
|---|---|---|
| WO | WO 2012/139134 A2 | 10/2012 |
| WO | WO 2014/151734 A1 | 9/2014 |
| WO | WO 2014/172046 A2 | 10/2014 |
| WO | WO 2015/103057 A1 | 7/2015 |
| WO | WO 2015/148494 A1 | 10/2015 |
| WO | WO 2015/149034 A2 | 10/2015 |
| WO | WO 2016/004165 A1 | 1/2016 |
| WO | WO 2016/011428 A1 | 1/2016 |
| WO | WO 2016/141169 A1 | 9/2016 |

OTHER PUBLICATIONS

Parker, et al. Chin J Cancer, 2013, vol. 32, Issue 11 pp. 594-603.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Alaei-Mahabadi et al., "Global analysis of somatic structural genomic alterations and their impact on gene expression in diverse human cancers," PNAS 113:48 13768-13773 (2016).
Mitelman et al., "The impact of translocations and gene fusions on cancer causation," Nature Reviews Cancer 233-245 (2007).
Zomerman et al., "Exogenous HGF Bypasses the Effects of ErbB Inhibition on Tumor Cell Viability in Medulloblastoma Cell Lines," PLOS One e0141381 (2015).
Ahn et al., "Fer Protein-Tyrosine Kinase Promotes Lung Adenocarcinoma Cell Invasion and Tumor Metastasis," Mol Cancer Res 11(8)952-963 (2013).
Chen et al., "MAN2A1-FER fusion gene is expressed by human liver and other tumor types and has oncogenic activity in mice," Gastroenterology 153:1120-1132 (2017).
Chen et al., "The DNA Replication Licensing Factor Miniature Chromosome Maintenance 7 Is Essential for RNA Splicing of Epidermal Growth Factor Receptor, c-Met, and Platelet-derived Growth Factor Receptor," The Journal of Biological Chemistry 290(3):1404-1411 (2015).
Dziadziuszko et al., "Epidermal growth factor receptor (EGFR) inhibitors and derived treatments," Annals of Oncology 23(Suppl. 10):193-196 (2012).
Fan et al., "HGF-independent regulation of MET and GAB1 by nonreceptor tyrosine kinase FER potentiates metastasis in ovarian cancer," Genes Dev 30:1542-1557 (2016).
Ferguson, "A structure-based view of Epidermal Growth Factor Receptor regulation," Annu Rev Biophys 37:353-373 (2008).
Gala et al., "Molecular Pathways: HER3 targeted therapy," Clin Cancer Res 20(6):1410-1416 (2014).
Guo et al., "FER tyrosine kinase (FER) overexpression mediates resistance to quinacrine through EGF-dependent activation of NF-κB," PNAS 108(19):7968-7973 (2011).

(Continued)

*Primary Examiner* — Shawquia Jackson
(74) *Attorney, Agent, or Firm* — Baker Botts L.L.P.

(57) ABSTRACT

The present invention relates to methods of treating cancer patients carrying one or more specific fusion genes. It is based, at least in part, on the discovery that the protein encoded by the MAN2A1-FER fusion gene exhibits kinase activity and the use of tyrosine kinase inhibitors targeting MAN2A1-FER in a cancer other than prostate, for example hepatocellular cancer, led to dramatic improvement of survival of animals xenografted with the cancer.

21 Claims, 44 Drawing Sheets

Figure 1:
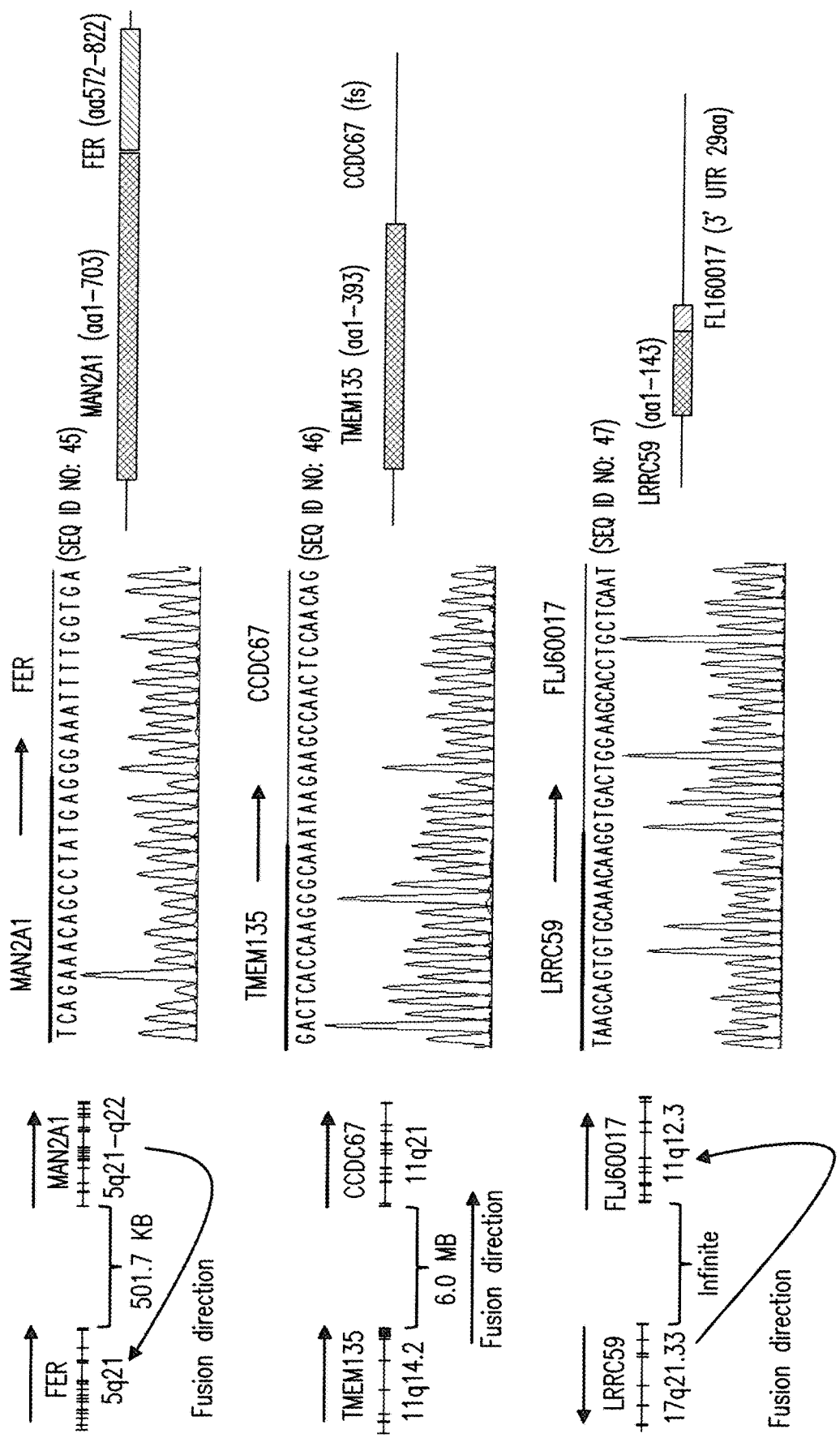
Figure 1:
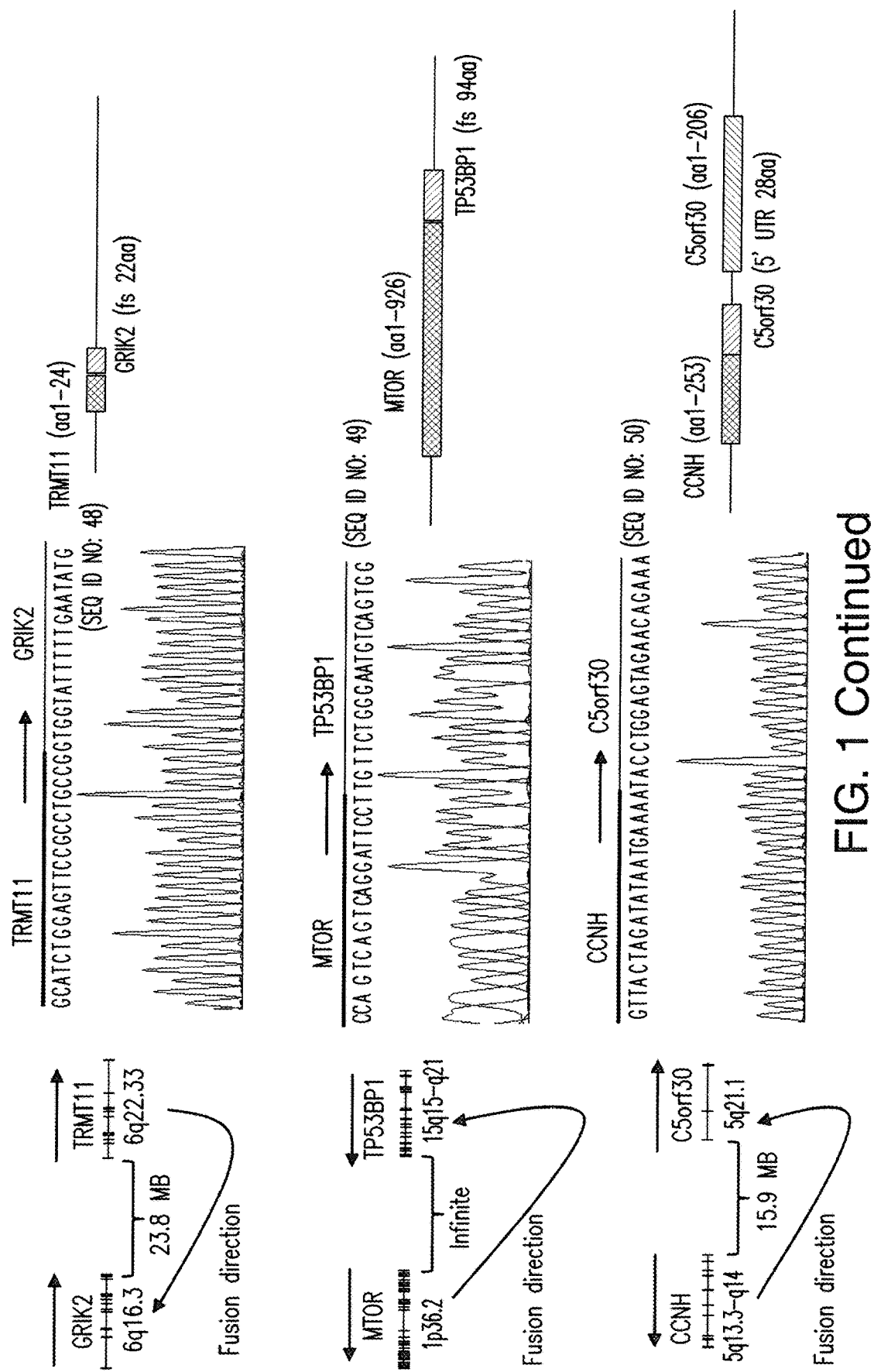
Figure 1:
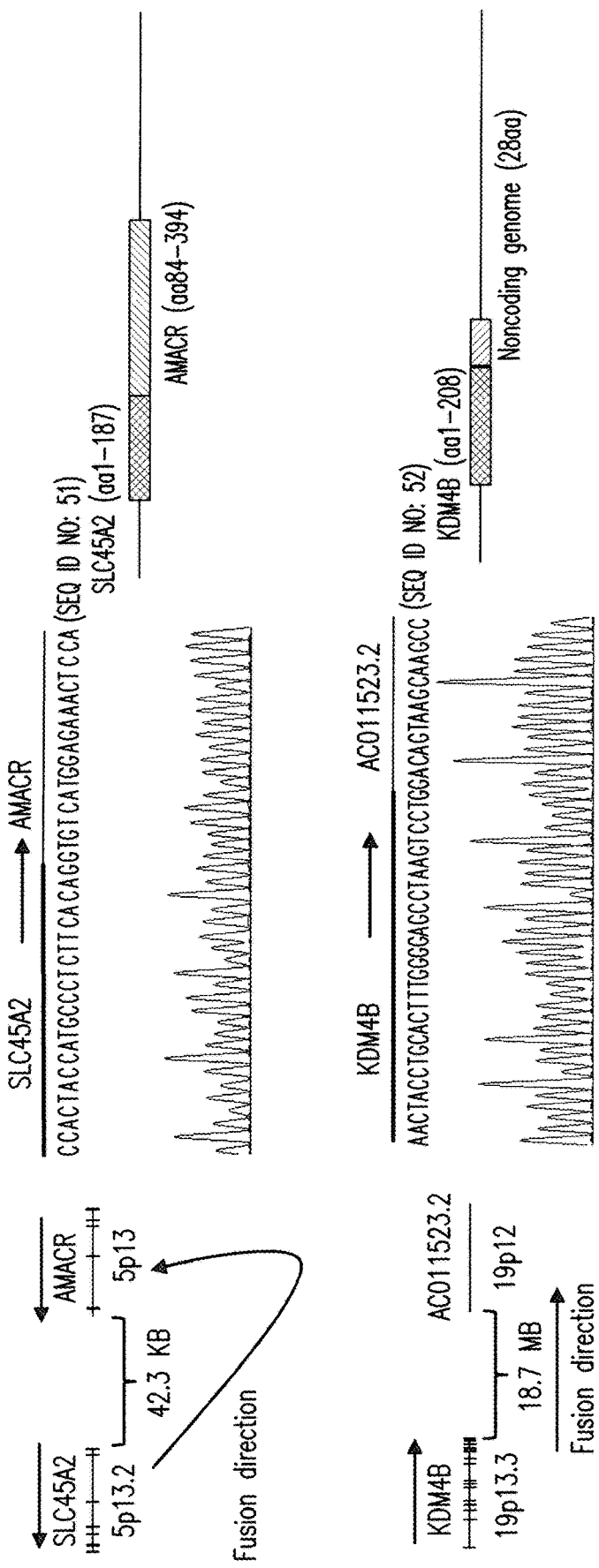

Specification includes a Sequence Listing.

(56) References Cited

OTHER PUBLICATIONS

Han et al., "Metallothionein 1 h tumour suppressor activity in prostate cancer is mediated by euchromatin methyltransferase 1," The Journal of Pathology 230(2):184-193 (2013).
Hao et al., "Isolation and Sequence Analysis of a Novel Human Tyrosine Kinase Gene," Molecular and Cellular Biology 9(4):1587-1593 (1989).
International Search Report dated Mar. 13, 2018 in International Application No. PCT/US2017/066191.
Ivanova et al., "FER kinase promotes breast cancer metastasis by regulating α6- and β1-integrin-dependent cell adhesion and anoikis resistance," Oncogene 32:5582-5592 (2013).
Jemal et al., "Global Cancer Statistics," CA Cancer J Clin 61:69-90 (2011).
Jing et al., "Expression of Myopodin Induces Suppression of Tumor Growth and Metastasis," The American Journal of Pathology 164(5):1799-1806 (2004).
Kawakami et al., "FER overexpression is associated with poor postoperative prognosis and cancer-cell survival in non-small cell lung cancer," International Journal of Clinical and Experimental Pathology 6(4):598-612 (2013).
Krolewski et al., "Identification and chromosomal mapping of new human tyrosine kinase gene," Oncogene 5:277-282 (1990).
Kwok et al., "FES Kinase Promotes Mast Cell Recruitment to Mammary Tumors via the Stem Cell Factor/KIT Receptor Signaling Axis," Mol Cancer Res 10(7):881-891 (2012).
Lee et al., "Epidermal Growth Factor Receptor Activation in Glioblastoma through Novel Missense Mutations in the Extracellular Domain," PLoS Med 3(12):e485 (2006).
Lee et al., "Small-molecule EGFR tyrosine kinase inhibitors for the treatment of cancer," Expert Opin Investig Drugs 23(10):1333-1348 (2014).
Li et al., "Identification of tyrosine-phosphorylated proteins associated with metastasis and functional analysis of FER in human hepatocellular carcinoma cells," BMC Cancer 9:366 (2009), 16 pages.
Liu et al., "Hydrodynamics-based transfection in animals by systemic administration of plasmid DNA," Gene Therapy 6:1258-1266 (1999).
Luo et al., "Discovery and Classification of Fusion Transcripts in Prostate Cancer and Normal Prostate Tissue," Am J Pathol 185:1834-1845 (2015).
Luo et al., "Genome-Wide Methylation Analysis of Prostate Tissues Reveals Global Methylation Patterns of Prostate Cancer," The American Journal of Pathology 182(6):2028-2036 (2013).
Luo et al., "Oncogenic driver mutations in lung cancer," Translational Respiratory Medicine 1:6 (2013), 8 pages.
Misago et al., "Molecular cloning and expression of cDNAs encoding human α-mannosidase II and a previously unrecognized α-mannosidase IIX isozyme," Proc Natl Acad Sci USA 92:11766-11770 (1995).
Miyata et al., "Feline sarcoma-related protein expression correlates with malignant aggressiveness and poor prognosis in renal cell carcinoma," Cancer Science 104:681-686 (2013).
Moremen et al., "Isolation, Characterization, and Expression of cDNAs Encoding Murine a-Mannosidase II, a Golgi Enzyme That Controls Conversion of High Mannose to Complex N-Glycans," J Cell Biol 115(6):1521-1534 (1991).
Nitulescu et al., "Akt inhibitors in cancer treatment: The long journey from drug discovery to clinical use (Review)," Int J Oncol. 48:869-885 (2016).
Ren et al., "Analysis of Integrin a7 Mutations in Prostate Cancer, Liver Cancer, Glioblastoma Multiforme, and Leiomyosarcoma," Journal of the National Cancer Institute 99:868-880 (2007).
Rocha et al., "The Fer tyrosine kinase acts as a downstream interleukin-6 effector of androgen receptor activation in prostate cancer," Molecular and Cellular Endocrinology 381:140-149 (2013).
Siegel et al., "Cancer Statistics, 2015" CA Cancer J Clin 65:5-29 (2015).
Siegel et al., "Cancer Statistics, 2016," CA Cancer J Clin 66:7-30 (2016).
Tao et al., "Modeling A Human HCC Subset in Mice Through Co-Expression Of Met And Point-Mutant β-Catenin," Hepatology 64(5):1587-1605 (2016).
Voisset et al., "The tyrosine kinase FES is an essential effector of KITD816V proliferation signal," Blood 110:2593-2599 (2007).
Wei et al., "High expression of FER tyrosine kinase predicts poor prognosis in clear cell renal cell carcinoma," Oncology Letters 5:473-478 (2013).
Wilson et al., "High-Throughput Screen Identifies Novel Inhibitors of Cancer Biomarker α-Methylacyl Coenzyme A Racemase (AMACR/P504S)," Mol. Cancer Ther. 10(5):825-838 (2011).
Yu et al., "CSR1 Suppresses Tumor Growth and Metastasis of Prostate Cancer," American Journal of Pathology168(2):597-607 (2006).
Yu et al., "Gene Expression Alterations in Prostate Cancer Predicting Tumor Aggression and Preceding Development of Malignancy," J Clin Oncol 22:2790-2799 (2004).
Yu et al., "Genome Abnormalities Precede Prostate Cancer and Predict Clinical Relapse," The American Journal of Pathology 180(6):2240-2248 (2012).
Yu et al., "Glutathione Peroxidase 3, Deleted or Methylated in Prostate Cancer, Suppresses Prostate Cancer Growth and Metastasis," Cancer Research 67(17):8043-8050 (2007).
Yu et al., "Linear Amplification of Gene-Specific Cdna Ends to Isolate Full-Length of a cDNA," Analytical Biochemistry 292:297-301 (2001).
Yu et al., "Novel Fusion Transcripts Associate with Progressive Prostate Cancer," The American Journal of Pathology 184(10):2840-2849 (2014).

\* cited by examiner

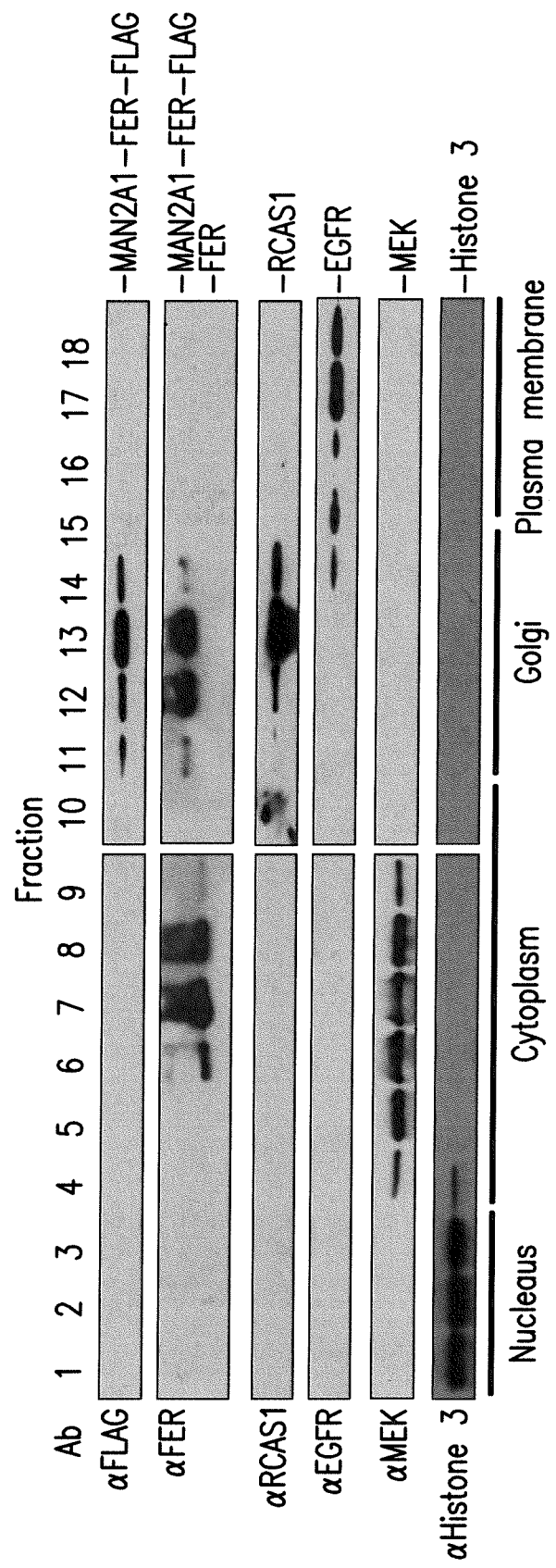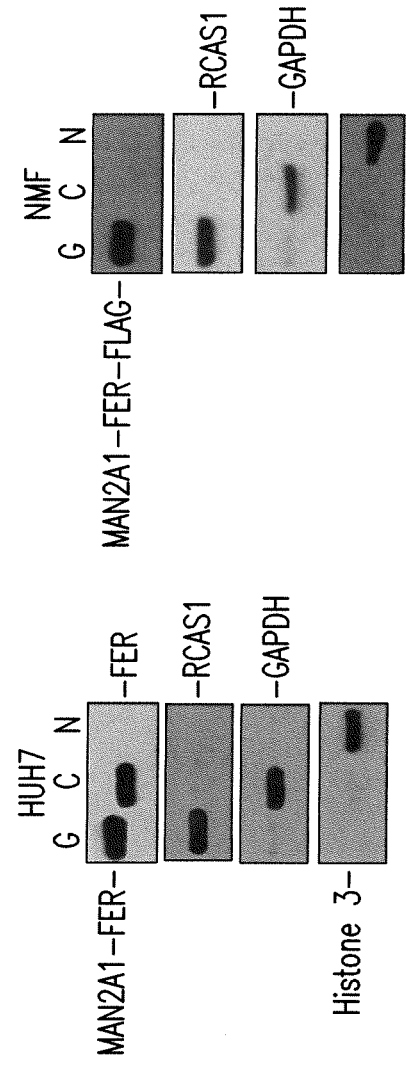
FIG. 14C
FIG. 14D

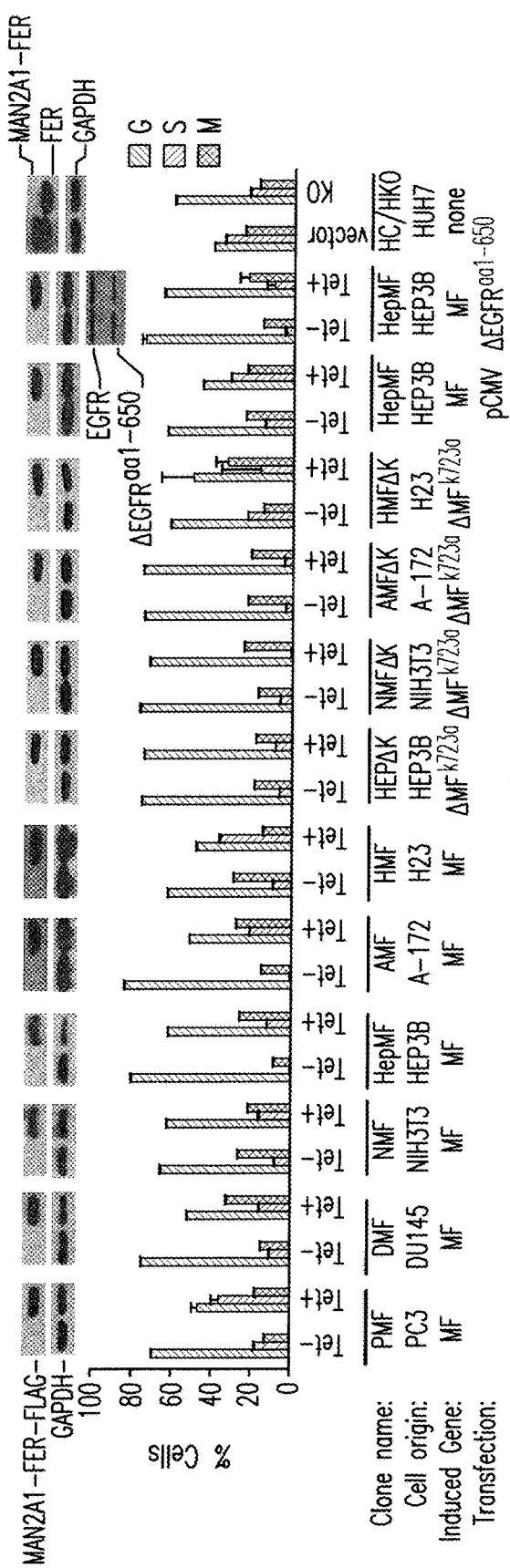
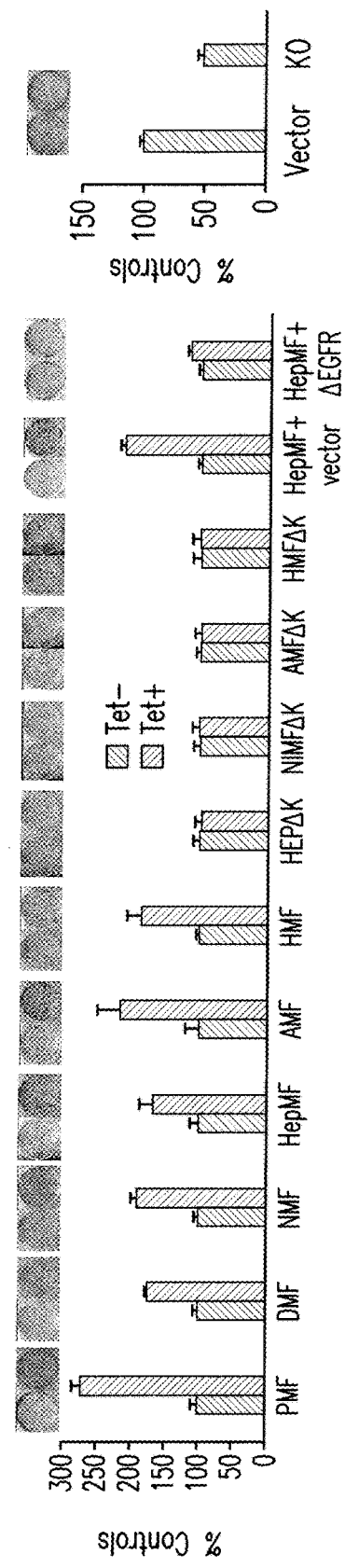
FIG. 17A
FIG. 17B

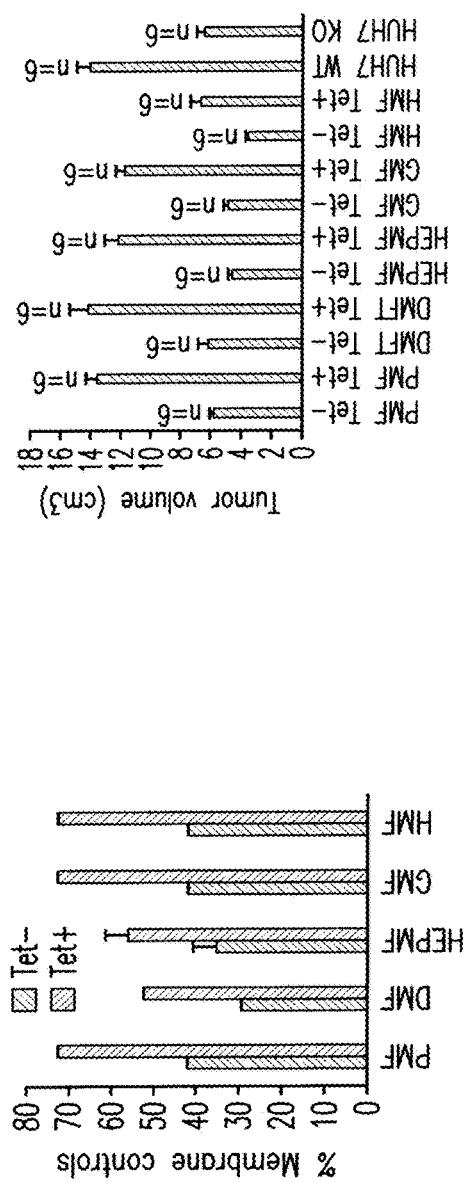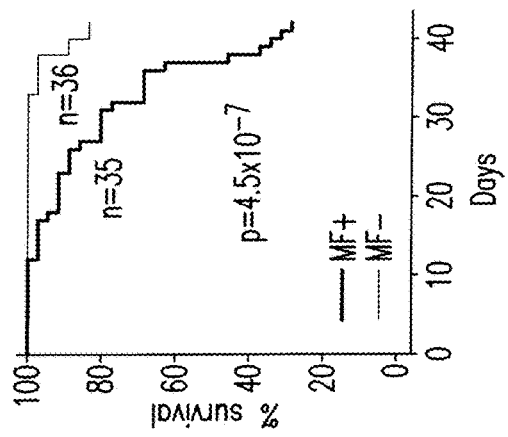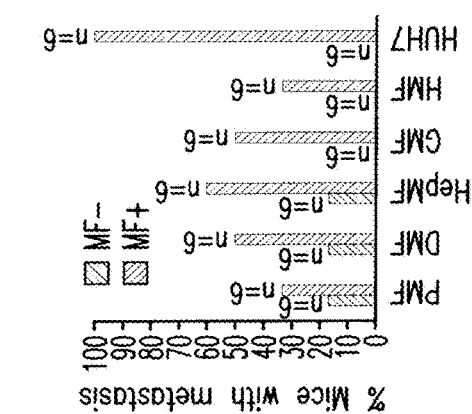

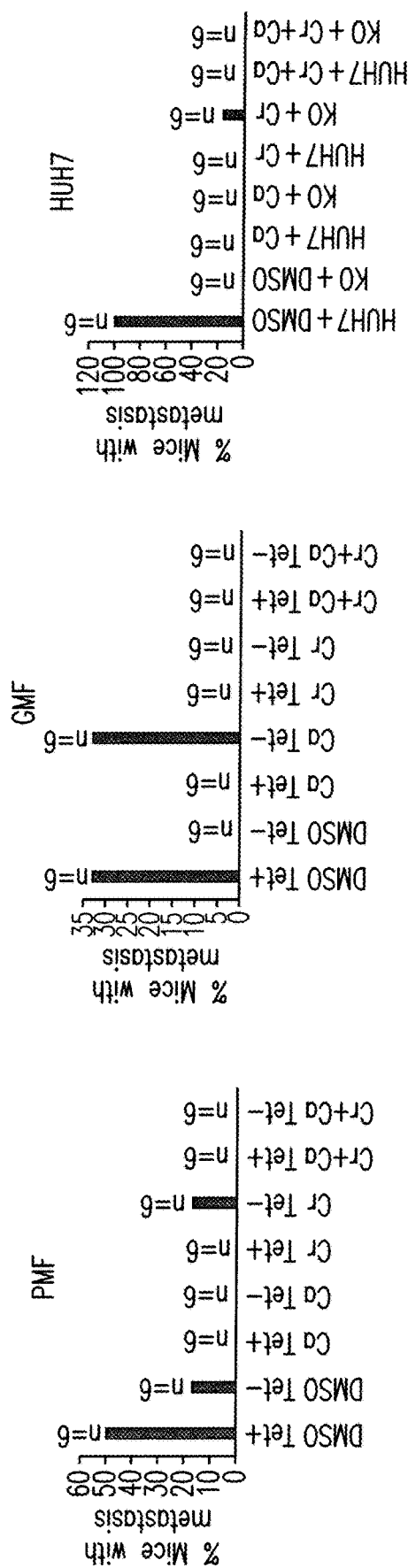
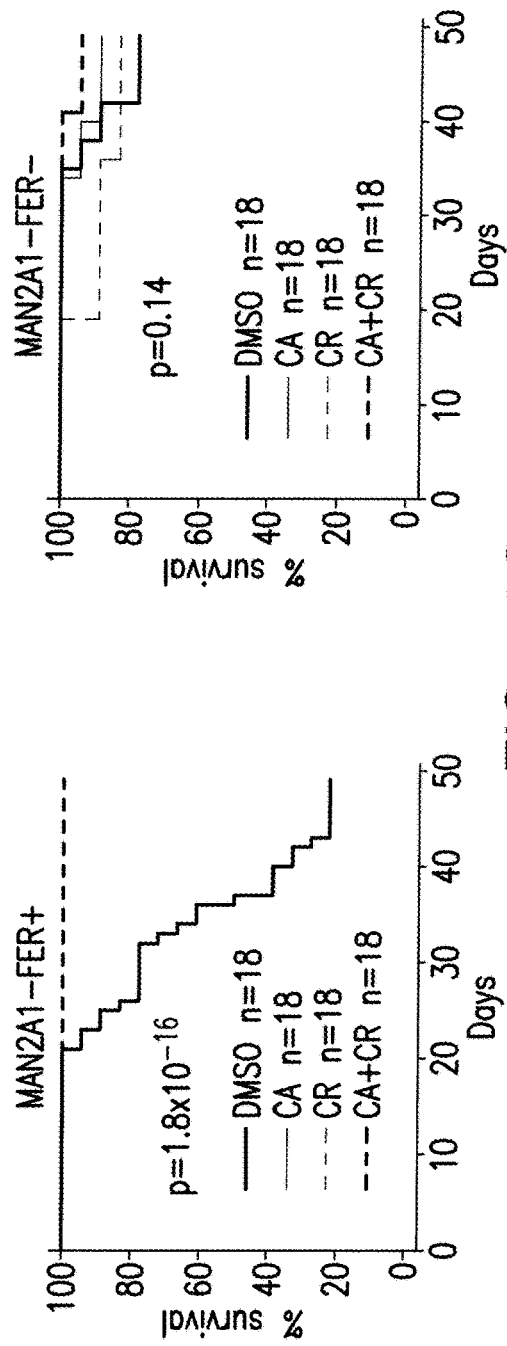
FIG. 19B
FIG. 19C

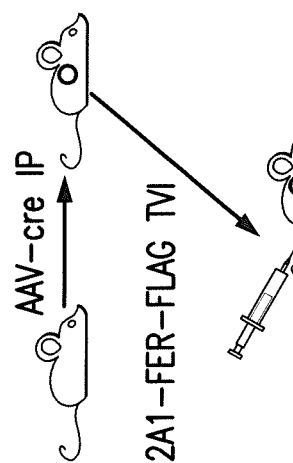
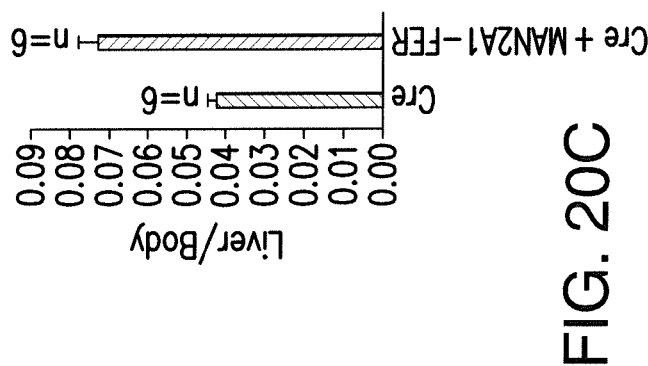
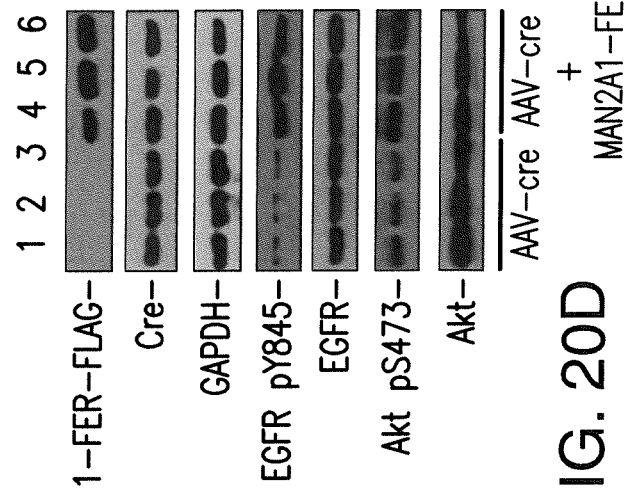

Figure 22:
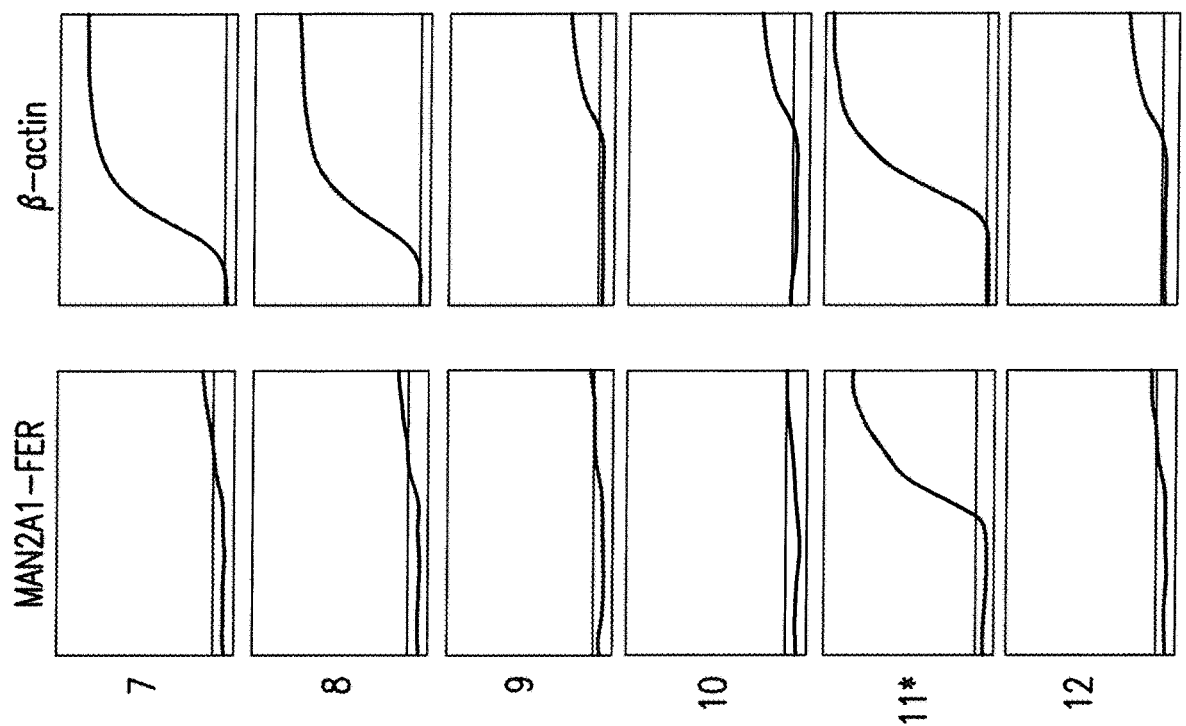
Figure 22:
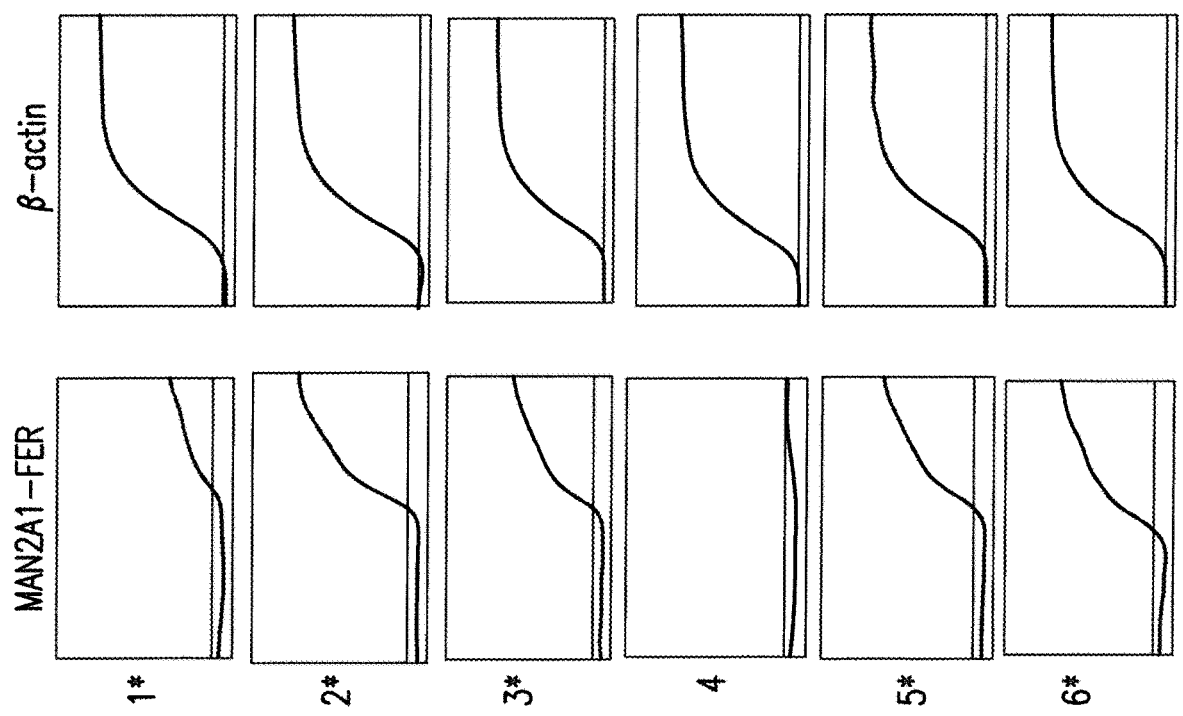
Figure 22:
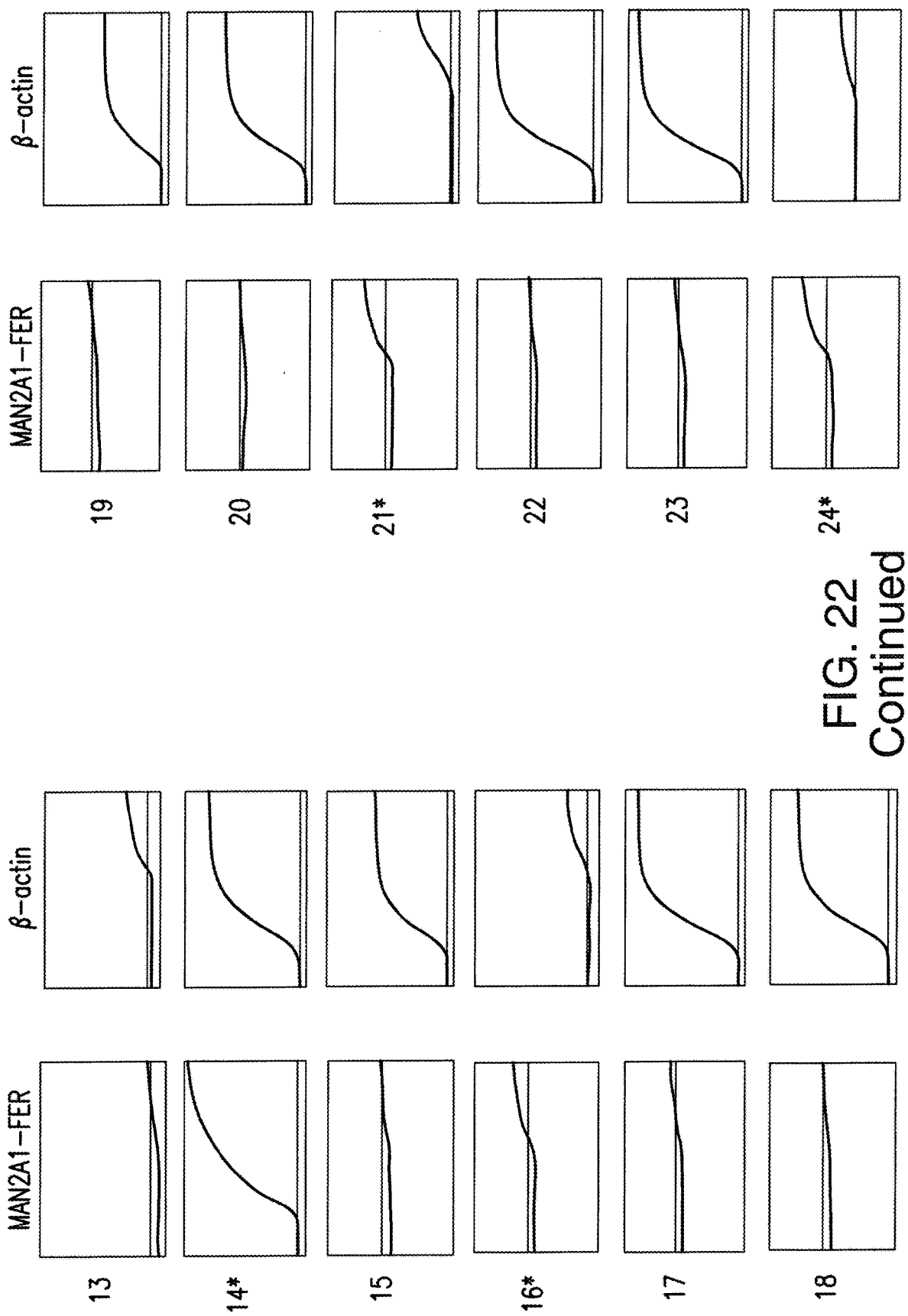
Figure 22:
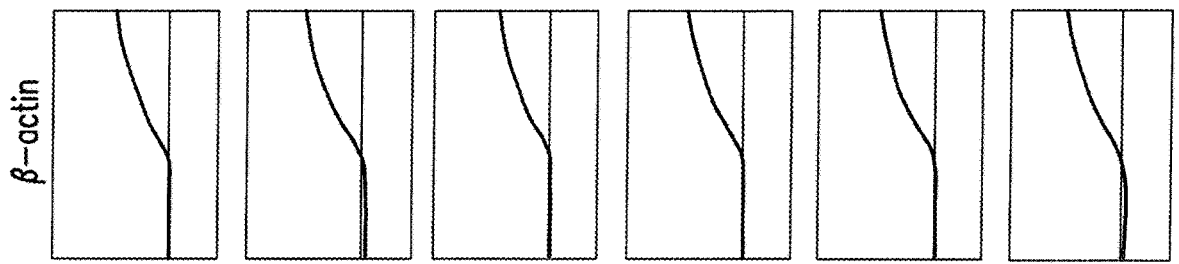
Figure 22:
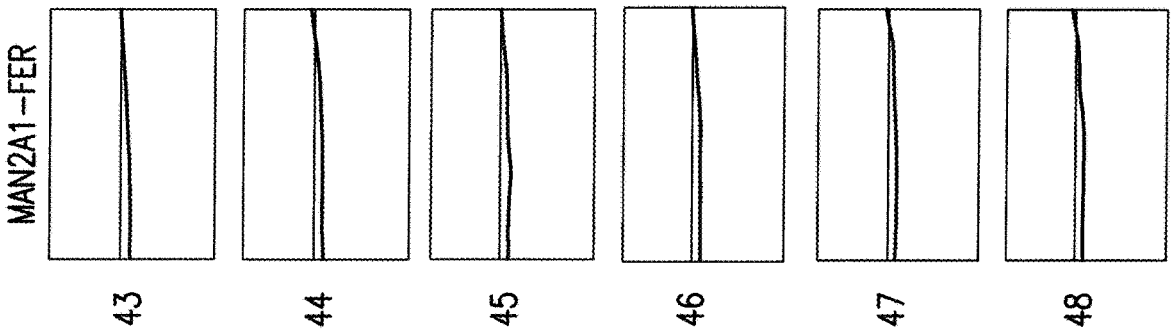
Figure 22:
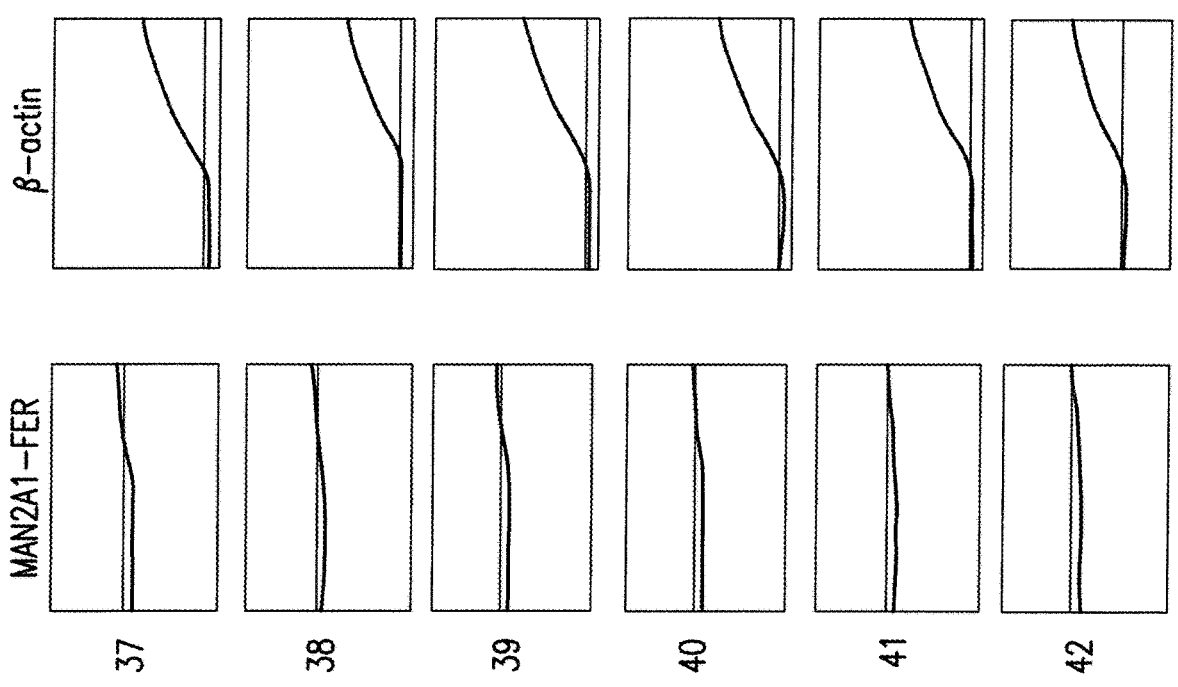
Figure 22:
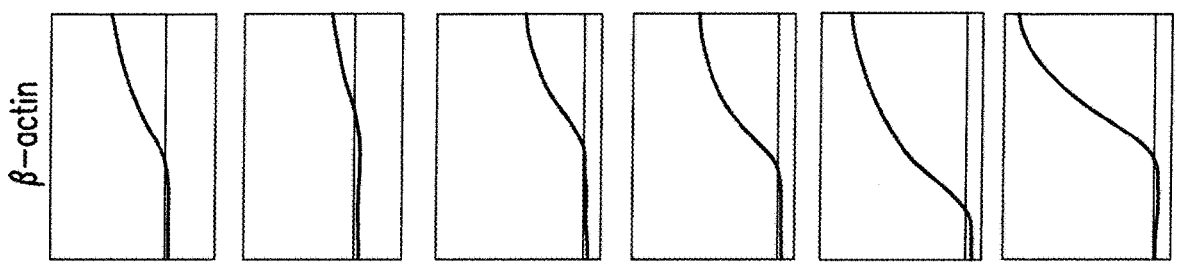
Figure 22:
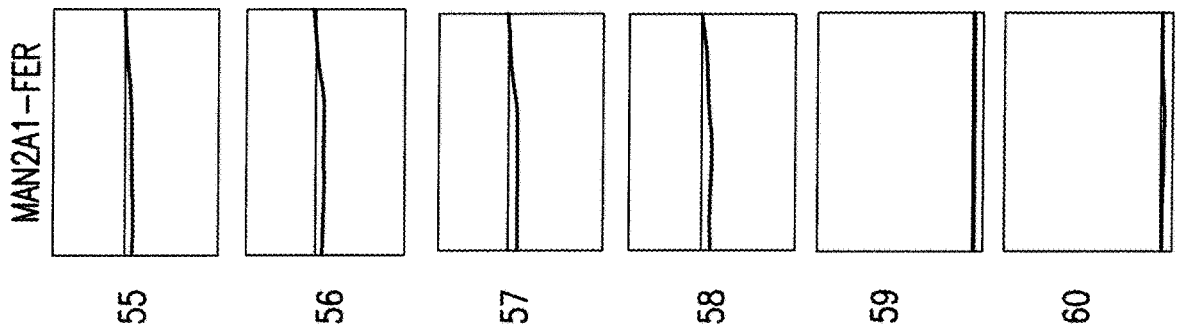
Figure 22:
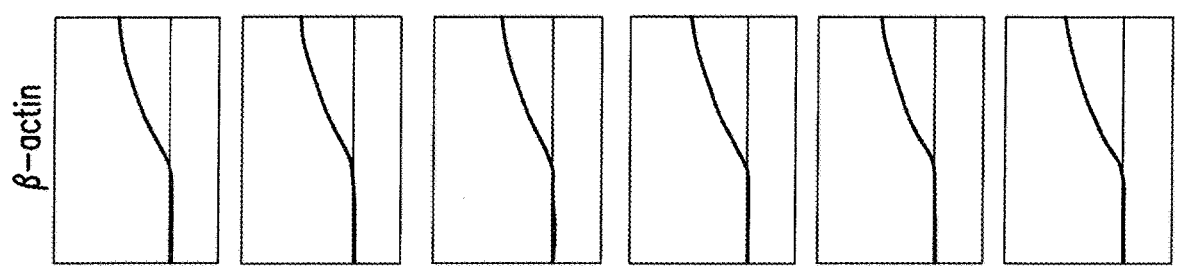
Figure 22:
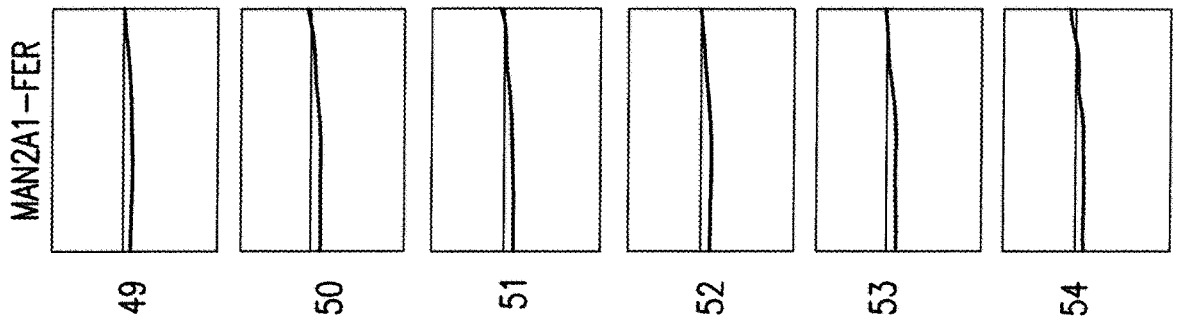
Figure 22:
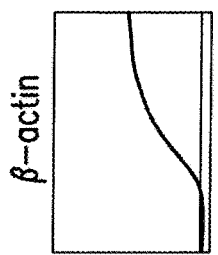
Figure 22:
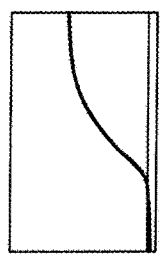
Figure 22:
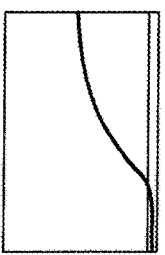
Figure 22:
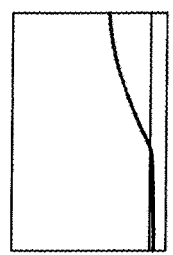
Figure 22:
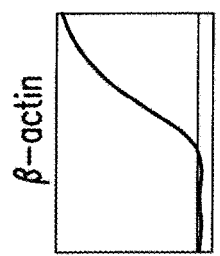
Figure 22:
Figure 22:
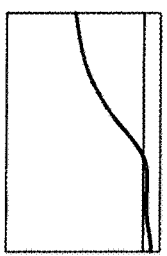
Figure 22:
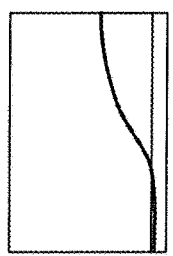
Figure 22:
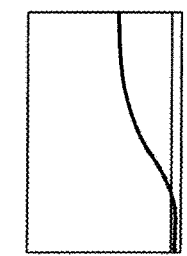
Figure 22:
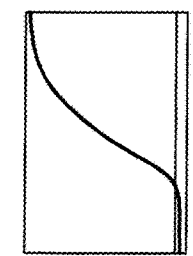
Figure 22:
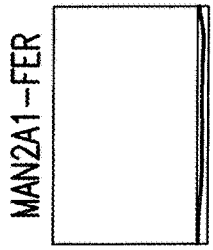
Figure 22:
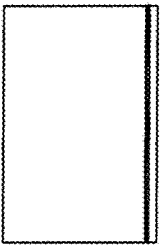
Figure 22:
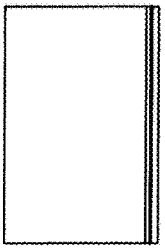
Figure 22:
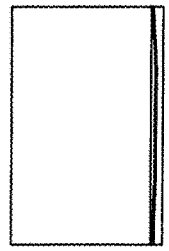
Figure 22:
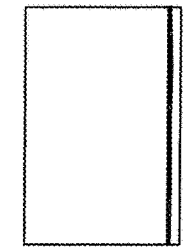
Figure 22:
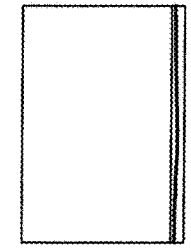

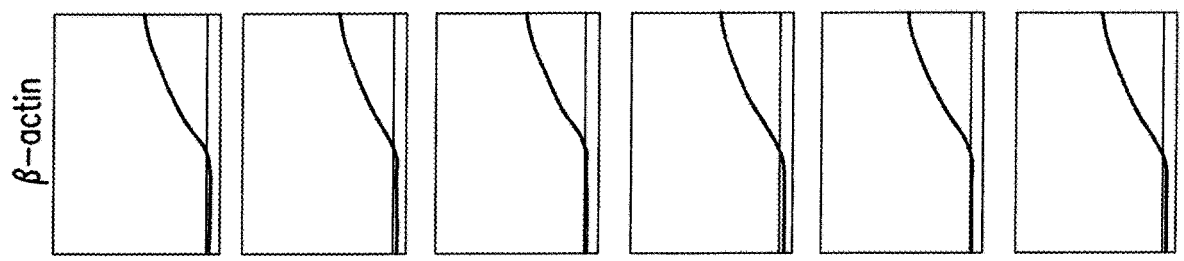
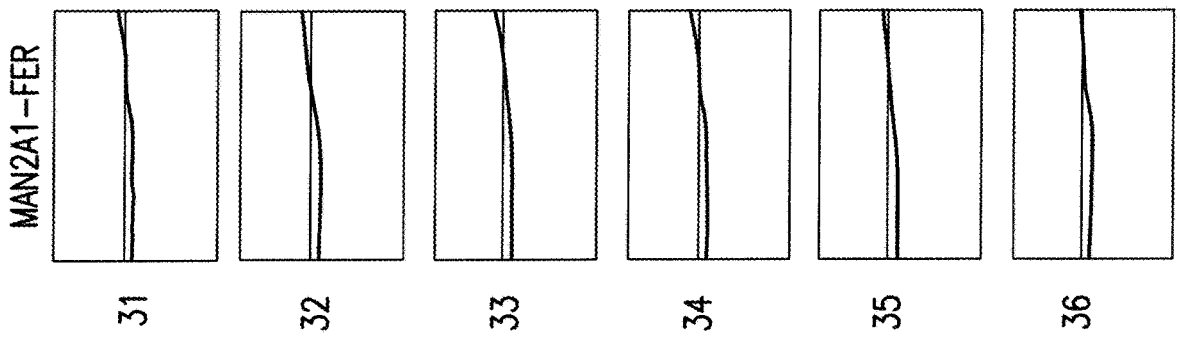
FIG. 22
Continued
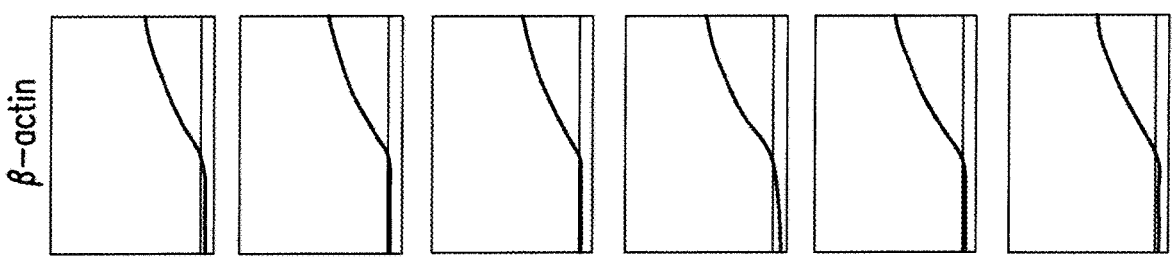
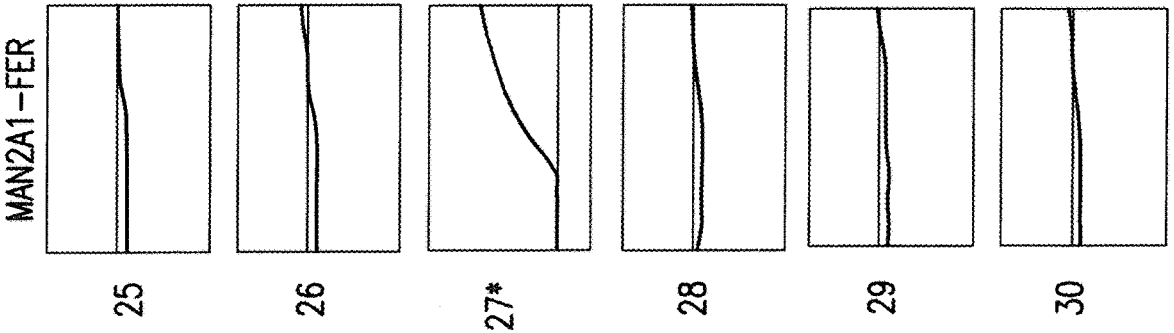

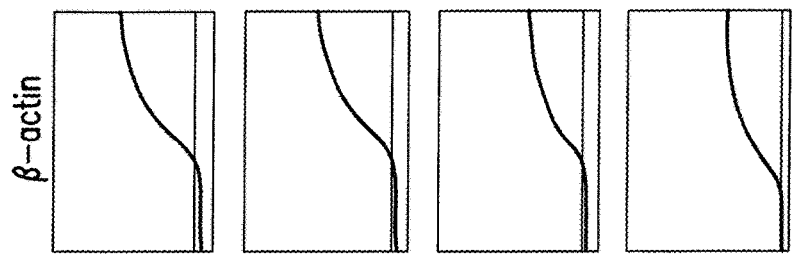
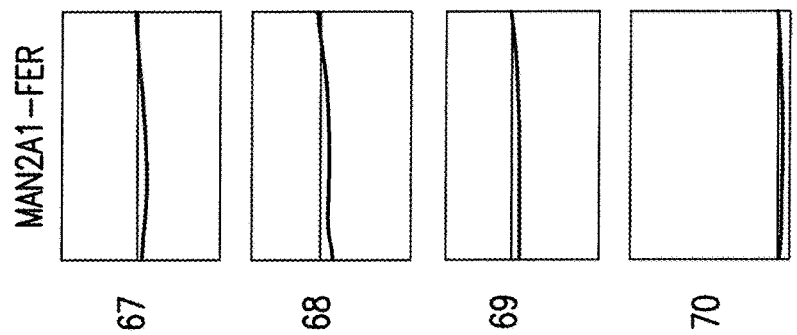
FIG. 22
Continued
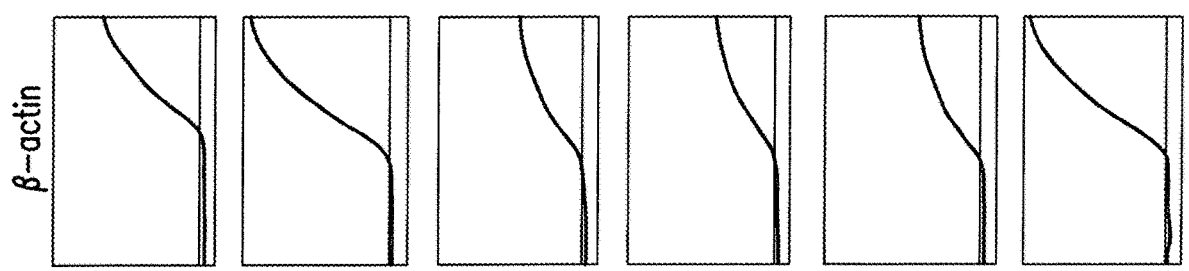
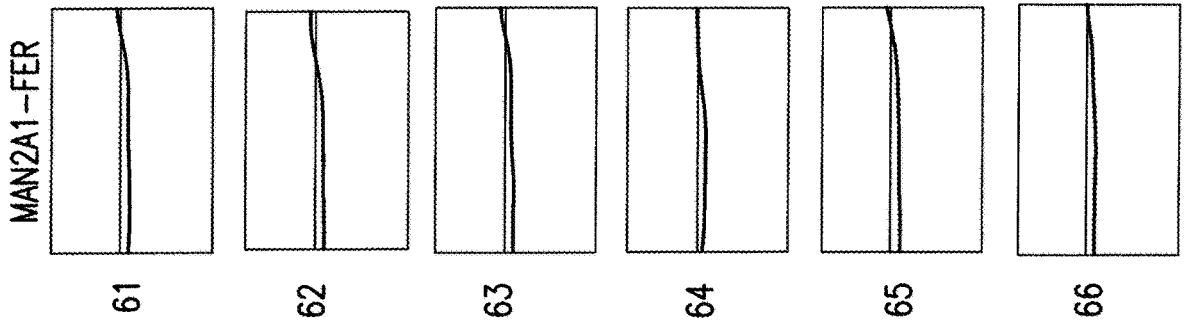

METHODS OF TREATING CANCERS CONTAINING FUSION GENES

PRIORITY INFORMATION

This application is a continuation of and claims priority to International Patent Application No. PCT/US2017/066191, filed Dec. 13, 2017, which claims priority to U.S. Provisional Patent Application No. 62/433,600, filed Dec. 13, 2016, all of which fare incorporated by reference herein in their entireties.

GRANT INFORMATION

This invention was made with government support under Grant No. RO1 CA098249 awarded by the National Institutes of Health and W81XWH-16-1-0364 awarded by the U.S. Army Medical Research & Materiel Command. The government has certain rights in the invention.

1. INTRODUCTION

The present invention relates to methods for treating patients carrying one or more specific fusion genes.

2. BACKGROUND OF THE INVENTION

In the U.S., prostate cancer is one of the most frequent malignancies observed in men. The mortality of prostate cancer reached 27,540 in 2014, the second most lethal cancer for men (Siegel et al. (2015) A Cancer Journal For Clinicians 65:5-29)). As disclosed in WO 2015/103057 and WO 2016/011428, a number of fusion genes, generated by chromosomal rearrangement, were identified in prostate cancers that have been shown to be recurrent and lethal. The expression of these fusion genes are widespread among aggressive prostate cancers but are absent in normal tissues. WO 2015/103057 discloses the treatment of prostate cancer cells that express the MAN2A1/FER fusion gene with a tyrosine inhibitor, resulting in the cell death of prostate cancer cells in vitro.

Cancers, in general, are among the leading causes of death in the U.S. The mortality rate of cancers reached 595,690 in 2015 in the U.S. alone, making it the second most lethal cause of death after cardiovascular diseases (Siegel et al. (2016) A Cancer Journal For Clinicians 66(1):7-30). Liver cancer is one of leading causes of cancer-related death for both men and women worldwide (Jemal et al. (2011) Global cancer statistics. CA Cancer J Clin 61:69-90). Even though significant progress has been made in the past several decades, much remains to be understood regarding the mechanisms of cancer development and progression. Treatment of cancers, particularly of those that become metastatic, remains problematic, and cures for cancer remain elusive. Therefore, there remains a need in the art for methods of treating cancer.

3. SUMMARY OF THE INVENTION

The present invention relates to methods of treating patients suffering from cancer or a pre-malignant or neoplastic condition carrying one or more specific fusion genes. It is based, at least in part, on the discovery that the protein encoded by the MAN2A1-FER fusion gene exhibits kinase activity and that the use of tyrosine kinase inhibitors targeting MAN2A1-FER in a cancer other than prostate cancer, for example hepatocellular cancer, led to dramatic improvement of survival of animals bearing cancer xenografts.

In various non-limiting embodiments, the present invention provides for methods and compositions for identifying fusion genes in a subject, e.g., a subject that has, or is suspected of having, cancer or a neoplastic or pre-malignant condition. In certain embodiments, the cancer is not prostate cancer. In certain embodiments, the cancer is not lung adenocarcinoma, glioblastoma multiforme or hepatocellular carcinoma. Such fusion genes include TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. Further, based on the presence of specific fusion genes, the present invention provides methods of treating a subject that carries one or more specific fusion genes, e.g., by administering a therapeutically effective amount of an agent specific for the fusion gene. In certain embodiments, the fusion gene is MAN2A1-FER.

In certain non-limiting embodiments, the present invention further provides kits for performing methods of treating a subject that carries a fusion gene. In certain embodiments, the subject does not have prostate cancer. In certain embodiments, the subject does not have lung adenocarcinoma, glioblastoma multiforme or hepatocellular carcinoma. In certain embodiments, a kit of the present invention can include nucleic acid primers for PCR analysis or nucleic acid probes for RNA in situ analysis to detect the presence of one or more fusion genes in a sample from the subject. In certain non-limiting embodiments, the one or more fusion genes can be selected from the group consisting of TRMT11-GRIK2, SLC45A2-AMACR, MTOR-TP53BP1, LRRC59-FLJ60017, TMEM135-CCDC67, PTEN-NOLC1, CCNH-C5orf30, TRMT11-GRIK2, SLC45A2-AMACR, KDM4B-AC011523.2, MAN2A1-FER, MTOR-TP53BP, ZMPSTE24-ZMYM4, CLTC-ETV1, ACPP-SEC13, DOCK7-OLR1, PCMTD1-SNTG11 and a combination thereof. In certain embodiments, the fusion gene is MAN2A1-FER. For example, and not by way of limitation, a kit of the present invention can include nucleic acid primers for PCR analysis or nucleic acid probes for RNA in situ analysis to detect the presence of the MAN2A1-FER fusion gene.

In certain embodiments, a kit of the present invention can include a pharmaceutical composition that includes one or more inhibitors that are specific for one or more fusion genes. For example, and not by way of limitation, a kit of the present invention can comprise a pharmaceutical composition that includes a FER inhibitor, e.g., crizotinib, and an EGFR inhibitor, e.g., canertinib, for use in treating a subject having a cancer that carries the MAN2A1-FER fusion gene.

4. BRIEF DESCRIPTION OF THE FIGURES

FIG. 1. Unique fusion gene events. Left panel: Miniature diagrams of genome of the fusion genes, the transcription directions, the distances between the joining genes and directions of the fusions. Middle panel: Representative sequencing chromograms of fusion genes. The joining gene sequences were indicated (SEQ ID NOs: 45-52). Right panel: Diagrams of translation products of fusion genes. Blue-driver gene translation product; Red-passenger gene translation product; Orange-novel translation products due to frameshift or translation products from a non-gene region.

Figure 2:
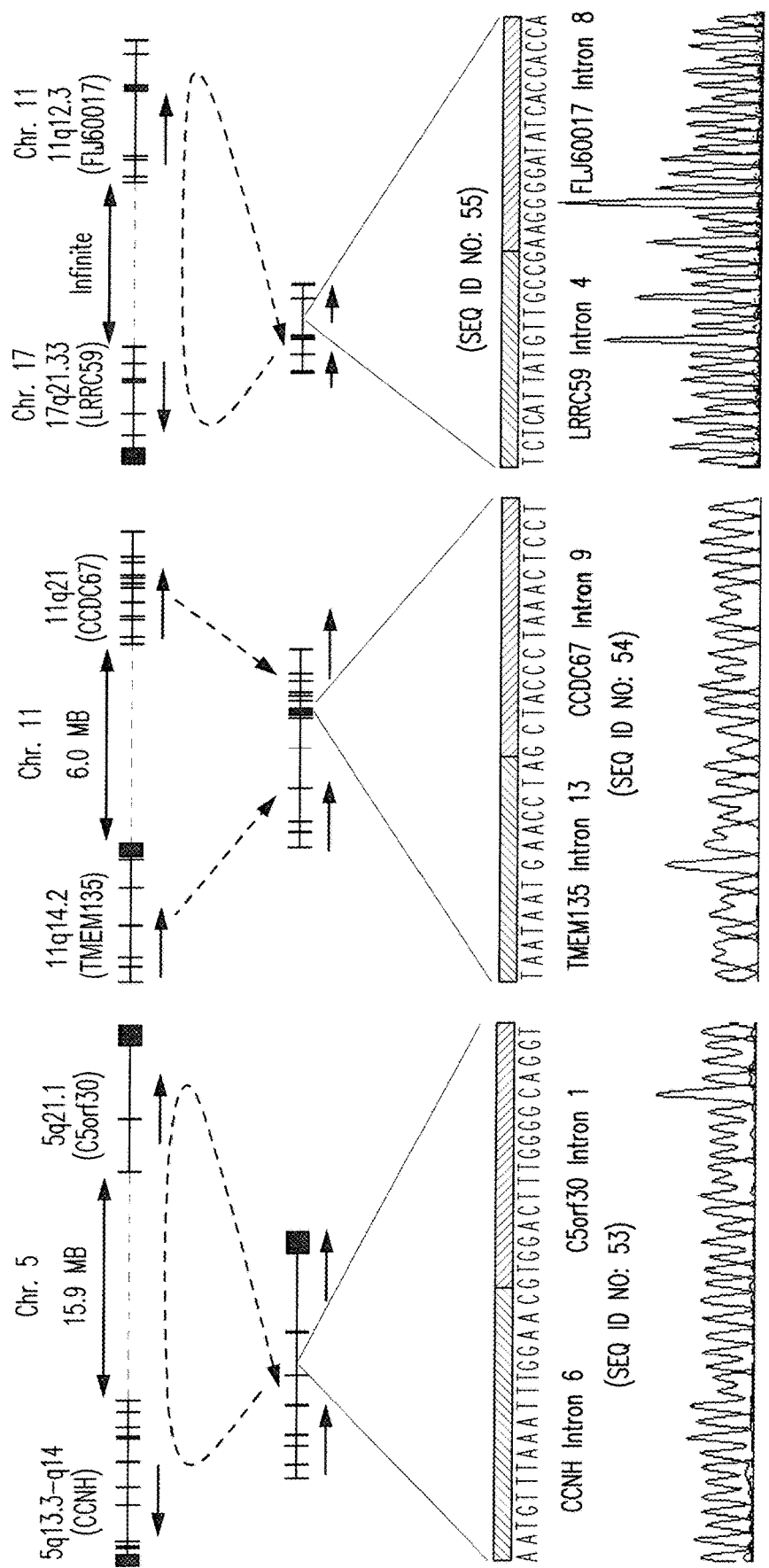

FIG. 2. Genome breakpoint analysis of fusion genes. Top panel: Miniature diagrams of genome of the fusion genes, the transcription directions, the distances between the joining genes and directions of the chromosome joining. Middle panel: Miniature of fusion genome and transcription direction. Bottom: Representative sequencing chromograms encompassing the joining breakpoint of chromosomes (SEQ ID NOs: 53-55).

Figure 3A:
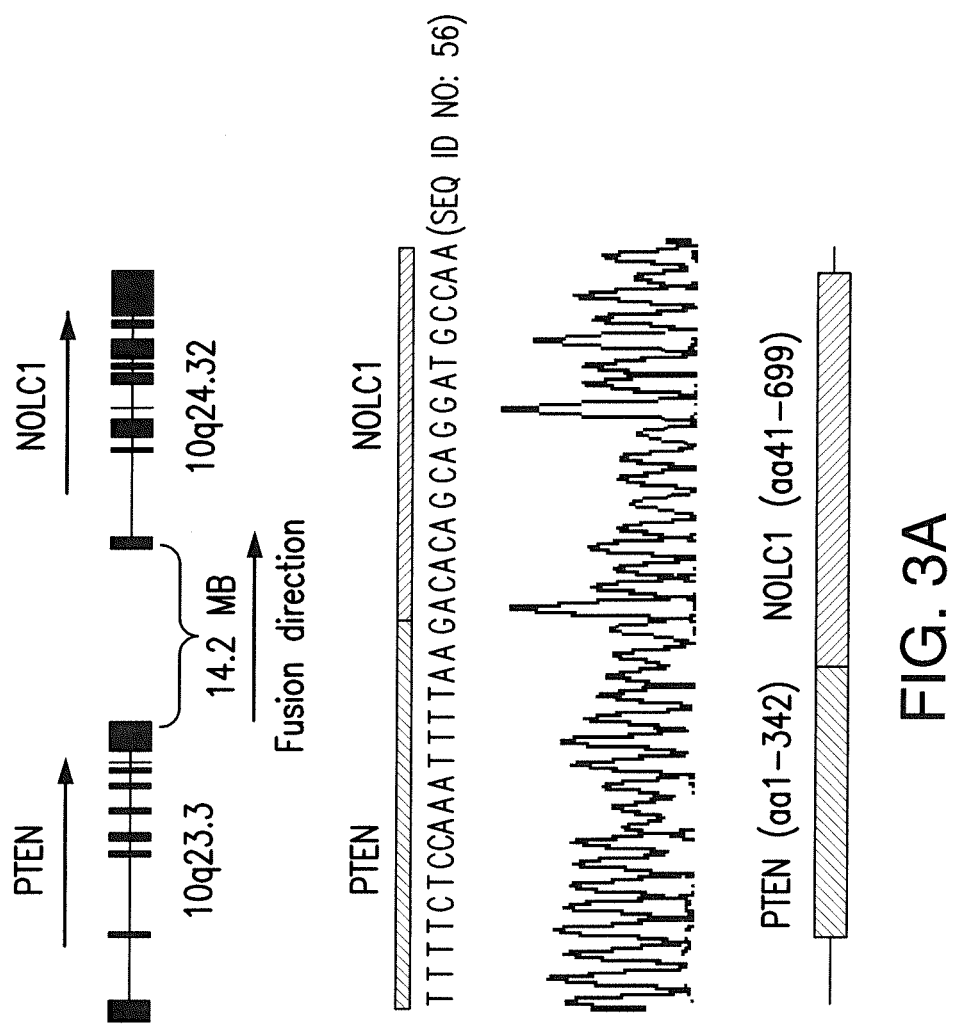
Figure 3B:
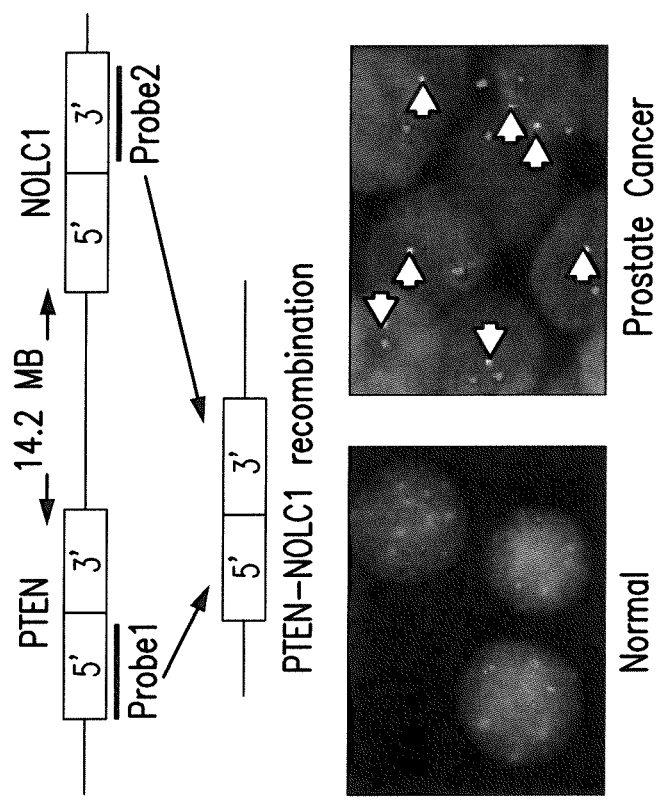

FIG. 3A-B. PTEN-NOLC1 fusion gene in prostate cancer. (A) PTEN-NOLC1 fusion transcript. Top panel: Miniature diagrams of genome of the PTEN and NOLC1 genes, the transcription direction, the distance between the joining genes and direction of the fusion. Middle panel: Representative sequencing chromogram of PTEN-NOLC1 transcript. The joining gene sequences were indicated (SEQ ID NO: 56). Lower panel: Diagram of translation product of fusion transcript. Blue-head gene translation product; Red-tail gene translation product. (B) Schematic diagram of PTEN and NOLC1 genome recombination and FISH probe positions.

Figure 4:
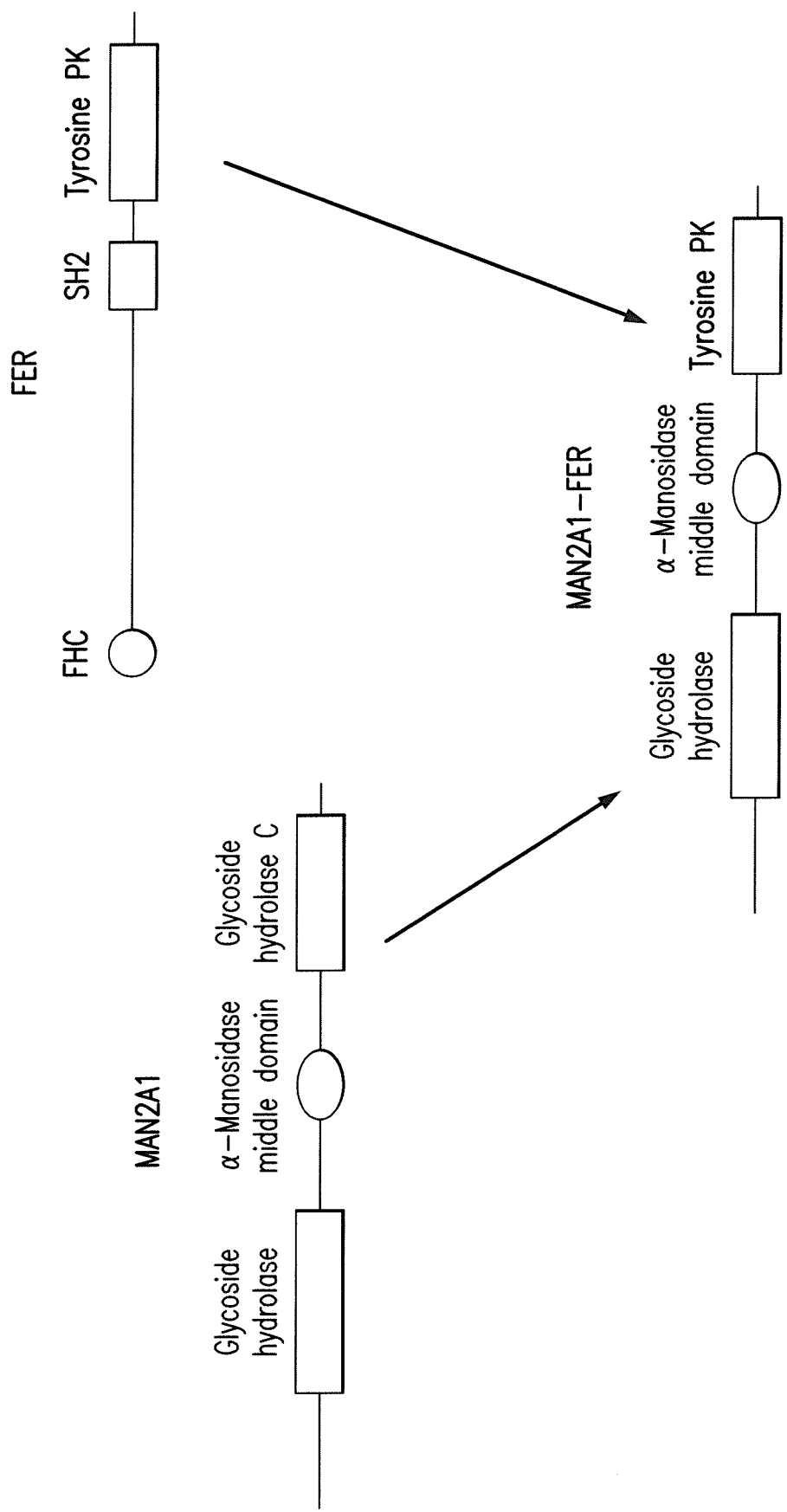

FIG. 4. Motif analysis of MAN2A1-FER. Diagram of functional domains of MAN2A1, FER and MAN2A1-FER fusion proteins. In the fusion gene MAN2A1-FER, the N-terminus of FER suffers a loss of SH2 and FHC domains. These domains were replaced with the glycoside hydrolase and α-mannosidase middle domain from MAN2A1.

Figure 5:
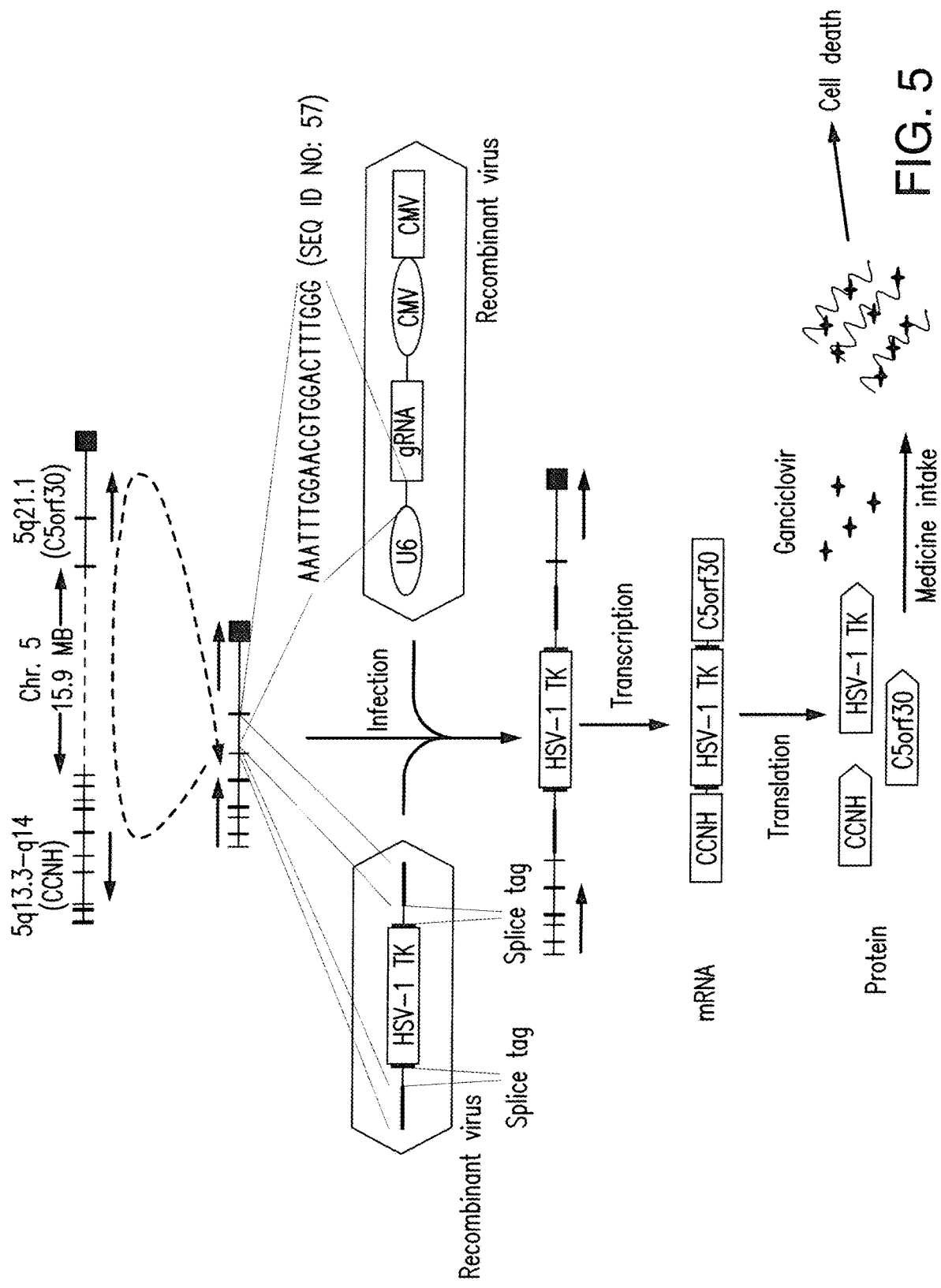

FIG. 5. Schematic diagram of Genome editing targeting at a fusion gene breakpoint in prostate cancer cells positive for CCNH-C5orf30. Genome recombination in prostate cancer case 3T produced a breakpoint in chromosome 5 that connect intron 6 of CCNH with intron 1 of C5orf30. A guide RNA (gRNA) of 23 bp including protospacer adjacent motif (PAM) sequence is designed specific for the breakpoint region. The DNA sequence corresponding to this target sequence is artificially ligated into vector containing the remainder of gRNA and Cas9. This sequence is recombined and packaged into recombinant virus (Adenovirus or lentivirus). A promoterless Herpes Simplex Virus Type 1 (HSV-1) thymidine kinase is constructed into a shuttle vector for adenovirus along with splice tag sequence from intron/exon juncture of CCNH exon 7. A 500 bp sequence surrounding the CCNH-C5orf30 breakpoint from each side is also ligated into the shuttle vector in order to produce efficient homologous recombination to complete the donor DNA construction. The vector is recombined and packaged into AdEasy to generate recombinant viruses. These viruses can be administered to patients or animals that have cancer positive for CCNH-C5orf30 fusion transcript. This leads to insertion of donor DNA into the target site (fusion breakpoint). Since HSV-1 TK in recombinant virus is promoterless, no transcription will occur if HSV-1 TK cDNA does not integrate into a transcription active genome. However, transcription of HSV-1 TK is active if HSV-1 TK is integrated into the target site of CCNH-C5orf30 in the patient, and when ganciclovir or its oral homologue valganciclovir is administered to the patient, the homologue is readily converted to triphosphate guanine analogue by HSV-1 TK and incorporated into the genomes of cancer cells. This leads to stoppage of DNA elongation in cells that are positive for CCNH-C5orf30.

Figure 6:
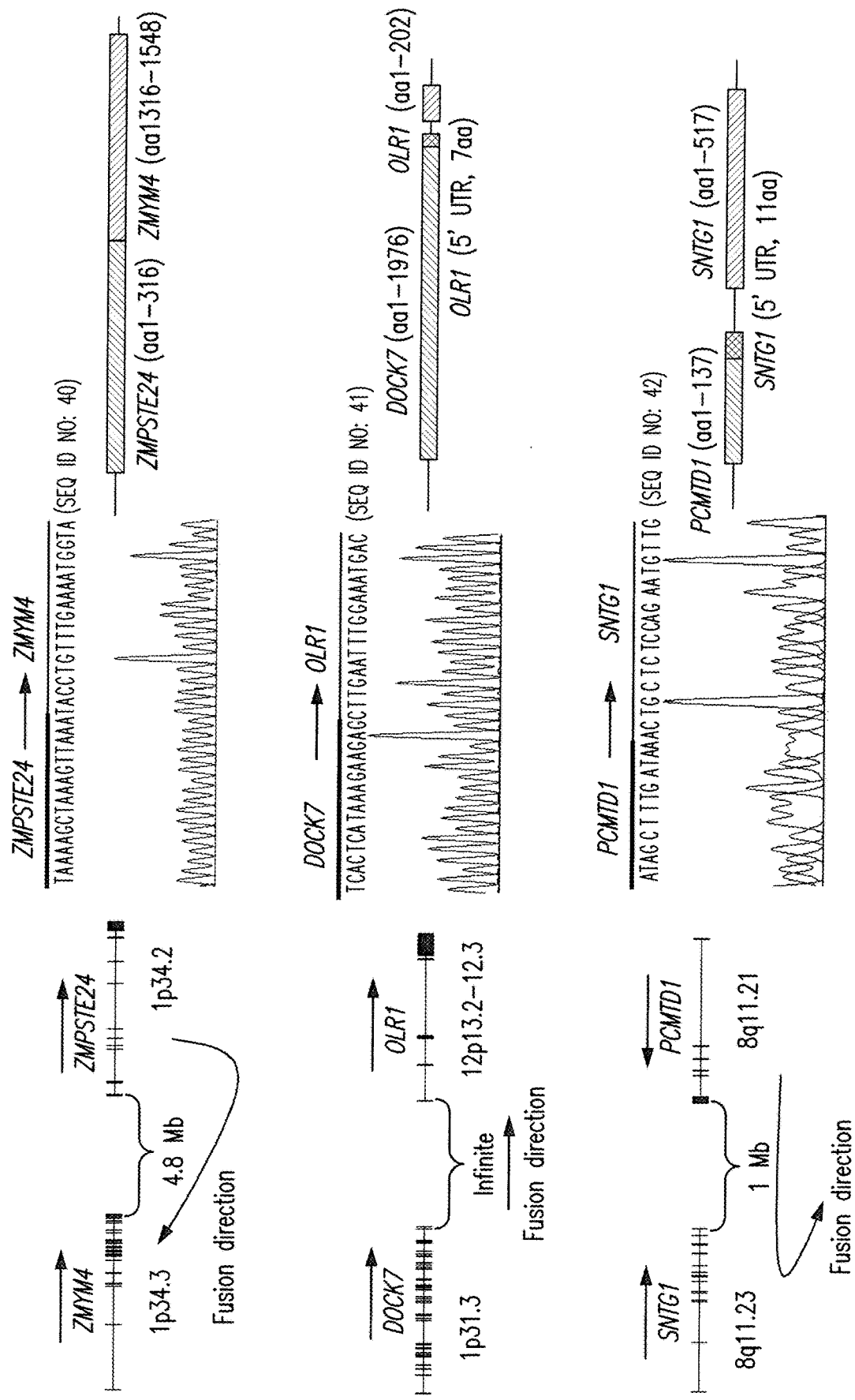
Figure 6:
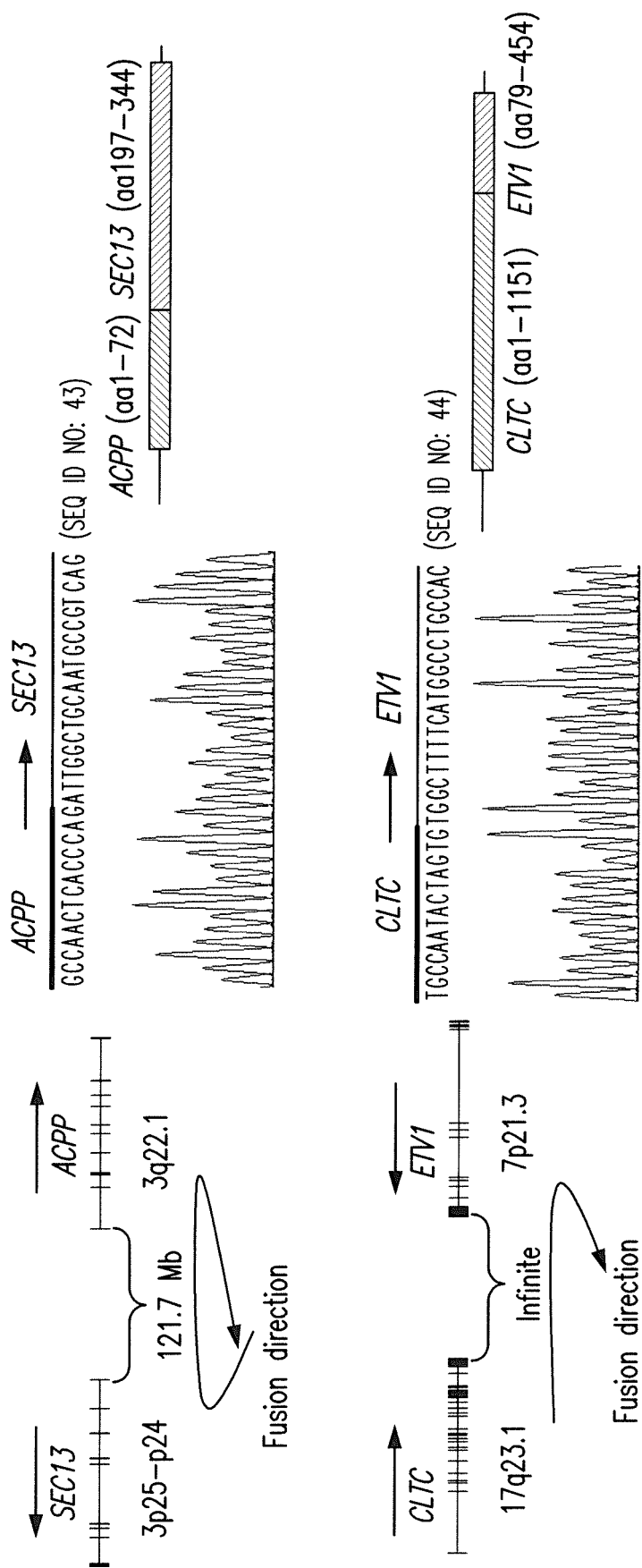

FIG. 6. Schematic diagram of fusion genes. Left panel: Schematic diagram of genome of fusion partners. Genetic locus, distance between partners, transcription direction and fusion direction are indicated. Middle panel: Histogram of Sanger sequencing surrounding the fusion point of each fusion gene (SEQ ID NOs: 40-44). Right panel: Predicted protein products of fusion genes. Blue: Head gene protein; Yellow: frameshift translation; Red: tail.

Figure 7:
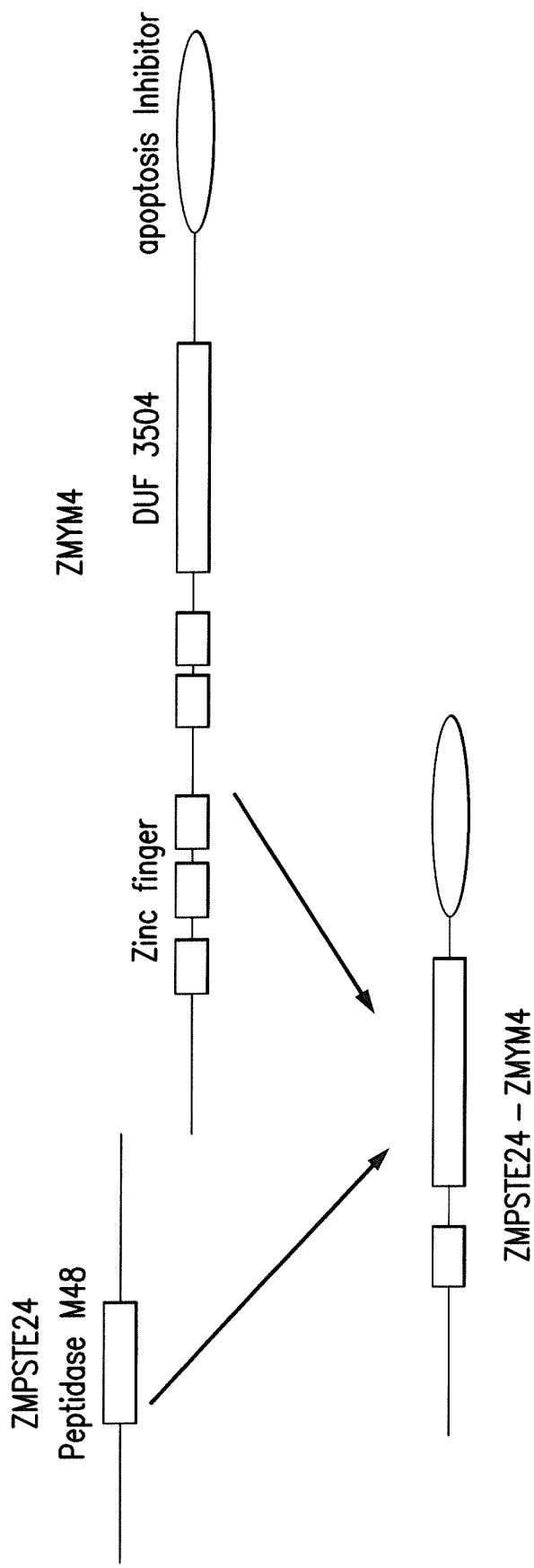

FIG. 7. Schematic diagram of ZMPSTE24-ZMYM5 fusion formation. Functional domains are indicated. The fusion formation between ZMPSTE24 and ZMYM4 produces a truncation of 159 amino acids from the C-terminus of ZMPSTE24 and 1315 amino acids from the N-terminus of ZMYM4. Motif analysis suggests that ZMPSTE24-ZMYM4 fusion will delete about 50% of the peptidase domain from ZMPSTE24 and remove all zinc fingers from ZMYM4, but will leave ZUF3504 (domain of unknown function) and apoptosis inhibitor domain intact.

Figure 8:
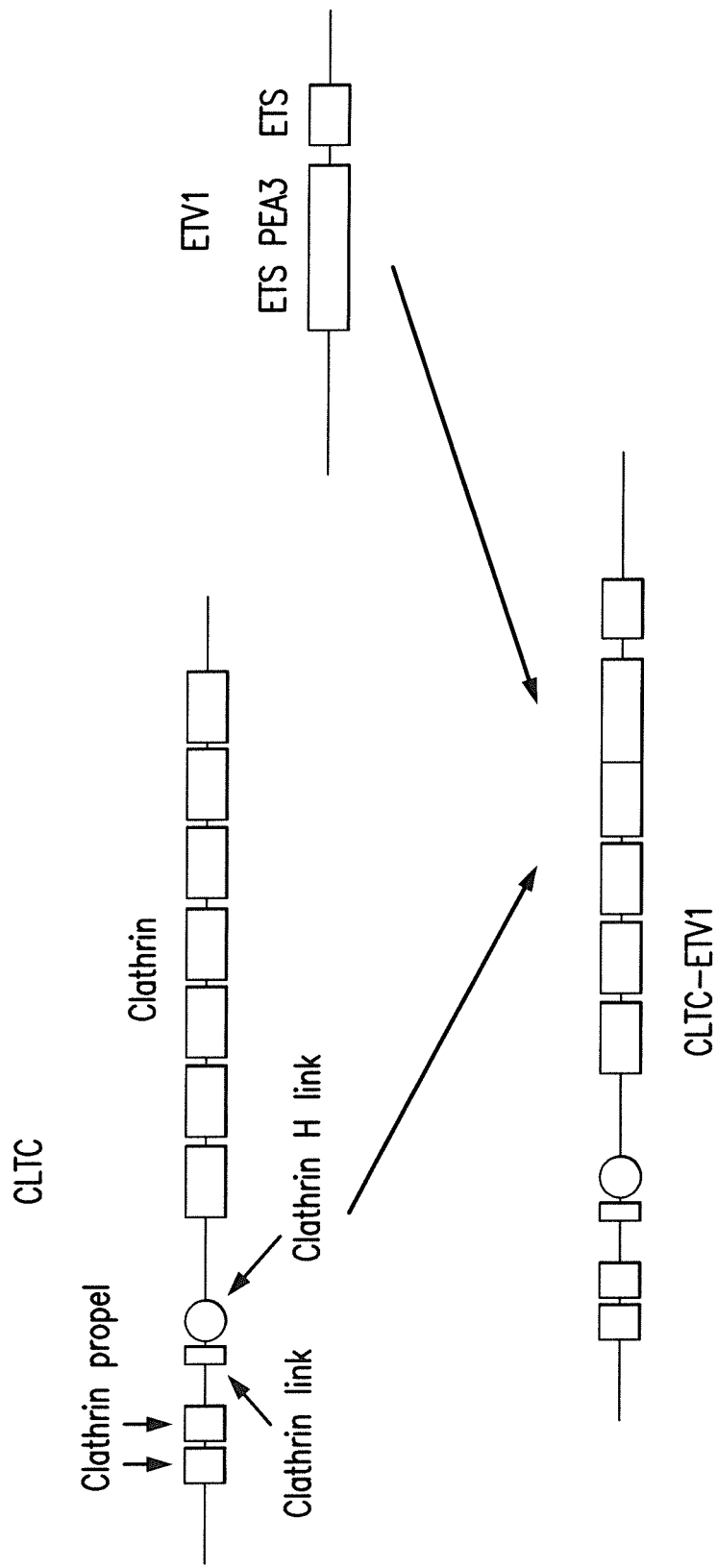

FIG. 8. Schematic diagram of CLTC-ETV1 fusion formation. Functional domains are indicated. CLTC-ETV1 fusion preserves a largely intact transcription domain in ETV1, and deletes 3 clathrin domains from CLTC. Truncation in the N-terminus of ETV1 eliminates all these regulatory elements from ETV1.

Figure 9:
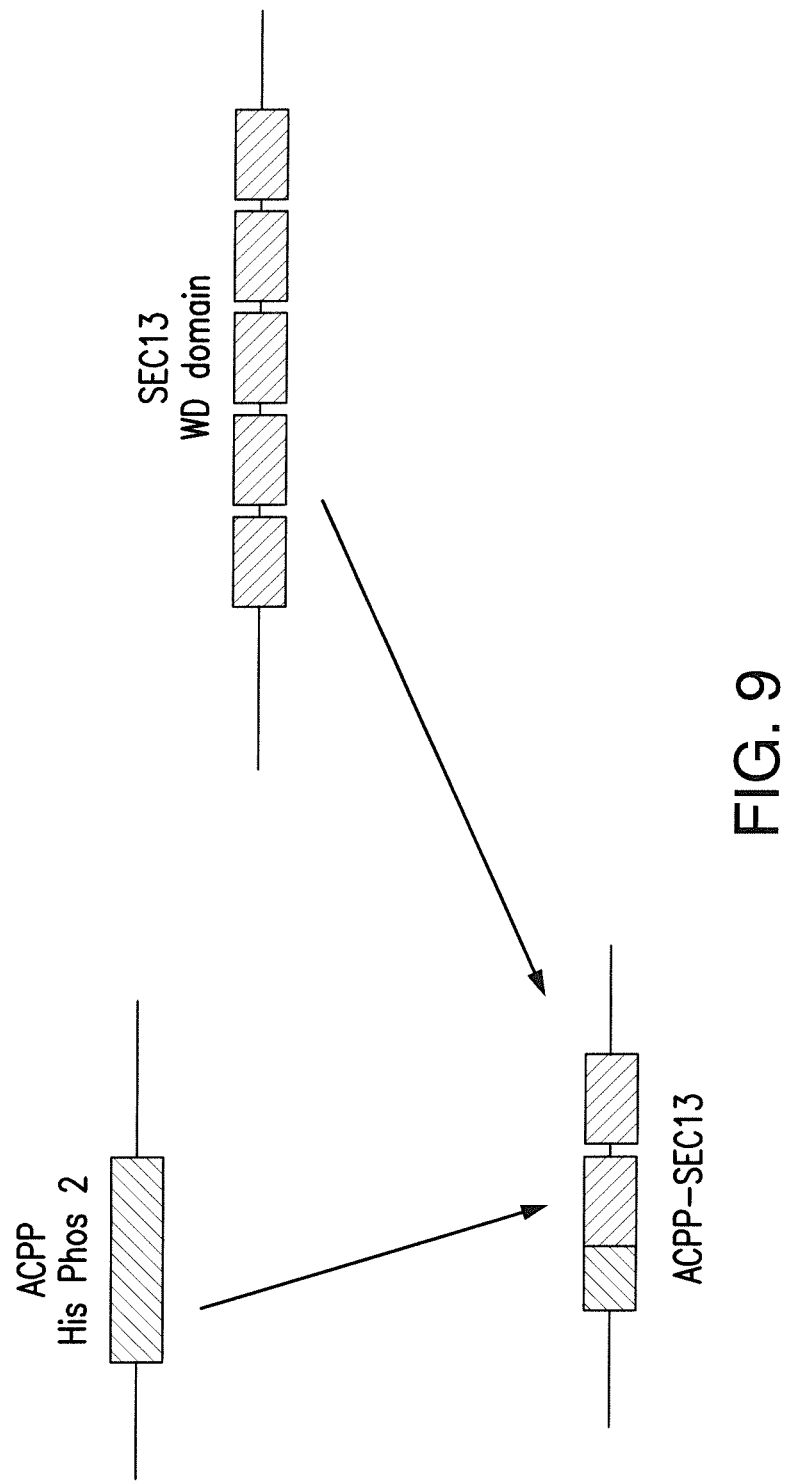

FIG. 9. Schematic diagram of ACPP-SEC13 fusion formation. Functional domains are indicated. In ACPP-SEC13 fusion, only the N-terminus 72 amino acids of ACPP is preserved, and over ⅔ of the phosphatase domain is truncated, while SEC13 loses 196 amino acids from its N-terminus and has 3 WD-repeat domains deleted.

Figure 10:
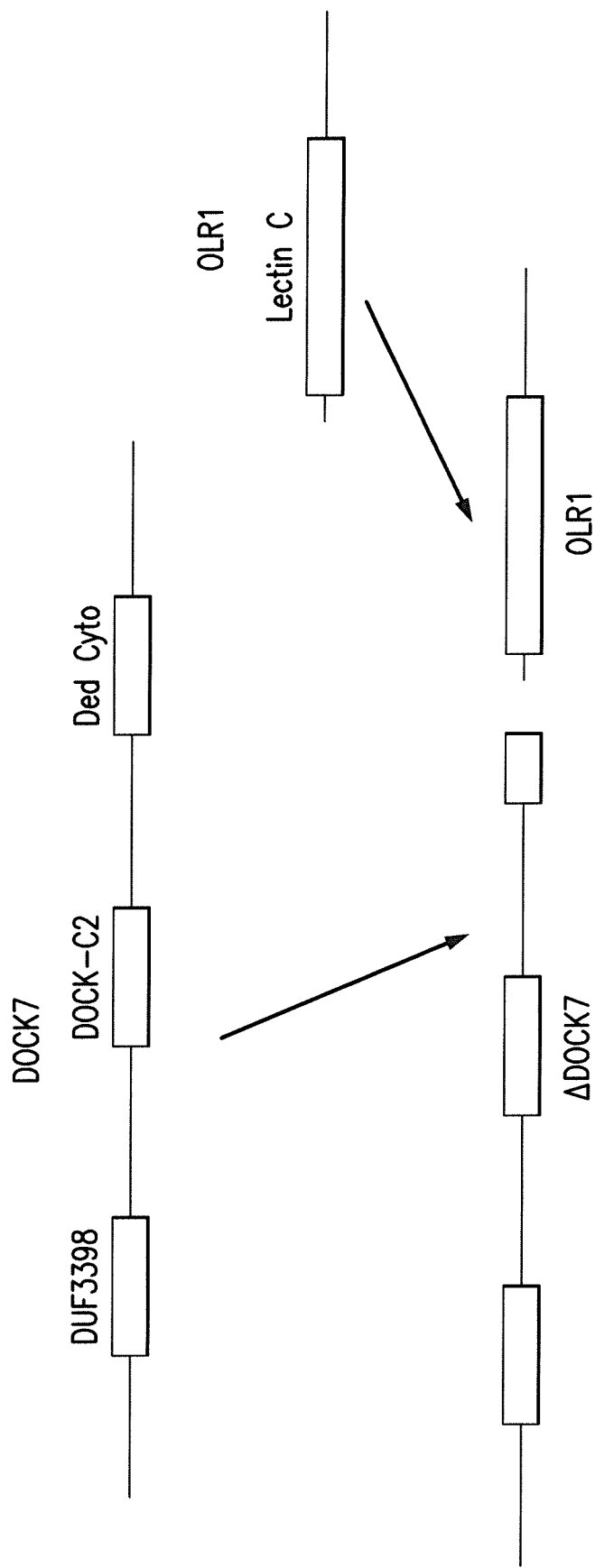

FIG. 10. Schematic diagram of DOCK7-OLR1 fusion formation. Functional domains are indicated. DOCK7-OLR1 does not produce a chimera protein. Separate translation of DOCK7 and OLR1 occurs from the fusion transcript. The fusion gene deletes a significant portion of cytokinesis domain of DOCK, and the fusion transcript will produce an intact OLR1 protein.

Figure 11:
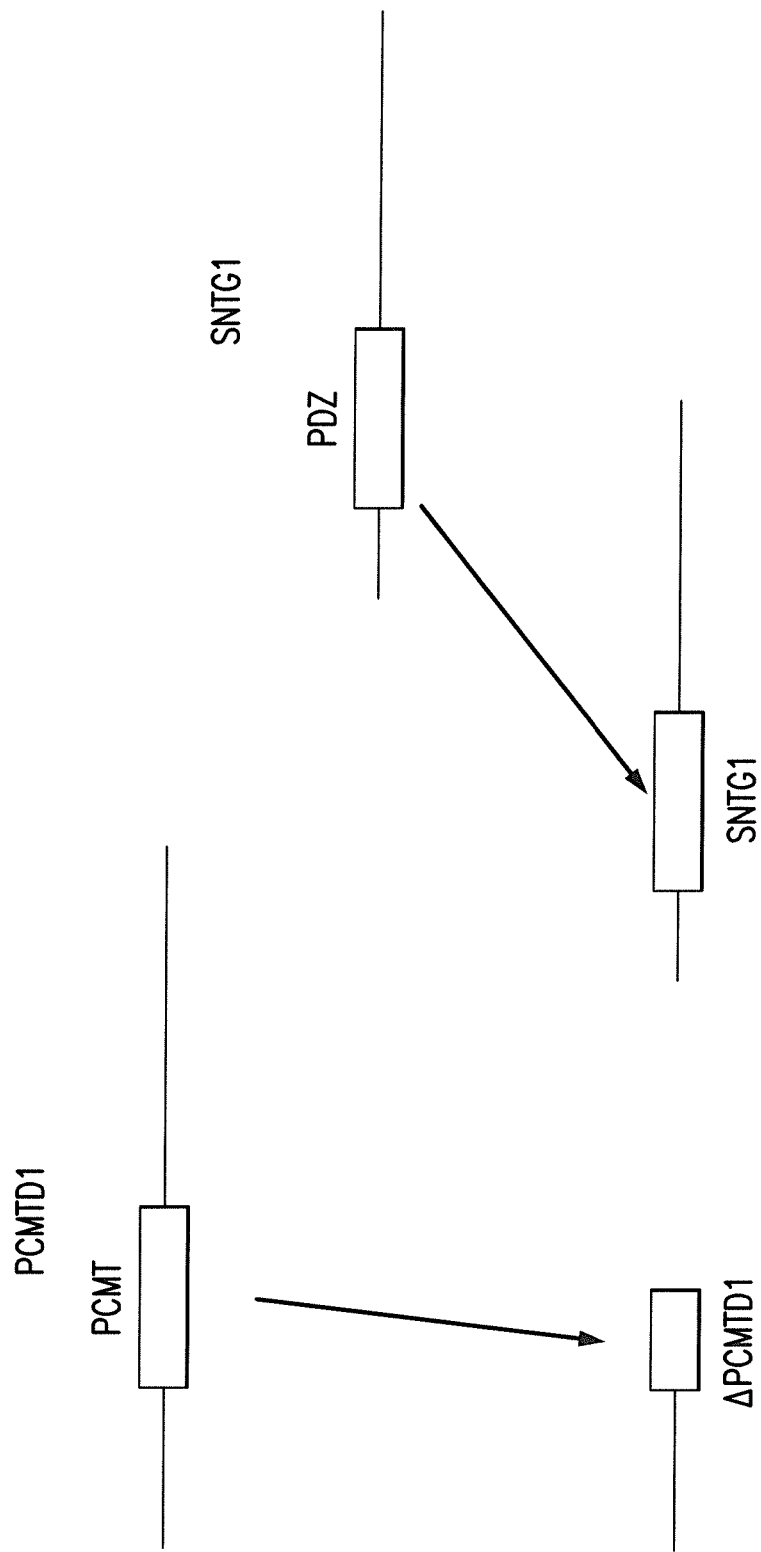

FIG. 11. Schematic diagram of PCMTD1-SNTG1 fusion formation. Functional domains are indicated. PCMTD1-SNTG1 fusion does not produce a chimera protein. PCMTD1-SNTG1 fusion produces a truncated PCMTD1, which removes half of the methyl-transferase domain of PCMTD1, and SNTG1 remains intact.

Figure 12:
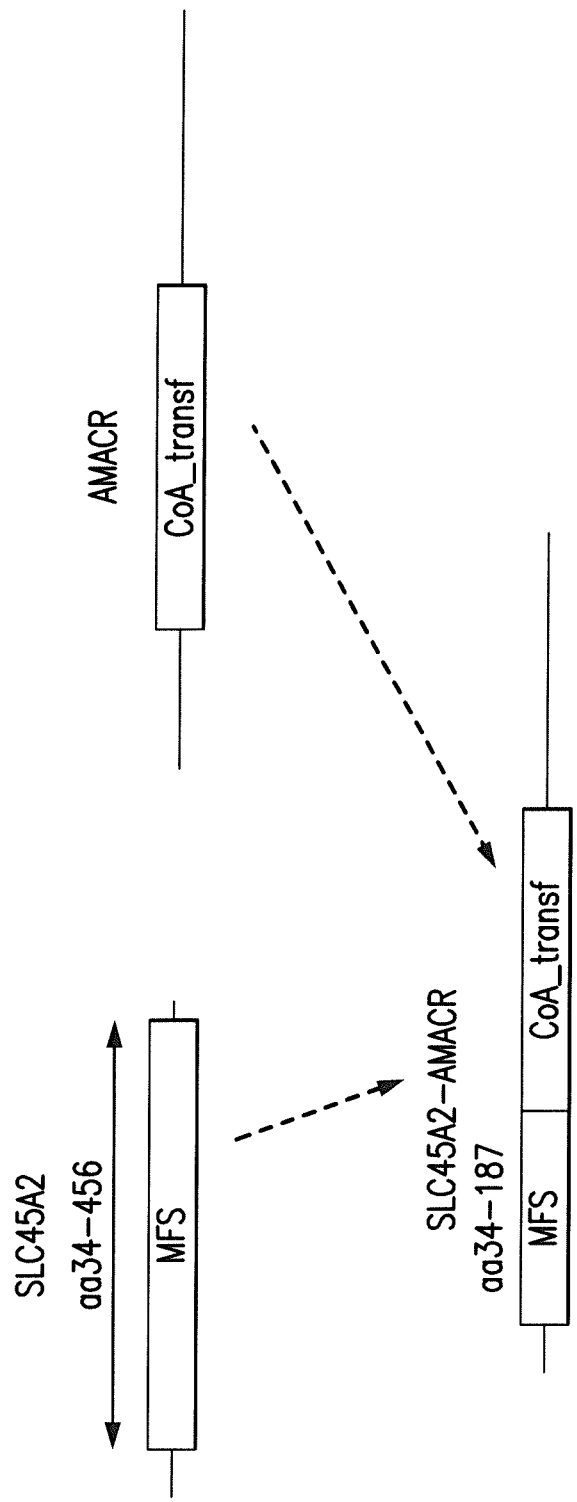

FIG. 12. Schematic diagram of SLC45A2-AMACR chimera protein. Fusion between SLC45A2 and AMACR results in truncation of two-third of (MFS) domain in SLC45A2, but largely retains CoA-transferase domain of AMACR. SLC45A2-AMACR produces a chimera protein with the N-terminal 187 amino acids of SLC45A2 and the C-terminal 311 amino acids of AMACR. SLC45A2-AMACR replaces 5 transmembrane and cytosolic domains of SLC45A2 with an intact racemase domain from AMACR, while leaves the extracellular and the N-terminal transmembrane domains intact.

FIG. 13A-D. MAN2A1-FER in human malignancies. (A) Schematic diagram of MAN2A1, FER and MAN2A1-FER proteins. FCH denotes FER-CP4 homologous region. PK denotes protein kinase. SH2 denotes Src Homology 2. (B) Chromosome breakpoints of MAN2A1-FER is located in intron 13 of MAN2A1 and intron 14 of FER. One breakpoint was identified in prostate cancer sample PRCa159T through whole genome sequencing. Another breakpoint was identified in liver cancer cell line HUH7 through nested PCRs. (C) Frequency of MAN2A1-FER fusion transcript in glioblastoma multiforme (GBM), Hepatocellular carcinoma (HCC), prostate cancer (PRCA), non-small cell lung cancer (NSCLC), ovarian cancer (OV) and esophageal adenocarcinoma (ESCA). The numbers of samples examined are indicated. (D) Expression of MAN2A1-FER protein in human cancers. Immunoblotting was performed on protein extracts from liver cancer cell lines HUH7 and HEP3B, prostate cancer samples positive (PRCA159T and PRCA23T) or negative (PRCA25T, PRCA2OT and PRCA119T) for MAN2A1-FER transcript, using antibodies specific for MAN2A1 or FER. MAN2A1, FER and MAN2A1-FER are indicated. Immunoblotting using antibodies for GAPDH was used as control.

FIG. 14A-D. MAN2A1-FER fusion protein is located in Golgi apparatus. (A) Expression of MAN2A1-FER-FLAG in pCDNA4-MA2A1-FER-FLAG/pCDNA6-TO transformed NIH3T3 (NMF) and HEP3B (HEPMF) cells. Immunoblotting using antibodies specific for FLAG or GAPDH was performed. (B) MAN2A1-FER-FLAG is colocalized with Golgi resident protein N-acetylgalactosaminyl-transferase. Immunofluorescence staining of FLAG and N-acetylgalactosaminyl-transferase. Pictures were taken with con-focal microscopy. (C) Sucrose gradient ultracentrifugation of HEPMF cells induced to express MAN2A1-FER-FLAG. Faction numbers are indicated at the top. Subcellular locations are indicated at the bottom. Immunoblotting was performed using the indicated antibodies (right). Receptor-binding cancer associated surface antigen (RCAS1) is used as a marker for Golgi apparatus. (D) MAN2A1-FER in Golgi was confirmed by Golgi isolation method. Golgi factions of HUH7 (top) and NMF (bottom) cells expressing MAN2A1-FER were isolated, and immunoblotted with antibodies specific for FER (HUH7) or FLAG (NMF). Antibodies specific for RCAS1, GAPDH and Histone 3 were used as purity controls. G—golgi; C—cytoplasm; N—nucleus.

FIG. 15A-G. Tyrosine kinase activity of MAN2A1-FER. (A) In vitro kinase assay using poly (EY 4:1) as substrate. GST-FER, GST-MAN2A1-FER and GST proteins were expressed in *Escherichia coli*. BL21, extracted and purified through glutathione column. Kinase activity was quantified and normalized to pmol per protein. (B) Crizotinib inhibits kinase activity of GST-MAN2A1-FER. (C) GST-MAN2A1-FER phosphorylated tyrosine 88 of EGFR. Top panel: ATP dosage dependent phosphorylation of HisTAG-EGFR$^{aa1-650}$ (lanes 1-8) or HisTAG-ΔEGFR N-terminusY88A (lane 9). Phosphorylation of HisTAG-ΔEGFR$^{aa1-650}$ by GST-MAN2A1-FER was performed excessive peptide 3 (FLKTIQEVAGYVLIALNTVER (SEQ ID NO: 144)) or mutant peptide 3 (FLKTIQEVAGAVLIALNTVER (SEQ ID NO: 145)) (lanes 7-8). Bottom panel: Phosphorylation assay on synthetic peptide listed in Table 4 by GST-MAN2A1-FER. (D) Immunoblot analyses of partial digested EGFR products from HEPMF cells with or without MAN2A1-FER-FLAG. The protein extracts from HEPMF cells were exposed to thrombin or hydroxylamine. This is followed by immunoprecipitation by antibodies specific for the N-terminus of EGFR. The immunoprecipitates were resolved in 15% SDS-PAGE and immunoblotted with antibodies specific phosphotyrosine. (E) MAN2A1-FER-FLAG activates EGFR. PC3 with inducible MAN2A21-FER-FLAG (PMF) or HEPMF cells were induced to express MAN2A1-FER-FLAG. Immunoblotting was performed using antibodies specific for pY1068, pY845 or pY. EGFR and GAPDH were used as controls. (F) Y88 of EGFR is required for MAN2A1-FER-FLAG induced activation of EGFR. Top panel: HEPMF cells were transfected with pCMV-ΔEGFR$^{Y88A}$-c-myc (lanes 1-2) or pCMV-EGFR-c-myc (lanes 3-4). These cells were induced to express MAN2A1-FER-FLAG and immunoprecipitated with anti-c-myc antibodies. The immunoprecipitates were then blotted with anti-phosphotyrosine antibodies. Bottom panel: Induction of MAN2A1-FER-FLAG expression as the top panel. This is followed by cross-linking of EGFR-c-myc, and then by blotting with anti-c-myc antibodies. (G) Immunostaining of EGFR pY1068 in prostate cancer samples positive (right) or negative (middle) for MAN2A1-FER. Normal prostate (left) was used as negative control.

FIG. 16A-D. Activation of EGFR signaling pathways by MAN2A1-FER PC3 (PMF), HEP3B (HEPMF), NIH3T3 (NMF) and A-172 (GMF) cells transformed with pCDNA4-MAN2A1-FERFLAG/pCDNA6-TO were treated with tetracycline to induce the expression of MAN2A1-FERFLAG (lanes 1-8). EGFR pY1068, B-raf pS445, MEK1/2 pS221 and Akt pS473 were examined for their phosphorylation status by immunoblotting. GAPDH, EGFR, B-raf, MEK1/2 and Akt were also immunoblotted as normalization controls. (B) Dominant negative mutant ΔEGFR$^{aa1-650}$ was transfected into the cells of (A) (lanes 9-16). Similar immunoblotting was performed as (A). (C) PC3 (PMFΔK), HEP3B (HEPMFΔK), NIH3T3 (NMFΔK), A-172 (GMFΔK) cells transformed with pCDNA4-ΔMAN2A1-FER-FLAG$^{K723A}$/pCDNA6-TO were treated with tetracycline to induce the expression of MAN2A1-FER$^{K723A}$-FLAG (lanes 17-24). Similar immunoblotting was performed as (A). (D) Interruption of MAN2A1-FER in HUH7 cells decreased hyperphosphorylation of EGFR, B-raf, MEK and Akt.

FIG. 17A-F. Pro-growth and invasion activity of MAN2A1-FER. (A) Cell cycle analyses of cells transformed with pCDNA4-ΔMAN2A1-FER-FLAG$^{K723A}$/pCDNA6-TO or its wild type counterpart. Dominant negative mutant ΔEGFR$^{aa1-650}$ was used in HEPMF cells to examine whether MAN2A1-FER pro-growth activity was dependent on EGFR activation. HUH7 and its MAN2A1-FER knock-out counterpart (KO) were used to examine whether cell growth was dependent on MAN2A1-FER. (B) Colony formation assays of the duplicates from (A). (C) Matrigel traverse analysis of PMF, DMF, HEPMF GMF and HMF cells with or without MAN2A1-FER-FLAG. (D) MAN2A1-FER increased tumor volumes of xenografted human cancers. (E) MAN2A1-FER increased the rate of metastasis of xenografted human cancers. (F) MAN2A1-FER increased the mortality of mice xenografted with human cancers.

Figure 18:
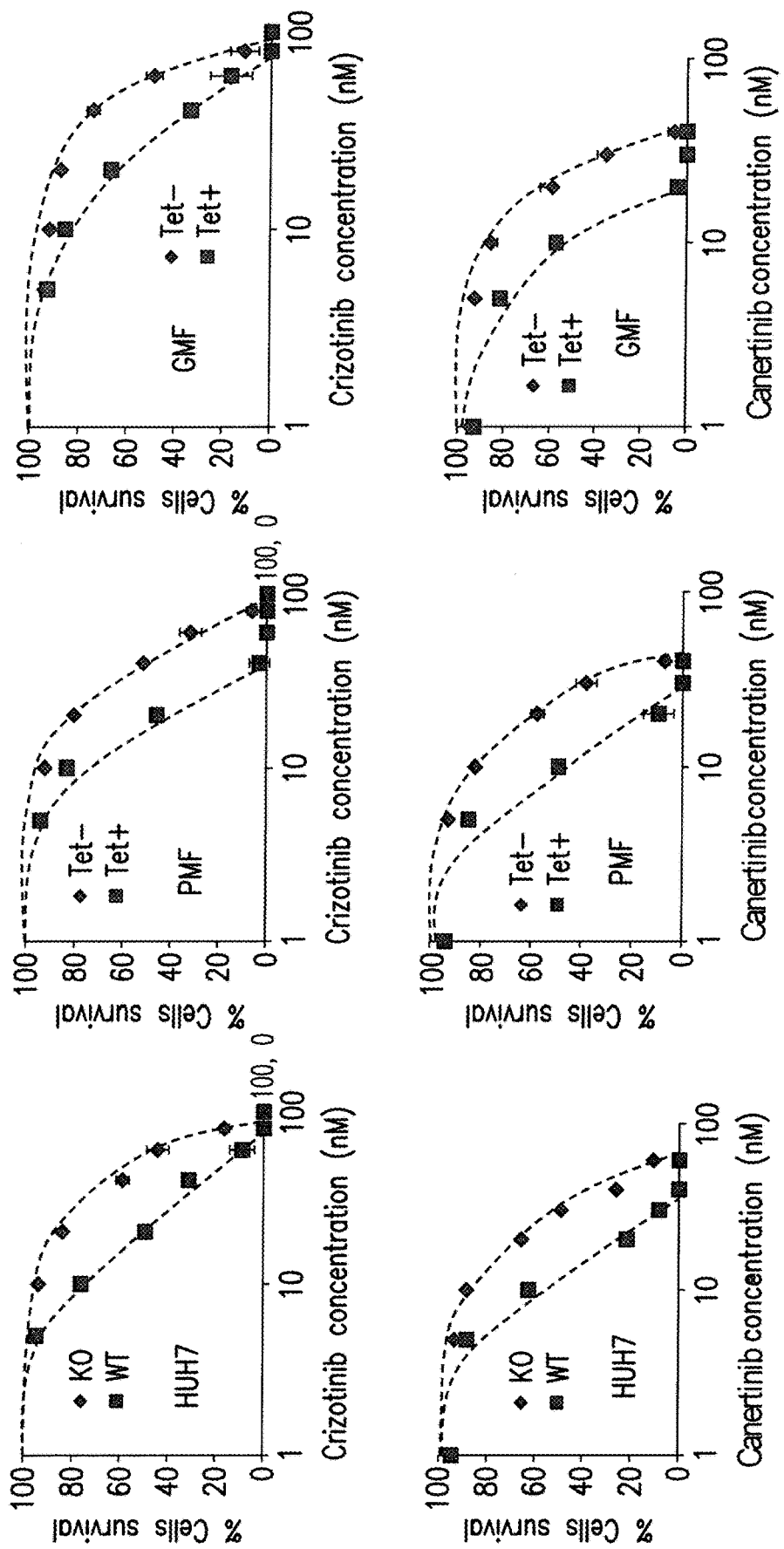

FIG. 18. Killing of cancer cells positive for MAN2A1-FER by crizotinib or canertinib. Top panel: HUH7 or its MAN2A1-FER knockout counterpart cells were treated with various concentrations of crizotinib or canertinib. Factions of cell death were then quantified by Annexin V and propridium iodide staining. Middle panel: PMF cells induced with or without tetracycline were treated with various concentration of crizotinib or canertinib. Factions of cell death were then quantified by Annexin V and propridium iodide staining. Bottom panel: GMF cells induced with or without tetracycline were treated with various concentration of crizotinib or canertinib. Factions of cell death were then quantified by Annexin V and propridium iodide staining.

Figure 19A:
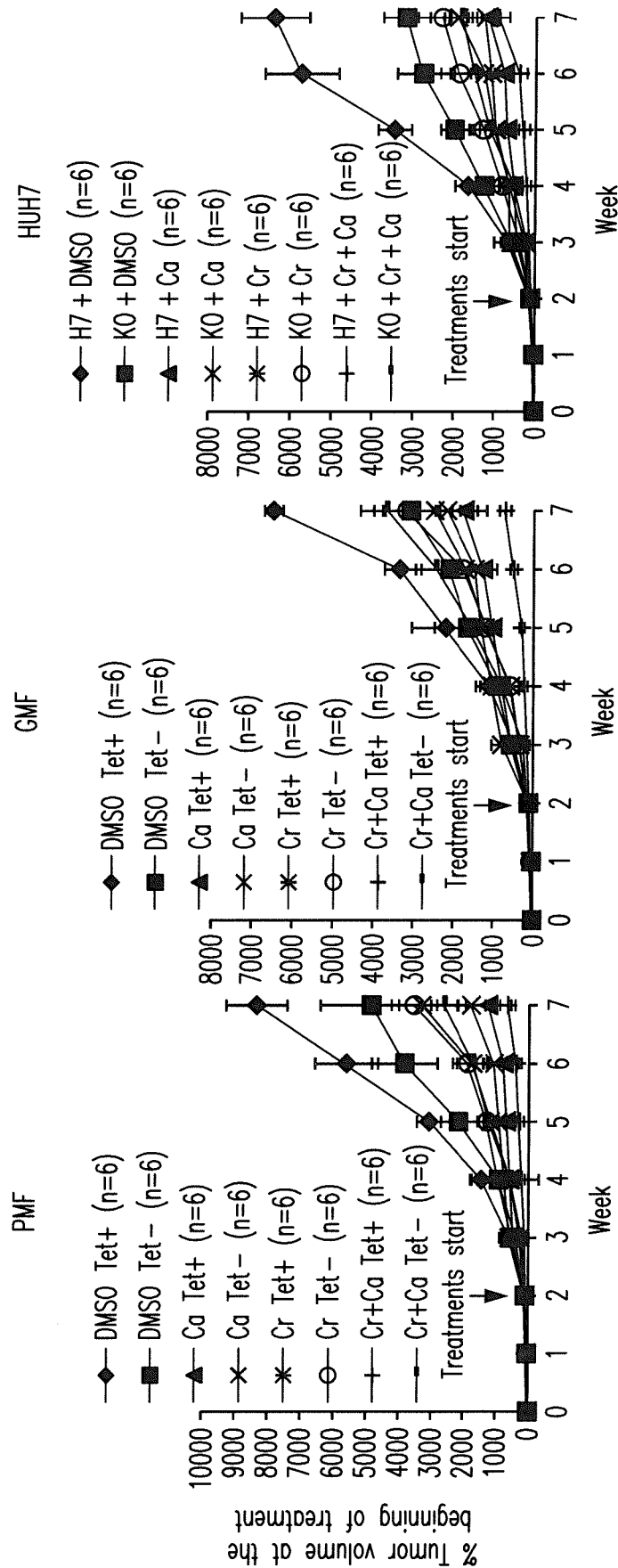

FIG. 19A-C. MAN2A1-FER increased cancer sensitivity to kinase inhibitors crizotinib and canertinib. (A) Treatment of crizotinib or canertinib decreased the volumes of xenografted cancers positive for MAN2A1-FER. (B) Treatment of crizotinib or canertinib decreased the metastasis incidents of xenografted cancers positive for MAN2A1-FER, but not those negative for MAN2A1-FER. (C) Treatment of crizotinib or canertinib decreased the mortality of SCID mice xenografted with cancers positive for MAN2A1-FER, but not those negative for MAN2A1-FER.

FIG. 20A-E. MAN2A1-FER-FLAG induced spontaneous liver cancer in mice with somatic Pten deletion. (A) Schematic diagram of the procedure. (B) Representative pictures of mice with gross liver cancer (right) and negative control (left). AAV-CRE plus control vector pT3 were used as controls. (C) Tail vein hydrodynamic injection of pT3-MAN2A1-FER-FLAG increased liver size. AAV-CRE plus control vector pT3 were used as controls. (D) Tail vein hydrodynamic injection of pT3-MAN2A1-FER-FLAG induced activation of EGFR and Akt. AAV-CRE plus control vector pT3 were used as controls. (E) Progression of liver cancer produced by tail vein hydrodynamic injection of pT3-MAN2A1-FER-FLAG. AAV-CRE plus control vector pT3 were used as controls.

Figure 21:
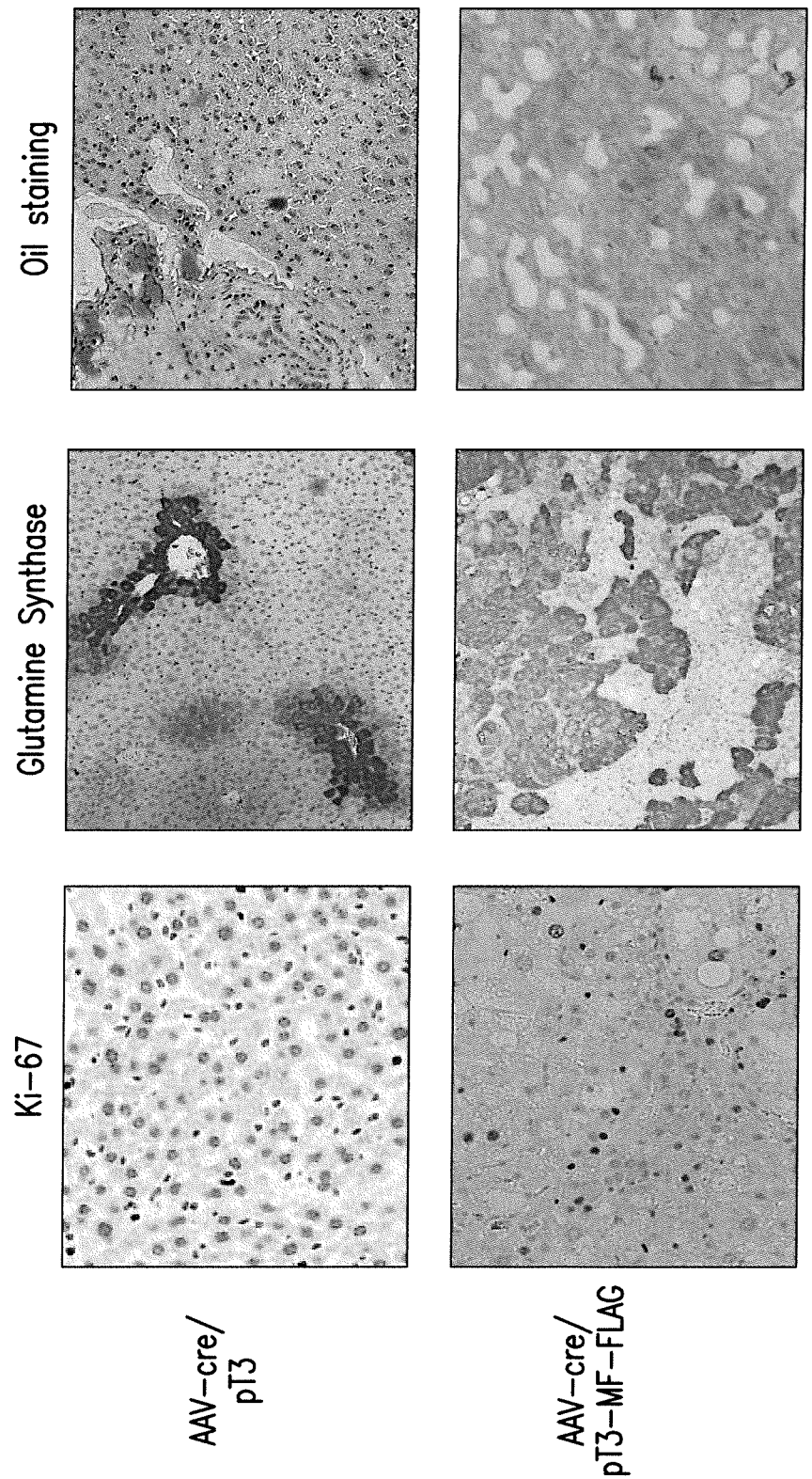

FIG. 21. Representative images of Ki-67, Glutamine synthase and oil staining of AAV-cre and pT3-MAN2A1-FER-FLAG treated Pten$^{tm1Hwu/J}$ mice. AAV-cre and pT3 treated mice were used as controls.

FIG. 22. Taqman quantitative reverse transcription (RT) PCR of HCC and normal liver organ donor samples. Original normalized graphs of Taqman RT-PCR were shown. *MAN2A1-FER fusion was verified by Sanger sequencing.

Figures 23A, 23B:
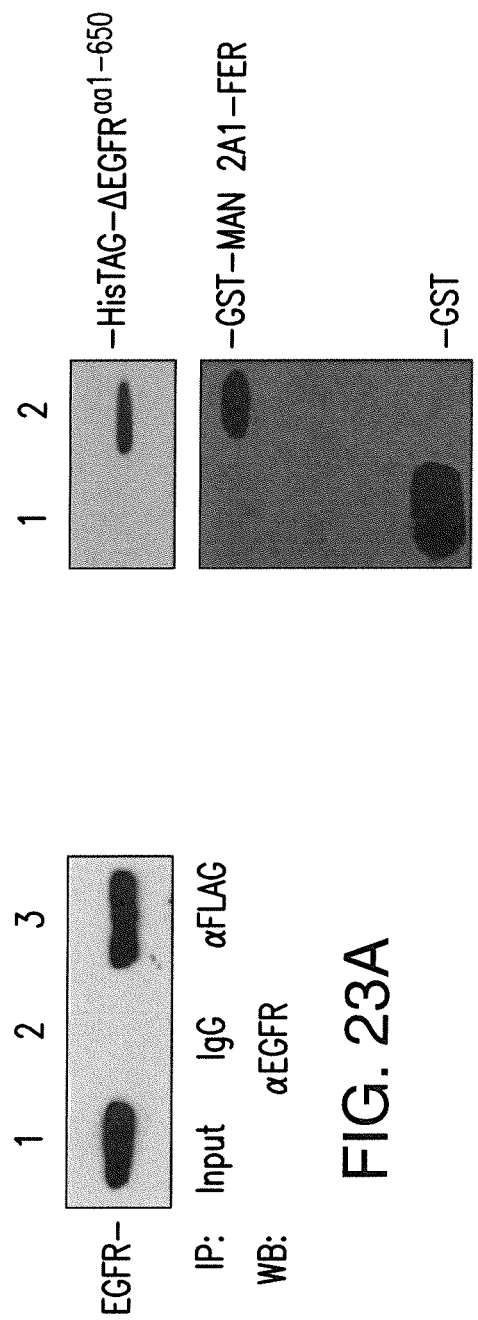

FIG. 23A-B. MAN2A1-FER binds EGFR in vitro and in vivo. (A) Co-immunoprecipitation of MAN2A1-FER-FLAG with EGFR. (B) In vitro binding of purified recombinant GST MAN2A1-FER with EGFR N-terminus (HisTAG-DEGFR$^{aa1-650}$). IP, immunoprecipitation; WB, Western blot.

Figure 24:
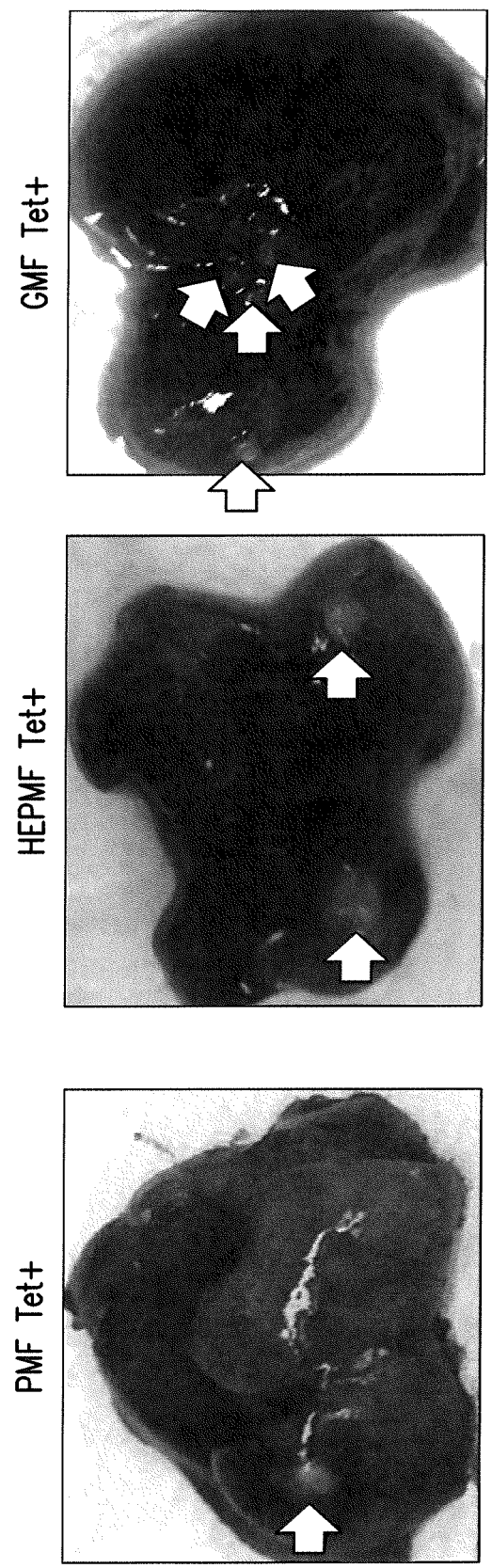

FIG. 24. Representative images of metastatic cancer nodules in liver. Xenografted tumor cells and tetracycline (tet) treatment are indicated. Green arrows indicate the metastatic cancer nodule in the livers.

Figure 25:
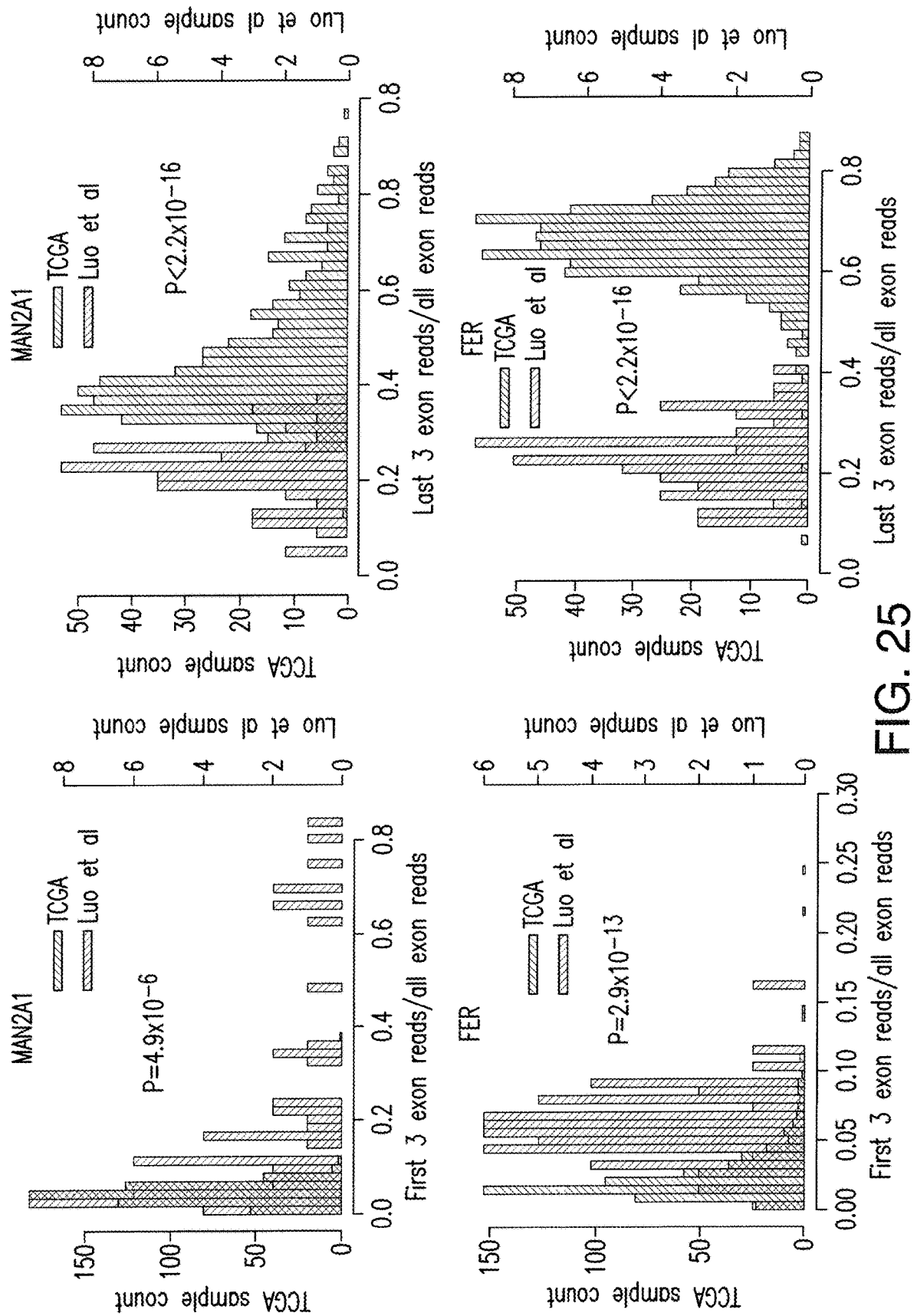

FIG. 25. Transcriptome sequencing read distributions of MAN2A1 and FER genes. The graphs represent distribution of individual sample on the ratio of read counts of first 3 exons to reads of all exons of MAN2A1 (top left) or FER (bottom left) or the ratios of read counts of last 3 exons to reads of all exons of MAN2A1 (top right) or FER (bottom right). Orange samples from The Cancer Genome Atlas (TCGA) data set (550 samples); Luo et al. data set (54 samples) (Luo et al. Discovery and classification of fusion transcripts in prostate cancer and normal prostate tissue. Am J Pathol 185:1834-1845 (2015)). P values are indicated.

Figure 26:
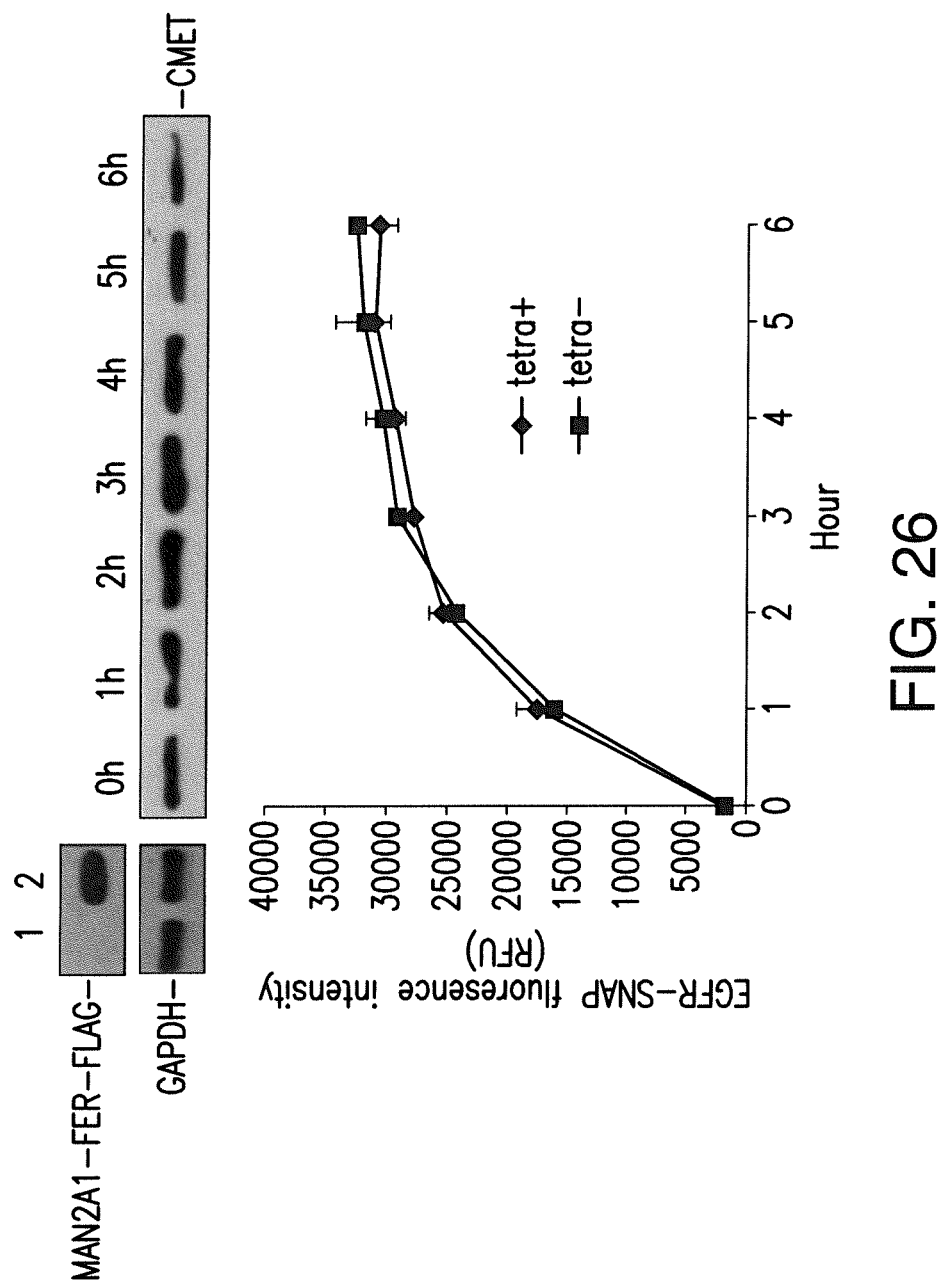

FIG. 26. Pulse-chase analysis of EGFR-SNAP trafficking to the plasma membrane. pEGFR-SNAP was transfected into HEPMF cells. These cells were then treated with or without 5 mg/mL tetracycline to induce the expression of MAN2A1-FER-FLAG as shown in FIG. 14. The fluorescence was blocked by replacing the medium with 10 mM SNAP-Cell Block (bromothenylpteridine) blocking medium for 20 minutes. The blocking was released by washing these cells twice with culture medium. EGFR-SNAP proteins were then pulsed with SNAP-Cell 505-Star (5 mM) for 30 minutes, and chased for 0, 1, 2, 3, 4, 5, and 6 hours. The plasma membrane fraction was purified. The fluorescence of EGFR-SNAP protein in the plasma membrane was quantified by fluorescence microplate reader at 532 nM. RFU, relative fluorescence unit.

5. DETAILED DESCRIPTION OF THE INVENTION

For clarity and not by way of limitation the detailed description of the invention is divided into the following subsections:
(i) fusion genes;
(ii) fusion gene detection;
(iii) cancer targets;
(iv) methods of treatment;
(v) pharmaceutical compositions; and
(vi) kits.

5.1 Fusion Genes

The term "fusion gene," as used herein, refers to a nucleic acid or protein sequence which combines elements of the recited genes or their RNA transcripts in a manner not found in the wild type/normal nucleic acid or protein sequences. For example, but not by way of limitation, in a fusion gene in the form of genomic DNA, the relative positions of portions of the genomic sequences of the recited genes is altered relative to the wild type/normal sequence (for example, as reflected in the NCBI chromosomal positions or sequences set forth herein). In a fusion gene in the form of mRNA, portions of RNA transcripts arising from both component genes are present (not necessarily in the same register as the wild-type transcript and possibly including portions normally not present in the normal mature transcript). In non-limiting embodiments, such a portion of genomic DNA or mRNA may comprise at least about 10 consecutive nucleotides, or at least about 20 consecutive nucleotides, or at least about 30 consecutive nucleotides, or at least 40 consecutive nucleotides. In certain embodiments, such a portion of genomic DNA or mRNA may comprise up to about 10 consecutive nucleotides, up to about 50 consecutive nucleotides, up to about 100 consecutive nucleotides, up to about 200 consecutive nucleotides, up to about 300 consecutive nucleotides, up to about 400 consecutive nucleotides, up to about 500 consecutive nucleotides, up to about 600 consecutive nucleotides, up to about 700 consecutive nucleotides, up to about 800 consecutive nucleotides, up to about 900 consecutive nucleotides, up to about 1,000 consecutive nucleotides, up to about 1,500 consecutive nucleotides or up to about 2,000 consecutive nucleotides of the nucleotide sequence of a gene present in the fusion gene. In certain embodiments, such a portion of genomic DNA or mRNA may comprise no more than about 10 consecutive nucleotides, about 50 consecutive nucleotides, about 100 consecutive nucleotides, about 200 consecutive nucleotides, about 300 consecutive nucleotides, about 400 consecutive nucleotides, about 500 consecutive nucleotides, about 600 consecutive nucleotides, about 700 consecutive nucleotides, about 800 consecutive nucleotides, about 900 consecutive nucleotides, about 1,000 consecutive nucleotides, about 1,500 consecutive nucleotides or about 2,000 consecutive nucleotides of the nucleotide sequence of a gene present in the fusion gene. In certain embodiments, such a portion of genomic DNA or mRNA does not comprise the full wild type/normal nucleotide sequence of a gene present in the fusion gene. In a fusion gene in the form of a protein, portions of amino acid sequences arising from both component genes are present (not by way of limitation, at least about 5 consecutive amino acids or at least about 10 amino acids or at least about 20 amino acids or at least about 30 amino acids). In certain embodiments, such a portion of a fusion gene protein may comprise up to about 10 consecutive amino acids, up to about 20 consecutive amino acids, up to about 30 consecutive amino acids, up to about 40 consecutive amino acids, up to about 50 consecutive amino acids, up to about 60 consecutive amino acids, up to about 70 consecutive amino acids, up to about 80 consecutive amino acids, up to about 90 consecutive amino acids, up to about 100 consecutive amino acids, up to about 120 consecutive amino acids, up to about 140 consecutive amino acids, up to about 160 consecutive amino acids, up to about 180 consecutive amino acids, up to about 200 consecutive amino acids, up to about 220 consecutive amino acids, up to about 240 consecutive amino acids, up to about 260 consecutive amino acids, up to about 280 consecutive amino acids or up to about 300 consecutive amino acids of the amino acid sequence encoded by a gene present in the fusion gene. In certain embodiments, such a portion of a fusion gene protein may comprise no more than about 10 consecutive amino acids, about 20 consecutive amino acids, about 30 consecutive amino acids, about 40 consecutive amino acids, about 50 consecutive amino acids, about 60 consecutive amino acids, about 70 consecutive amino acids, about 80 consecutive amino acids, about 90 consecutive amino acids, about 100 consecutive amino acids, about 120 consecutive amino acids, about 140 consecutive amino acids, about 160 consecutive amino acids, about 180 consecutive amino acids, about 200 consecutive amino acids, about 220 consecutive amino acids, about 240 consecutive amino acids, about 260 consecutive amino acids, about 280 consecutive amino acids or about 300 consecutive amino acids of the amino acid sequence encoded by a gene present in the fusion gene. In certain embodiments, such a portion of a fusion gene protein does not comprise the full wild type/ normal amino acid sequence encoded by a gene present in the fusion gene. In this paragraph, portions arising from both genes, transcripts or proteins do not refer to sequences which may happen to be identical in the wild type forms of both genes (that is to say, the portions are "unshared"). As such, a fusion gene represents, generally speaking, the splicing together or fusion of genomic elements not normally joined together. See WO 2015/103057 and WO 2016/011428, the contents of which are hereby incorporated by reference, for additional information regarding the disclosed fusion genes.

The fusion gene TRMT11-GRIK2 is a fusion between the tRNA methyltransferase 11 homolog ("TRMT11") and glutamate receptor, ionotropic, kainate 2 ("GRIK2") genes. The human TRMT11 gene is typically located on chromosome 6q11.1 and the human GRIK2 gene is typically located on chromosome 6q16.3. In certain embodiments, the TRMT11 gene is the human gene having NCBI Gene ID No: 60487, sequence chromosome 6; NC_000006.11 (126307576 . . . 126360422) and/or the GRIK2 gene is the human gene having NCBI Gene ID No:2898, sequence chromosome 6; NC_000006.11 (101841584 . . . 102517958). In certain embodiments, the junction (also referred to herein as chromosomal breakpoint and/or junction fragment) of a TRMT11-GRIK2 fusion gene comprises a sequence as shown in FIG. 1 and/or Table 1.

The fusion gene SLC45A2-AMACR is a fusion between the solute carrier family 45, member 2 ("SLC45A2") and alpha-methylacyl-CoA racemase ("AMACR") genes. The human SLC45A2 gene is typically located on human chromosome 5p13.2 and the human AMACR gene is typically located on chromosome 5p13. In certain embodiments the SLC45A2 gene is the human gene having NCBI Gene ID No: 51151, sequence chromosome 5; NC_000005.9 (33944721 . . . 33984780, complement) and/or the AMACR gene is the human gene having NCBI Gene ID No:23600, sequence chromosome 5; NC_000005.9 (33987091 . . . 34008220, complement). In certain embodiments, the junction and/or junction fragment of a SLC45A2-AMACR fusion gene comprises a sequence as shown in FIG. 1 and/or Table 1.

The fusion gene MTOR-TP53BP1 is a fusion between the mechanistic target of rapamycin ("MTOR") and tumor protein p53 binding protein 1 ("TP53BP1") genes. The human MTOR gene is typically located on chromosome 1p36.2 and the human TP53BP1 gene is typically located on chromosome 15q15-q21. In certain embodiments, the MTOR gene is the human gene having NCBI Gene ID No:2475, sequence chromosome 1 NC_000001.10 (11166588 . . . 11322614, complement) and/or the TP53BP1gene is the human gene having NCBI Gene ID No: 7158, sequence chromosome 15; NC_000015.9 (43695262 . . . 43802707, complement). In certain embodiments, the junction and/or junction fragment of a MTOR-TP53BP1 fusion gene comprises a sequence as shown in FIG. 1 and/or Table 1.

The fusion gene LRRC59-FLJ60017 is a fusion between the leucine rich repeat containing 59 ("LRRC59") gene and the "FLJ60017" nucleic acid. The human LRRC59 gene is typically located on chromosome 17q21.33 and nucleic acid encoding human FLJ60017 is typically located on chromosome 11q12.3. In certain embodiments, the LRRC59 gene is the human gene having NCBI Gene ID No:55379, sequence chromosome 17; NC_000017.10 (48458594 . . . 48474914, complement) and/or FLJ60017 has a nucleic acid sequence as set forth in GeneBank AK_296299. In certain embodiments, the junction and/or junction fragment of a LRRC59-FLJ60017 fusion gene comprises a sequence as shown in FIG. 1, FIG. 2 and/or Table 1.

The fusion gene TMEM135-CCDC67 is a fusion between the transmembrane protein 135 ("TMEM135") and coiled-coil domain containing 67 ("CCDC67") genes. The human TMEM135 gene is typically located on chromosome 11q14.2 and the human CCDC67 gene is typically located on chromosome 11q21. In certain embodiments the TMEM135 gene is the human gene having NCBI Gene ID No: 65084, sequence chromosome 11; NC_000011.9 (86748886 . . . 87039876) and/or the CCDC67 gene is the human gene having NCBI Gene ID No: 159989, sequence chromosome 11; NC_000011.9 (93063156 . . . 93171636). In certain embodiments, the junction and/or junction fragment of a TMEM135-CCDC67 fusion gene comprises a sequence as shown in FIG. 1, FIG. 2 and/or Table 1.

The fusion gene CCNH-C5orf30 is a fusion between the cyclin H ("CCNH") and chromosome 5 open reading frame 30 ("C5orf30") genes. The human CCNH gene is typically located on chromosome 5q13.3-q14 and the human C5orf30gene is typically located on chromosome 5q21.1. In certain embodiments, the CCNH gene is the human gene having NCBI Gene ID No: 902, sequence chromosome 5; NC_000005.9 (86687310 . . . 86708850, complement) and/ or the C5orf30gene is the human gene having NCBI Gene ID No: 90355, sequence chromosome 5; NC_000005.9 (102594442 . . . 102614361). In certain embodiments, the junction and/or junction fragment of a CCNH-C5orf30 fusion gene comprises a sequence as shown in FIG. 1, FIG. 2, FIG. 5 and/or Table 1.

The fusion gene KDM4B-AC011523.2 is a fusion between lysine (K)-specific demethylase 4B ("KDM4B") and chromosomal region "AC011523.2". The human KDM4B gene is typically located on chromosome 19p13.3 and the human AC011523.2 region is typically located on chromosome 19q13.4. In certain embodiments the KDM4B gene is the human gene having NCBI Gene ID NO: 23030, sequence chromosome 19; NC_000019.9 (4969123 . . . 5153609); and/or the AC011523.2 region comprises a sequence as shown in FIG. 1. In certain embodiments, the junction and/or junction fragment of a KDM4B-AC011523.2 fusion gene comprises a sequence as shown in FIG. 1 and/or Table 1.

The fusion gene MAN2A1-FER is a fusion between mannosidase, alpha, class 2A, member 1 ("MAN2A1") and (fps/fes related) tyrosine kinase ("FER"). The human MAN2A1 gene is typically located on chromosome 5q21.3 and the human FER gene is typically located on chromosome 5q21. In certain embodiments, the MAN2A1gene is the human gene having NCBI Gene ID NO: 4124, sequence chromosome 5; NC_000005.9 (109025156 . . . 109203429) or NC_000005.9 (109034137 . . . 109035578); and/or the FER gene is the human gene having NCBI Gene ID NO: 2241, sequence chromosome 5: NC_000005.9

(108083523 . . . 108523373). In certain embodiments, the junction and/or junction fragment of a MAN2A1-FER fusion gene comprises a sequence as shown in FIG. 1, FIG. 13 and/or Table 1.

The fusion gene PTEN-NOLC1 is a fusion between the phosphatase and tension homolog ("PTEN") and nucleolar and coiled-body phosphoprotein 1 ("NOLC1"). The human PTEN gene is typically located on chromosome 10q23.3 and the human NOLC1 gene is typically located on chromosome 10q24.32. In certain embodiments, the PTEN gene is the human gene having NCBI Gene ID NO: 5728, sequence chromosome 10; NC_000010.11 (87863438 . . . 87970345) and/or the NOLC1 gene is the human gene having NCBI Gene ID NO: 9221, sequence chromosome 10; NC_000010.11 (102152176 . . . 102163871). In certain embodiments, the junction and/or junction fragment of a PTEN-NOLC1 fusion gene comprises a sequence as shown in FIG. 3 and/or Table 1.

The fusion gene ZMPSTE24-ZMYM4 is a fusion between zinc metallopeptidase STE24 ("ZMPSTE24") and zinc finger, MYM-type 4 ("ZMYM4"). The human ZMPSTE24 is typically located on chromosome 1p34 and the human ZMYM4 gene is typically located on chromosome 1p32-p34. In certain embodiments, the ZMPSTE24 gene is the human gene having NCBI Gene ID NO: 10269, sequence chromosome 1; NC_000001.11 (40258050 . . . 40294184) and/or the ZMYM4 gene is the human gene having NCBI Gene ID NO: 9202, sequence chromosome 1; NC_000001.11 (35268850 . . . 35421944). In certain embodiments, the junction and/or junction fragment of a ZMPSTE24-ZMYM4 fusion gene comprises a sequence as shown in FIG. 6.

The fusion gene CLTC-ETV1 is a fusion between clathrin, heavy chain (Hc) ("CLTC") and ets variant 1 ("ETV1"). The human CLTC is typically located on chromosome 17q23.1 and the human ETV1 gene is typically located on chromosome 7p21.3. In certain embodiments, the CLTC gene is the human gene having NCBI Gene ID NO: 1213, sequence chromosome 17; NC_000017.11 (59619689 . . . 59696956) and/or the ETV1gene is the human gene having NCBI Gene ID NO: 2115, sequence chromosome 7; NC_000007.14 (13891229 . . . 13991425, complement). In certain embodiments, the junction and/or junction fragment of a CLTC-ETV1 fusion gene comprises a sequence as shown in FIG. 6 or a fragment thereof.

The fusion gene ACPP-SEC13 is a fusion between acid phosphatase, prostate ("ACPP") and SEC13 homolog ("SEC13"). The human ACPP is typically located on chromosome 3q22.1 and the human SEC13 gene is typically located on chromosome 3p25-p24. In certain embodiments, the ACPP gene is the human gene having NCBI Gene ID NO: 55, sequence chromosome 3; NC_000003.12 (132317367 . . . 132368302) and/or the SEC13 gene is the human gene having NCBI Gene ID NO: 6396, sequence chromosome 3; NC_000003.12 (10300929 . . . 10321188, complement). In certain embodiments, the junction and/or junction fragment of an ACPP-SEC13 fusion gene comprises a sequence as shown in FIG. 6.

The fusion gene DOCK7-OLR1 is a fusion between dedicator of cytokinesis 7 ("DOCK7") and oxidized low density lipoprotein (lectin-like) receptor 1 ("OLR1"). The human DOCK7 is typically located on chromosome 1p31.3 and the human OLR1 gene is typically located on chromosome 12p13.2-p12.3. In certain embodiments, the DOCK7 gene is the human gene having NCBI Gene ID NO: 85440, sequence chromosome 1; NC_000001.11 (62454726 . . . 62688368, complement) and/or the OLR1 gene is the human gene having NCBI Gene ID NO: 4973, sequence chromosome 12; NC_000012.12 (10158300 . . . 10172191, complement). In certain embodiments, the junction and/or junction fragment of a DOCK7-OLR1 fusion gene comprises a sequence as shown in FIG. 6.

The fusion gene PCMTD1-SNTG1 is a fusion between protein-L-isoaspartate (D-aspartate) O-methyltransferase domain containing 1 ("PCMTD1") and syntrophin, gamma 1 ("SNTG1"). The human PCMTD1 is typically located on chromosome 8q11.23 and the human SNTG1 gene is typically located on chromosome 8q11.21. In certain embodiments, the PCMTD1 gene is the human gene having NCBI Gene ID NO: 115294, sequence chromosome 8; NC_000008.11 (51817575 . . . 51899186, complement) and/or the SNTG1gene is the human gene having NCBI Gene ID NO: 54212, sequence chromosome 8; NC_000008.11 (49909789 . . . 50794118). In certain embodiments, the junction and/or junction fragment of a PCMTD1-SNTG1 fusion gene comprises a sequence as shown in FIG. 6.

5.2 Fusion Gene Detection

Any of the foregoing fusion genes described above in section 5.1 may be identified by methods known in the art. The fusion genes may be detected by detecting the fusion gene manifested in DNA, RNA or protein. In certain embodiments, a fusion gene can be detected by determining the presence of a DNA molecule, an RNA molecule or protein that is encoded by the fusion gene. For example, and not by way of limitation, the presence of a fusion gene may be detected by determining the presence of the protein encoded by the fusion gene.

The fusion gene, e.g., MAN2A1-FER, may be detected in a sample of a subject. A "patient" or "subject," as used interchangeably herein, refers to a human or a non-human subject. Non-limiting examples of non-human subjects include non-human primates, dogs, cats, mice, etc. The subject may or may not be previously diagnosed as having cancer.

In certain non-limiting embodiments, a sample includes, but is not limited to, cells in culture, cell supernatants, cell lysates, serum, blood plasma, biological fluid (e.g., blood, plasma, serum, stool, urine, lymphatic fluid, ascites, ductal lavage, saliva and cerebrospinal fluid) and tissue samples. The source of the sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid or interstitial fluid), or cells from the individual, including circulating cancer cells. In certain non-limiting embodiments, the sample is obtained from a cancer. In certain embodiments, the sample may be a "biopsy sample" or "clinical sample," which are samples derived from a subject. In certain embodiments, the one or more fusion genes can be detected in one or more samples obtained from a subject. In certain embodiments, the one or more fusion genes can be detected in one or more cells of a sample obtained from a subject. In certain embodiments, the sample includes one or more prostate cancer cells from a subject. In certain embodiments, the sample is not a prostate cancer sample. In certain embodiments, the sample is not a lung adenocarcinoma, glioblastoma multiforme or hepatocellular carcinoma sample.

In certain non-limiting embodiments, the fusion gene is detected by nucleic acid hybridization analysis, e.g., in situ hybridization. In situ hybridization is a technique that can directly identify a specific sequence of DNA or RNA in a cell or biological sample and enables visual determination of the presence and/or expression of a fusion gene in a tissue sample. In certain non-limiting embodiments, where a fusion gene combines genes not typically present on the same chromosome, in situ hybridization analysis may demonstrate probes binding to the same chromosome. For example, and not by way of limitation, analysis may focus on the chromosome where one gene normally resides and then hybridization analysis may be performed to determine whether the other gene is present on that chromosome as well.

In certain non-limiting embodiments, the fusion gene is detected by fluorescent in situ hybridization (FISH) analysis, where fluorescent probes are used to detect a specific sequence of DNA or RNA in a cell or biological sample.

In certain non-limiting embodiments, the fusion gene is detected by DNA hybridization, such as, but not limited to, Southern blot analysis.

In certain non-limiting embodiments, the fusion gene is detected by RNA hybridization, such as, but not limited to, Northern blot analysis. In certain embodiments, Northern blot analysis can be used for the detection of a fusion gene, where an isolated RNA sample is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography to detect the presence of a fusion gene in the RNA sample.

In certain non-limiting embodiments, the fusion gene is detected by nucleic acid sequencing analysis.

In certain non-limiting embodiments, the fusion gene is detected by probes present on a DNA array, chip or a microarray. For example, and not by way of limitation, oligonucleotides corresponding to one or more fusion genes can be immobilized on a chip which is then hybridized with labeled nucleic acids of a sample obtained from a subject. Positive hybridization signal is obtained with the sample containing the fusion gene transcripts.

In certain non-limiting embodiments, the fusion gene is detected by a method comprising Reverse Transcription Polymerase Chain Reaction ("RT-PCR"). In certain embodiments, the fusion gene is detected by a method comprising RT-PCR using the one or more pairs of primers disclosed herein (see, for example, Table 2).

TABLE 2

Primer sequences for RT-PCR.

| Fusion genes | Sequences |
| --- | --- |
| ACPP-SEC13 | 5'-TCCCATTGACACCTTTCCCAC (SEQ ID NO: 30)/ 5'-TGAGGCTTCCAGGTACAACAG (SEQ ID NO: 31) |
| CLTC-ETV1 | 5'-GCCCAGTTGCAGAAAGGAATG (SEQ ID NO: 32/ 5'-CTTGATTTTCAGTGGCAGGCC (SEQ ID NO: 33) |
| DOCK7-OLR1 | 5'-GACTACGTCTCATGCCTTTCC (SEQ ID NO: 34)/ 5'-TTCTCATCAGGCTGGTCCTTC (SEQ ID NO: 35) |
| PCMTD1-SNTG | 5'-GATGTGGTGGAATATGCCAAGG (SEQ ID NO: 36)/ 5'-AAATCCATGTGCTGTGGCACC (SEQ ID NO: 37) |

TABLE 2-continued

Primer sequences for RT-PCR.

| Fusion genes | Sequences |
| --- | --- |
| ZMPSTE24-ZMYM4 | 5'-CGCAATGAGGAAGAAGGGAAC (SEQ ID NO: 38)/ 5'-CATAAATCTGGAATAGGGCTCAG (SEQ ID NO: 39) |
| TMEM135-CCDC67 | 5'-GAGACCATCTTACTGGAAGTTCC-3' (SEQ ID NO: 58)/ 5'-TGGTACTCTTCCACCTGTTGG-3' (SEQ ID NO: 59) |
| Mtor-TP53BP1 | 5'-TTGGCATGATAGACCAGTCCC-3' (SEQ ID NO: 60)/ 5'-CAGCACCAAGGGAATGTGTAG-3' (SEQ ID NO: 61) |
| TRMT11-GRIK2 | 5'-GCGCTGTCGTGTACCCTTAAC-3' (SEQ ID NO: 62)/ 5'-GGTAAGGGTAGTATTGGGTAGC-3' (SEQ ID NO: 63) |
| CCNH-C5orf30 | 5'-CCAGGGCTGGAATTACTATGG-3' (SEQ ID NO: 64)/ 5'-AAGCACCAGTCTGCACAATCC-3' (SEQ ID NO: 65) |
| SLC45A2-AMACR | 5'-TTGATGTCTGCTCCCATCAGG-3' (SEQ ID NO: 66)/ 5'-TGATATCGTGGCCAGCTAACC-3' (SEQ ID NO: 67) |
| KDM4B-AC011523.2 | 5'-AACACGCCCTACCTGTACTTC-3' (SEQ ID NO: 68)/ 5'-CTGAGCAAAGACAGCAACACC-3' (SEQ ID NO: 69) |
| MAN2A1-FER | 5'-TGGAAGTTCAAGTCAGCGCAG-3' (SEQ ID NO: 70)/ 5'-GCTGTCTTTGTGTGCAAACTCC-3' (SEQ ID NO: 71) |
| LRRC59-FLJ60017 | 5'-GTGACTGCTTGGATGAGAAGC-3' (SEQ ID NO: 72)/ 5'-CCAGCATGCAGCTTTTCTGAG-3' (SEQ ID NO: 73) |
| TMPRSS2-ERG | 5'-AGTAGGCGCGAGCTAAGCAGG-3' (SEQ ID NO: 74)/ 5'-GGGACAGTCTGAATCATGTCC-3' (SEQ ID NO: 75) |
| β-actin | 5'-TCAAGATCATTGCTCCTCCTGAGC-3' (SEQ ID NO: 28)/ 5'-TGCTGTCACCTTCACCGTTCCAGT-3' (SEQ ID NO: 29) |

In certain non-limiting embodiments, the fusion gene is detected by antibody binding analysis such as, but not limited to, Western Blot analysis and immunohistochemistry.

In certain non-limiting embodiments, where a fusion gene combines genes not typically present on the same chromosome, FISH analysis may demonstrate probes binding to the same chromosome. For example, analysis may focus on the chromosome where one gene normally resides and then hybridization analysis may be performed to determine whether the other gene is present on that chromosome as well.

5.3 Cancer Targets

Non-limiting examples of cancers that may be subject to the presently disclosed invention include prostate cancer, breast cancer, liver cancer, hepatocarcinoma, hepatoma, lung cancer, non-small cell lung cancer, cervical cancer, endometrial cancer, pancreatic cancer, ovarian cancer, gastric cancer, thyroid cancer, glioblastoma multiforme, colorectal cancer, sarcoma, diffuse large B-cell lymphoma and esophageal adenocarcinoma. In certain embodiments, the cancer is not prostate cancer. In certain embodiments, the cancer is not lung adenocarcinoma, glioblastoma multiforme or hepatocellular carcinoma. In certain embodiments, the target of treatment is a pre-malignant or neoplastic condition involving lung, cervix, endometrium, pancreas, ovary, stomach, thyroid, glia, intestine, esophagus, muscle or B cells. In certain embodiments, the target of treatment is a cell that carries one or more fusion gene, e.g., MAN2A1-FER.

5.4 Methods of Treatment

The present invention provides methods for treating a subject carrying one or more fusion genes, e.g., a subject having cancer or is suspected of having cancer, or a neoplastic or pre-malignant condition that carries one or more fusion genes (a pre-malignant condition is characterized, inter alia, by the presence of pre-malignant or neoplastic cells). In certain embodiments, the method of treatment includes treating a subject carrying one or more fusion genes to produce an anti-cancer effect, an anti-neoplastic effect and/or an anti-cell proliferative effect. Non-limiting examples of fusion genes are disclosed herein and in section 5.1. In certain embodiments, the fusion gene is MAN2A1-FER. Non-limiting examples of cancers that can be treated using the disclosed methods are provided in section 5.3. In certain embodiments, the cancer is not prostate cancer. In certain embodiments, the cancer is not lung adenocarcinoma, glioblastoma multiforme or hepatocellular carcinoma.

In certain embodiments, the method of treating a subject having cancer comprises determining the presence of one or more fusion genes in a sample obtained from the subject, e.g., a sample from a cancer. Non-limiting examples of the fusion genes include TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. If one or more fusion genes are present in the sample then the subject is treated to produce an anti-cancer effect and/or an anti-neoplastic effect. In certain embodiments, the method can include determining the presence or absence of one or more, two or more, three or more, four or more, five or more, six or more, seven or more, eight or more, nine or more, ten or more, eleven or more, twelve or more, thirteen or more or all fourteen of the fusion genes disclosed herein. For example, and not by way of limitation, the method of treating a subject having cancer comprises determining the presence of a MAN2A1-FER fusion gene in a sample obtained from the subject.

In certain embodiments, the present disclosure provides a method for treating a subject that has a pre-malignant or neoplastic condition. In certain embodiments, a pre-malignant or neoplastic condition is identified by the presence of one or more fusion genes within a sample (or one or more cells) obtained from the subject. In certain embodiments, the method comprises determining the presence of one or more fusion genes in a sample (or in one or more cells of a sample) obtained from a subject, where if one or more fusion genes are detected in the sample then treating the subject to produce an anti-neoplastic effect, e.g., by administering to the subject a therapeutically effective amount of an agent specific for the product of the fusion gene. Non-limiting examples of agents specific for the product of a fusion gene are disclosed throughout herein.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer. Similarly, an "anti-neoplastic effect" refers to one or more of a reduction in aggregate neoplastic cell mass, a reduction in neoplastic cell growth rate, a reduction in neoplasm progression (e.g., progressive de-differentiation or epithelial to mesenchymal transition), a reduction in neoplastic cell proliferation, a reduction in neoplasm mass, a reduction in neoplasm volume, and/or a reduction in neoplasm growth rate.

In certain embodiments, the method of treating a subject, e.g., a subject having cancer that carries a fusion gene or a subject that has one or more cells that comprise a fusion gene, comprises determining the presence of one or more fusion genes in a sample obtained from a subject, where if one or more fusion genes are detected in the sample then administering to the subject a therapeutically effective amount of an inhibitor, e.g., an inhibitor specific for the product of the fusion gene. In certain embodiments, the inhibitor can be administered to produce an anti-cancer effect in a subject. For example, and not by way of limitation, the present invention provides a method of treating a subject that comprises determining the presence of a MAN2A1-FER fusion gene in a sample obtained from a subject, and where the MAN2A1-FER fusion gene is detected in the sample then administering to the subject a therapeutically effective amount of an inhibitor, e.g., an inhibitor specific for the product of the MAN2A1-FER fusion gene.

A "therapeutically effective amount" refers to an amount that is able to achieve one or more of the following: an anti-cancer effect, an anti-neoplastic effect, a prolongation of survival and/or prolongation of period until relapse.

In certain embodiments, the method of treating a subject is directed to inhibiting the fusion gene and/or inhibiting the fusion gene product, e.g., the protein and/or RNA encoded by the fusion gene. For example, and not by way of limitation, a method of treating a subject of the present invention is directed to inhibiting the MAN2A1-FER fusion gene and/or inhibiting the MAN2A1-FER fusion gene product, e.g., the protein and/or RNA encoded by the MAN2A1-FER fusion gene.

The present invention further provides a method of preventing, minimizing and/or reducing the growth of a tumor comprising determining the presence of one or more fusion genes in a sample of the subject, where if one or more fusion genes are present in the sample then administering to the subject a therapeutically effective amount of an agent specific for the product of the fusion gene to prevent, minimize and/or reduce the growth of the tumor.

The present invention provides a method of preventing, minimizing and/or reducing the growth and/or proliferation of a cancer cell comprising determining the presence of one or more fusion genes in a sample of the subject, where if one or more fusion genes are present in the sample then administering to the subject a therapeutically effective amount of an agent specific for the product of the fusion gene to prevent, minimize and/or reduce the growth and/or proliferation of the cancer cell.

In certain non-limiting embodiments, the present invention provides for methods of treating and/or inhibiting the progression of cancer and/or tumor and/or neoplastic growth in a subject comprising determining the presence of one or more fusion genes in a sample of the subject, where if one or more fusion genes are present in the sample then administering to the subject a therapeutically effective amount of an agent specific for the product of the fusion gene to treat and/or inhibit the progression of the cancer and/or the tumor.

In certain embodiments, the present invention provides a method for lengthening the period of survival of a subject having a cancer. In certain embodiments, the method comprises determining the presence of one or more fusion genes in a sample of the subject, where if one or more fusion genes are detected in the sample then administering to the subject a therapeutically effective amount of an inhibitor, e.g., an inhibitor specific for the product of the fusion gene. In certain embodiments, the period of survival of a subject having cancer can be lengthened by about 1 month, about 2 months, about 4 months, about 6 months, about 8 months, about 10 months, about 12 months, about 14 months, about 18 months, about 20 months, about 2 years, about 3 years, about 5 years or more using the disclosed methods.

The present invention further provides methods for determining a treatment for a subject having one or more cells that contains one or more fusion genes. In certain embodiments, the method includes: i) providing a sample from the subject; ii) determining whether one or more cells of the subject contains one or more fusion genes selected from the group consisting of TMEM135-CCDC67, TRMT11-GRIK2, SLC45A2-AMACR, MTOR-TP53BP1, LRRC59-FLJ60017, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 and a combination thereof; and iii) if the one or more fusion genes are detected in the one or more cells of the subject, then instructing the administration of a therapeutically effective amount of one or more inhibitors specific to the one or more fusion genes detected, wherein the subject does not have prostate cancer.

The present invention further provides methods of identifying a subject at risk of developing cancer. In certain embodiments, the method comprises determining whether one or more cells obtained from a subject contain one or more fusion genes, where if the one or more one or more cells contain one or more fusion genes, then the subject is at risk of developing cancer, wherein the cancer is not prostate cancer.

The present invention further provides methods of diagnosing a subject with a pre-malignant condition. In certain embodiments, the method comprises determining whether one or more cells obtained from the subject contain one or more fusion genes, where if the one or more one or more cells contain one or more fusion genes, then the subject has a pre-malignant condition, wherein the subject does not prostate cancer.

In certain embodiments, the fusion gene in a sample is detected by genome sequencing. In certain embodiments, the fusion gene in a sample is detected by RNA sequencing. For example, and not by way of limitation, RNA sequencing can be performed using the primers disclosed herein. In certain embodiments, the fusion gene in a sample is detected by FISH.

Examples of inhibitors include, but are not limited to, compounds, molecules, chemicals, polypeptides and proteins that inhibit and/or reduce the expression and/or activity of the protein encoded by a fusion gene. Alternatively or additionally, the inhibitor can include compounds, molecules, chemicals, polypeptides and proteins that inhibit and/or reduce the expression, e.g., RNA expression or protein expression, and/or activity of one or more downstream targets of the fusion gene. Additional non-limiting examples of inhibitors include ribozymes, antisense oligonucleotides, shRNA molecules and siRNA molecules that specifically inhibit or reduce the expression and/or activity of the fusion gene and/or inhibit or reduce the expression and/or activity of one or more downstream targets of the fusion gene. One non-limiting example of an inhibitor comprises an antisense, shRNA or siRNA nucleic acid sequence homologous to at least a portion of the fusion gene sequence, wherein the homology of the portion relative to the fusion gene sequence is at least about 75 or at least about 80 or at least about 85 or at least about 90 or at least about 95 or at least about 98 percent, where percent homology can be determined by, for example, BLAST or FASTA software. In certain embodiments, the antisense, the shRNA or siRNA nucleic acid sequence can be homologous to the sequence at the "junction fragment" that encompasses the boundary between the spliced genes of the fusion gene, also referred to herein as the chromosomal breakpoint. Non-limiting examples of siRNAs homologous to the junction fragment sequences of the disclosed fusion genes are shown in Table 1 Non-limiting examples of chromosomal breakpoints that can be targeted are disclosed in Table 1 and FIGS. 1-3, 6 and 13. In certain embodiments, the inhibitor is an siRNA homologous to the junction fragment sequence of MAN2A1-FER. In certain embodiments, the antisense, shRNA or siRNA nucleic acid sequence can comprise a sequence that is homologous to a portion of the junction fragment.

In certain non-limiting embodiments, the complementary portion of the antisense nucleic acid, shRNA or siRNA molecules may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA or siRNA molecules may comprise DNA or atypical or non-naturally occurring residues, for example, but not limited to, phosphorothioate residues and locked nucleic acids.

In certain embodiments, an inhibitor can include an antibody, or a derivative thereof, that specifically binds to and inhibits and/or reduces the expression and/or activity of the protein that is encoded by the fusion gene, e.g., an antagonistic antibody. Alternatively or additionally, an inhibitor can include an antibody, or derivative thereof, that specifically binds to and inhibits and/or reduces the expression and/or activity of one or more downstream targets of the fusion gene. The phrase "specifically binds" refers to binding of, for example, an antibody to an epitope or antigen or antigenic determinant in such a manner that binding can be displaced or competed with a second preparation of identical or similar epitope, antigen or antigenic determinant. Non-limiting examples of antibodies, and derivatives thereof, that can be used in the disclosed methods include polyclonal or monoclonal antibodies, chimeric, human, humanized, primatized (CDR-grafted), veneered or single-chain antibodies, phage produced antibodies (e.g., from phage display libraries), as well as functional binding fragments of antibodies.

Antibody binding fragments, or portions thereof, include, but are not limited to, Fv, Fab, Fab' and F(ab')$_2$. Such fragments can be produced by enzymatic cleavage or by recombinant techniques. In certain embodiments, the inhibitor can be antibody, or a derivative thereof, that specifically binds to and inhibits and/or reduces the expression and/or activity of the protein that is encoded by the MAN2A1-FER fusion gene or binds to and inhibits and/or reduces the expression and/or activity of one or more downstream targets of the MAN2A1-FER fusion gene. For example, and not by way of limitation, an inhibitor, e.g., an antibody, or a derivative thereof, for the MAN2A1-FER fusion gene can target a downstream target of MAN2A1, FER and/or MAN2A1-FER. For example, and not by way of limitation, the inhibitor can inhibit and/or reduce the expression and/or activity of EGFR, B-raf, MEK and/or AKT.

In certain embodiments, where the protein encoded by the fusion gene detected in the sample of the subject exhibits kinase activity, the method of treating a subject, e.g., a subject having cancer that carries the fusion gene, can include administering a therapeutically effective amount of an inhibitor to the subject that inhibits and/or reduces the kinase activity of the protein encoded by the fusion gene, i.e., a kinase inhibitor. Non-limiting examples of kinase inhibitors include afatinib, alectinib, axitinib, bevacizumab, bosutinib, cetuximab, crizotinib, canertinib, dasatinib, erlotinib, fostamatinib, gefitinib, GSK1838705A, ibrutinib, imatinib, lapatinib, lenvatinib, mubritinib, nilotinib, panitumumab, pazopanib, pegaptanib, ranibizumab, ruxolitinib, sorafenib, sunitinib, su6656, trastuzumab, tofacitinib, vandetanib and vemurafenib. For example, and not by way of limitation, if the protein encoded by the fusion gene detected in a sample of the subject exhibits tyrosine kinase activity, a therapeutically effective amount of a tyrosine kinase inhibitor can be administered to the subject.

In certain embodiments, a method of treating a subject, e.g., a subject having cancer (e.g., not prostate cancer), can comprise determining the presence of MAN2A1-FER in a sample of the subject, where if the MAN2A1-FER fusion gene is present in the sample, then treating the subject with a therapeutically effective amount of a FER inhibitor. Non-limiting examples of FER inhibitors include crizotinib, TAE684, WZ-4-49-8, WZ-4-49-10 and WZ-4-24-7. In particular non-limiting embodiments, the FER inhibitor can be derived from diaminopyrimidine or pyrazologyrididine compounds. Further non-limiting examples of FER inhibitors are disclosed in PCT Application No. WO 2009/019708, the contents of which is hereby incorporated by reference in its entirety. In certain embodiments, the FER inhibitor can include tyrosine kinase inhibitors and ALK inhibitors as FER exhibits high sequence similarity to ALK. In certain embodiments, the FER inhibitor is an antibody that reduces and/or inhibits the expression and/or activity of the MAN2A1-FER protein. In certain embodiments, the FER inhibitor comprises an siRNA targeting the MAN2A1-FER fusion gene or the juncture sequence of the MAN2A1-FER fusion gene. A non-limiting example of an siRNA sequence targeting the MAN2A1-FER fusion gene is shown in Table 1. In certain embodiments, a chromosomal breakpoint of a MAN2A1-FER fusion gene that can be targeted using the disclosed methods is shown in Table 1 and FIGS. 1 and 13.

Alternatively or additionally, the method of treating a subject expressing the MAN2A1-FER fusion gene, e.g., a subject that has a cancer that carries the MAN2A1-FER fusion gene, can comprise administering to the subject a compound that reduces and/or inhibits the activity and/or expression of one or more downstream targets of the MAN2A1-FER fusion gene. For example, and not by way of limitation, the method can include the inhibition of the EGFR-RAS-BRAF-MEK signaling pathway. Non-limiting examples of compounds that inhibit EGFR activity include erlotinib, cetuximab, gefitinib, bevacizumab, canertinib, panitumumab and bortezomib. Additional non-limiting examples of EGFR inhibitors are disclosed in Dziadziuszko and Jassem, Annals of Oncology 23(Suppl._10):193-196 (2012). A non-limiting example of a compound that inhibits B-raf activity is RAF265. Non-limiting examples of compounds that inhibit MEK activity include binimetinib, vemurafenib, PD-325901, selumetinib and trametinib. Non-limiting examples of AKT inhibitors are disclosed in Nitulescu et al., Int J Oncol. 48(3):869-885 (2016) (see Table 1 of Nitulescu et al. (2016)). Additional non-limiting examples of compounds that inhibit the EGFR-RAS-BRAF-MEK signaling pathway include TAK-733, Honokiol, AZD8330, PD318088, BIX 02188, pimasertib, SL-327, BIX 02189, PD98059, MEK162, PD184352 and U0126-EtOH.

In certain embodiments, the method can include administering to the subject a compound that reduces and/or inhibits the activity of and/or expression of the first protein of the fusion gene, in combination with a compound that reduces and/or inhibits the activity and/or expression of the second protein of the fusion gene. For example, in certain embodiments, the method of treating a subject expressing the MAN2A1-FER fusion gene, e.g., a subject that has a cancer that carries the MAN2A1-FER fusion gene, can comprise administering to the subject a compound that reduces and/or inhibits the activity of and/or expression of FER, e.g., a FER inhibitor, in combination with a compound that reduces and/or inhibits the activity and/or expression of one or more downstream targets of the MAN2A1-FER fusion gene. In certain embodiments, being used in combination does not require that the FER inhibitor and compound that reduces and/or inhibits the activity and/or expression of one or more downstream targets of the MAN2A1-FER fusion gene are physically combined prior to administration or that they be administered over the same time frame. Accordingly, a compound that reduces and/or inhibits the activity and/or expression of one or more downstream targets of the MAN2A1-FER fusion gene may be administered prior to, concurrently with, or subsequent to, administration of one or more doses of a FER inhibitor. For example, and not by way of limitation, method of treating a subject expressing the MAN2A1-FER fusion gene can comprise administering to the subject a therapeutically effective amount of crizotinib and a therapeutically effective amount of canertinib.

In certain embodiments, a method of treating a subject, e.g., a subject having a cancer or having a pre-malignant or neoplastic condition, that carries a fusion gene can comprise determining the presence of SLC45A2-AMACR in a sample of the subject, where if the SLC45A2-AMACR fusion gene is present in the sample, then treating the subject with a therapeutically effective amount of a racemase inhibitor and/or an AMACR inhibitor. A non-limiting example of a racemase and/or AMACR inhibitors includes ebselen, 2-(2, 5-dihydroxy-4-methylphenyl)-5-methyl benzene-1.4-diol (DMPMB), 2-methylsulfanyl-7,9-dihydro-3H-purine-6,8-dithione (MSDTP), 2,5-di(pyrazol-1-yl)benzene-1,4-diol (DPZBD), Rose Bengal, Congo Red, 3,5-di(pyridin-4-yl)-1,2,4-thiadiazole (DPTD), ebselen oxide and 3,7,12-trihydroxycholestanoyl Coenzyme A (THCA-CoA). In particular non-limiting embodiments, the racemase inhibitor can be a N-methylthiocarbamate. Further non-limiting examples of AMACR inhibitors are disclosed in Wilson et al., Mol. Cancer Ther. (2011), 10(5): 825-838, the content of which is hereby incorporated by reference in its entirety.

In certain embodiments, the method of treating a subject, e.g., a subject that has a cancer that carries a fusion gene disclosed herein, e.g., the MAN2A1-FER fusion gene, can further comprise administering a therapeutically effective amount of an anti-cancer agent or agent that results in an anti-neoplastic effect. An "anti-cancer agent" can be any molecule, compound chemical or composition that has an anti-cancer effect. Anti-cancer agents include, but are not limited to, chemotherapeutic agents, radiotherapeutic agents, cytokines, anti-angiogenic agents, apoptosis-inducing agents or anti-cancer immunotoxins. In certain non-limiting embodiments, an inhibitor, disclosed herein, can be administered in combination with one or more anti-cancer agents. "In combination with," as used herein, means that the one or more inhibitor compounds and/or agents administered to a subject and the one or more anti-cancer agents are administered to a subject as part of a treatment regimen or plan. This term does not require that the inhibitor and/or kinase inhibitor and one or more anti-cancer agents are physically combined prior to administration nor that they be administered over the same time frame. Additional non-limiting examples of anti-cancer agents include Abiraterone Acetate, Bicalutamide, Cabazitaxel, Casodex (Bicalutamide), Degarelix, Docetaxel, Enzalutamide, Goserelin Acetate, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Mitoxantrone Hydrochloride, Prednisone, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide), Zoladex (Goserelin Acetate) and Zytiga (Abiraterone Acetate).

In certain embodiments, the method of treating a subject, e.g., a subject that has a cancer that carries one or more fusion genes, e.g., the MAN2A1-FER fusion gene, comprises determining the presence of one or more fusion genes in a sample of the subject, where if one or more fusion genes are detected in the sample then performing one or more of cryotherapy, radiation therapy, chemotherapy, hormone therapy, biologic therapy, bisphosphonate therapy, high-intensity focused ultrasound, frequent monitoring, frequent prostate-specific antigen (PSA) checks and radical prostatectomy. A non-limiting example of a biologic therapeutic is Sipuleucel-T. Bisphosphonate therapy includes, but is not limited to, clodronate or zoledronate. In certain embodiments, these methods can be used to produce an anti-cancer effect in a subject. In certain embodiments, the sample is not a prostate cancer sample.

Hormone therapy can include one or more of orchiectomy, the administration of luteinizing hormone-releasing hormone (LHRH) analogs and/or agonists, LHRH antagonists, anti-androgens or androgen-suppressing drugs, estrogen, anti-estrogens, progestins, gonadotropin-releasing hormone (GnRH) analogues and aromatase inhibitors. Non-limiting examples of LHRH analogs and/or agonists include leuprolide, goserelin and buserelin. Non-limiting examples of LHRH antagonists include abarelix, cetrorelix, ganirelix and degarelix. Anti-androgen drugs include, but are not limited to, flutamide, bicalutamide, enzalutamide and nilutamide. Non-limiting examples of androgen-suppressing drugs include estrogens, ketoconazole and aminoglutethimide. Frequent monitoring can include PSA blood tests, digital rectal exams, ultrasounds and/or transrectal ultrasound-guided prostate biopsies at regular intervals, e.g., at about 3 to about 6 month intervals, to monitor the status of the prostate cancer. Radical prostatectomy is a surgical procedure that involves the removal of the entire prostate gland and some surrounding tissue. Prostatectomies can be performed by open surgery or it may be performed by laparoscopic surgery.

TABLE 1

Fusion gene junction sequences and siRNA sequences targeting the fusion gene junctions.

MAN2A1-FER

```
                    MAN2A1                          FER
GCAAATACTATTTCAGAAACAGCCTATGAGGGAAATTTTGGTGAAGTATATAAGGGCACA
(SEQ ID NO: 1)

siRNA sequence for MAN2A-FER
Sense Strand:      5'RCrArGrCrCrUrArUrGrArGrGrGrArArArUrUrUrUrGrGrUGA
                      (SEQ ID NO: 2)
Antisense Strand: 5'RUrCrArCrCrArArArArUrUrUrCrCrCrUrCrArUrArGrGrCrUrGrUrU
                      (SEQ ID NO: 3)
```

SLC45A2-AMACR

```
                 SLC45A2                      AMACR
TCCACTACCATGCCCTCTTCACAGGTGTCATGGAGAAACTCCAGCTGGGCCCAGAGA
(SEQ ID NO: 4)

siRNA sequence for SLC45A2-AMACR:
Sense Strand:     5' RUrGrCrCrCrUrCrUrUrCrArCrArGrGrUrGrUrCrArUrGrAG
                     (SEQ ID NO: 5)
Antisense Strand: 5' RCrUrCrCrArUrGrArCrArCrCrUrGrUrGrArArGrArGrGrGrCrArUrG
                     (SEQ ID NO: 6)
```

MTOR-TP53BP1

```
                 MTOR                         TP53BP1
TGTCAGAATCCAAGTCAAGTCAGGATTCCTTGTTCTGGGAATGTCAGTGGAATCTGCTCCTGC
(SEQ ID NO: 7)

siRNA sequence for MTOR-TP53BP1:
Sense Strand:     5' RGrUrCrArGrGrArUrCrCrUrUrGrUrUrCrUrGrGrGrArATG
                     (SEQ ID NO: 8)
Antisense Strand: 5' RCrArUrUrCrCrCrArGrArArCrArArGrGrArArUrCrCrUrGrArCrUrU
                     (SEQ ID NO: 9)
```

TABLE 1-continued

Fusion gene junction sequences and siRNA sequences targeting the fusion gene junctions.

TMEM135-CCDC67

```
        TMEM135              CCDC67
TTTTAAGACTCACCAAGGGCAAATAAGAAGCCAACTCCAACAGGTGGAAGAGTACCA
(SEQ ID NO: 10)

siRNA sequence for TMEM135-CCDC67:
Sense Strand:     5' RGrArCrUrCrArCrCrArArGrGrGrCrArArArUrArArGrArAGC
                  (SEQ ID NO: 11)
Antisense Strand: 5' RGrCrUrUrCrUrUrArUrUrUrGrCrCrCrUrUrGrGrUrGrArGrUrU
                  (SEQ ID NO: 12)
```

CCNH-C5orf30

```
             CCNH          C5ORF30
TGTCACAGTTACTAGATATAATGAAAATACCTGGAGTAGAACAGAAAAATTATTATGTCT
(SEQ ID NO: 13)

siRNA sequence for CCNH-C5orf30:
Sense Strand:     5' RArUrGrArArArUrArCrCrUrGrGrArGrUrArGrArArCrAGA
                  (SEQ ID NO: 14)
Antisense Strand: 5' RUrCrUrGrUrUrCrUrArCrUrCrCrArGrGrUrArUrUrUrCrArUrUrA
                  (SEQ ID NO: 15)
```

KDM4B-AC011523.2

```
        KDM4B                  AC011523.2
AACTACCTGCACTTTGGGGAGCCTAAGTCCTGGACAGTAAGCAAGCCTGGATCTGAGAGA
(SEQ ID NO: 16)

siRNA sequence for KDM4-AC011523.2
Sense Strand:     5' RGrArGrCrCrUrArArGrUrCrCrUrGrGrArCrArGrUrArArGCA
                  (SEQ ID NO: 17)
Antisense Strand: 5' RUrGrCrUrUrArCrUrGrUrCrCrArGrGrArCrUrUrArGrGrCrUrCrCrC
                  (SEQ ID NO: 18)
```

TRMT11-GRIK2

```
          TRMT11                GRIK2
AGCATCTGGAGTTCCGCCTGCCGGTGGTATTTTTGAATATGTGGAATCTGGCCCAATGGGAGCTG
(SEQ ID NO: 19)

siRNA sequence for TRMT11-GRIK2:
Sense Strand:     5' RCrCrGrCrCrUrGrCrCrGrGrUrGrGrUrArUrUrUrUrUrGrAAT
                  (SEQ ID NO: 20)
Antisense Strand: 5' RArUrUrCrArArArArUrArCrCrArCrCrGrGrCrArGrGrCrGrGrArA
                  (SEQ ID NO: 21)
```

L44C59-FLJ60017

```
         LRRC69                FLJ60017
CTGCTTGGATGAGAAGCAGTGTAAGCAGTGTGCAAACAAGGTGACTGGAAGCACCTGCTCAATGGCTG
(SEQ ID NO: 22)

siRNA sequence for LRRC59-FLJ60017:
Sense Strand:     5' RArCrArArGrGrUrGrArCrUrGrGrArArGrCrArCrCrUrGrCTC
                  (SEQ ID NO: 23)
Antisense Strand: 5' RGrArGrCrArGrGrUrGrCrUrUrCrCrArGrUrCrArCrCrUrUrGrUrUrU
                  (SEQ ID NO: 24)
```

PTEN-NOLC1

```
           PTEN                 NOLC1
AAGCCAACCGATACTTTTCTCCAAATTTTAAGACACAGCAGGATGCCAATGCCTCTTCCCTCTTAGAC
(SEQ ID NO: 25)

siRNA sequence for PTEN-NOLC1:
Sense Strand:     5' RCrUrCrCrArArArUrUrUrUrArArGrArCrArCrArGrCrArGGA
                  (SEQ ID NO: 26)
Antisense Strand: 5' RUrCrCrUrGrCrUrGrUrGrUrCrUrUrArArArArUrUrUrGrGrArGrArA
                  (SEQ ID NO: 27)
```

The head gene is indicated by italic font. Targeted sequences are underlined and bolded.

5.6 Pharmaceutical Formulations

In certain non-limiting embodiments, the present invention provides for pharmaceutical formulations of the inhibitors and/or agents disclosed above for therapeutic use. In certain embodiments, a pharmaceutical formulation comprises one or more agents specific for a product of a fusion gene and a pharmaceutically acceptable carrier. For example, and not by way of limitation, the pharmaceutical formulation comprises a FER and/or EGFR inhibitor and a pharmaceutically acceptable carrier, e.g., for use in treating a subject that has a cancer that carries the MAN2A1-FER fusion gene. In certain embodiments, the cancer is not prostate cancer. Non-limiting examples of agents and/or inhibitors are disclosed in section 5.5 above.

"Pharmaceutically acceptable carrier," as used herein, includes any carrier which does not interfere with the effectiveness of the biological activity of the active ingredients, e.g., inhibitors, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioabsorbable matrix materials, implantation elements containing the inhibitor and/or any other suitable vehicle, delivery or dispensing means or material. Such carriers can be formulated by conventional methods and can be administered to the subject. In certain embodiments, the pharmaceutical acceptable carrier can include buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, a suitable pharmaceutically acceptable carrier can include one or more of water, saline, phosphate buffered saline, dextrose, glycerol, ethanol or combinations thereof.

In certain embodiments, the methods and formulations of the present invention can be used for reducing, inhibiting, preventing or reversing cancer and/or tumor growth. Standard methods for intracellular delivery can be used (e.g., delivery via liposome). Such methods are well known to those of ordinary skill in the art. Therapeutic administration of an inhibitor intracellularly can also be accomplished using gene therapy, e.g., by using shRNAs. The route of administration eventually chosen will depend upon a number of factors and can be ascertained by one skilled in the art.

In certain non-limiting embodiments, the pharmaceutical formulations of the present invention can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral or nasal ingestion by a patient to be treated. In certain embodiments, the pharmaceutical formulation can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion.

In certain embodiments, the pharmaceutical formulations of the present invention can be formulated using pharmaceutically acceptable carriers well known in the art that are suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. For example, and not by way of limitation, formulations of the present invention can be administered to the patient intravenously in a pharmaceutically acceptable carrier such as physiological saline. In certain embodiments, the present invention provides a parenteral formulation comprising a FER and/or EGFR inhibitor.

In certain embodiments, the pharmaceutical formulations suitable for use in the present invention can include formulations where the active ingredients, e.g., FER and/or EGFR inhibitors, are contained in a therapeutically effective amount. The therapeutically effective amount of an active ingredient can vary depending on the active ingredient, e.g., FER and/or EGFR inhibitors, formulation used, the cancer and its severity, and the age, weight, etc., of the subject to be treated. In certain embodiments, a patient can receive a therapeutically effective amount of an inhibitor and/or agent disclosed herein in single or multiple administrations of one or more formulations, which can depend on the dosage and frequency as required and tolerated by the patient.

In certain non-limiting embodiments, the inhibitors and/or agents described above can be used alone or in combination with one or more anti-cancer agents. As noted above, "in combination with" means that an inhibitor and the one or more anti-cancer agents are administered to a subject as part of a treatment regimen or plan. In certain embodiments, being used in combination does not require that the inhibitor and the one or more anti-cancer agents are physically combined prior to administration or that they be administered over the same time frame. Accordingly, a second anti-cancer agent may be administered prior to, concurrently with, or subsequent to, administration of one or more doses of an inhibitor.

In certain non-limiting embodiments, an FER inhibitor can be used in combination with a EGFR inhibitor. For example, and not by way of limitation, a pharmaceutical formulation of the present invention can include one or more FER and/or one or more EGFR inhibitors. For example, and not by way of limitation, a pharmaceutical formulation of the present invention can include a therapeutically effective amount of one or more FER inhibitors and a therapeutically effective amount of one or more EGFR inhibitors. In certain embodiments, the FER inhibitor is crizotinib. In certain embodiments, the EGFR inhibitor is canertinib. In certain embodiments, a pharmaceutical formulation of the present invention can include crizotinib and canertinib.

In certain embodiments, where an inhibitor is used in combination with an anti-cancer agent, the amount of each may in some instances be less than a therapeutically effective amount for that agent taken singly, but when both are used therapeutically effectiveness is achieved.

5.7 Kits

The present invention further provides kits for detecting one or more fusion genes disclosed herein and/or for carrying out any one of the above-listed detection and therapeutic methods.

Types of kits include, but are not limited to, packaged fusion gene-specific probe and primer sets (e.g., TaqMan probe/primer sets), arrays/microarrays, antibodies, which further contain one or more probes, primers, or other reagents for detecting one or more fusion genes of the present invention, e.g., in one or more cells, e.g., cancer cells, of a subject. In certain embodiments, the one or more cancer cells are not prostate cancer cells. In certain embodiments, the one or more cancer cells are not lung adenocarcinoma, glioblastoma multiforme or hepatocellular carcinoma cells.

In certain non-limiting embodiments, a kit is provided comprising one or more nucleic acid primers or probes and/or antibody probes for use in carrying out any of the above-listed methods. Said probes may be detectably labeled, for example with a biotin, colorimetric, fluorescent or radioactive marker. A nucleic acid primer may be provided as part of a pair, for example for use in polymerase chain reaction. In certain non-limiting embodiments, a nucleic acid primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length. An nucleic acid probe may be an oligonucleotide probe and/or a probe suitable for FISH analysis. In specific non-limiting embodiments, the kit comprises primers and/or probes for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, a kit of the present invention can include primers and/or probes for determining the presence of MAN2A1-FER in a sample of a subject, e.g., in one or more cancer cells from the subject. In certain embodiments, the one or more cancer cells are not prostate cancer cells. In certain embodiments, the one or more cancer cells are not lung adenocarcinoma, glioblastoma multiforme or hepatocellular carcinoma cancer cells.

In certain non-limiting embodiments, the nucleic acid primers and/or probes may be immobilized on a solid surface, substrate or support, for example, on a nucleic acid microarray, wherein the position of each primer and/or probe bound to the solid surface or support is known and identifiable. The nucleic acid primers and/or probes can be affixed to a substrate, such as glass, plastic, paper, nylon or other type of membrane, filter, chip, bead, or any other suitable solid support. The nucleic acid primers and/or probes can be synthesized directly on the substrate, or synthesized separate from the substrate and then affixed to the substrate. The arrays can be prepared using known methods.

In non-limiting embodiments, a kit provides nucleic acid probes for FISH analysis of one or more fusion genes, e.g., selected from the group consisting of: TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, a kit of the present invention comprises nucleic acid probes for FISH analysis of the MAN2A1-FER fusion gene. In specific non-limiting embodiments, probes to detect a fusion gene may be provided such that separate probes each bind to the two components of the fusion gene or a probe may bind to a "junction fragment" that encompasses the boundary between the spliced genes. In specific non-limiting embodiments, the kit comprises said probes for analysis of at least two, at least three, at least four, at least five, six, seven, eight, nine, ten, eleven, twelve, thirteen or all fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, a kit of the present invention comprises nucleic acid probes for FISH analysis of the MAN2A1-FER fusion gene, which bind to a "junction fragment" of the MAN2A1-FER fusion gene, or comprises one nucleic acid probe that binds to the MAN2A1 gene and a second nucleic acid probe that binds to the FER gene.

In non-limiting embodiments, a kit provides nucleic acid primers for PCR analysis of one or more fusion gene, e.g., selected from the group consisting of: TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In specific non-limiting embodiments, the kit comprises said primers for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, a kit of the present invention comprises nucleic acid primers for PCR analysis of the MAN2A1-FER fusion gene.

In certain embodiments, a kit provides a pharmaceutical composition disclosed herein, e.g., as disclosed in section 5.6. For example, and not by way of limitation, a kit can comprise a pharmaceutical composition that includes an agent and/or inhibitor that is specific for the product of the fusion gene. In certain embodiments, the kit can comprise a pharmaceutical composition that includes a FER and/or an EGFR inhibitor and a pharmaceutically acceptable carrier, e.g., for use in treating a subject that has one or more cells that carry the MAN2A1-FER fusion gene. In certain embodiments, the kit can comprise crizotinib and canertinib in the same or different containers. In certain non-limiting embodiments, the kit can further comprise one or more nucleic acid primers or probes and/or antibody probes for detecting one or more fusion genes, as disclosed above.

6. EXAMPLE 1: ONCOGENIC ACTIVITY OF MAN2A1-FER IN HUMAN MALIGNANCIES

6.1 Introduction

The following Example is offered to more fully illustrate the disclosure, but is not to be construed as limiting the scope thereof.

Oncogenic fusion genes are one of the fundamental mechanisms driving the progression of human cancers. One of the fusion genes is a fusion between exon 13 of the 5' end of mannosidase alpha class 2A member 1 (MAN2A1) and the last 6 exons of the 3' end of FER tyrosine kinase (FER). MAN2A1 is a Golgi enzyme required for conversion of high mannose to complex type structure of N-glycan for mature glycosylation of a membrane protein (Moremen and Robbins (1991) J Cell Biol 115:1521-1534; Misago et al. (1995) Proc Natl Acad Sci USA 92:11766-11770). Little is known about its relation with human malignancies. On the other hand, FER, a tyrosine kinase, is a well-documented oncogene (Hao et al. (1989) Mol Cell Biol 9:1587-1593). The chimeric MAN2A1-FER protein contains 703 amino acids from the N-terminus of MAN2A1 and 251 amino acids from the C-terminus of FER. The resulting chimera protein loses the glycoside-hydrolase domain in the C-terminus of MAN2A1 and the SH2 domain from the N-terminus of FER, while leaving the tyrosine kinase domain in FER largely intact. Previous analysis showed that about 80% of patients with MAN2A1-FER-positive prostate cancer experiences poor clinical outcomes. However, prior to the present studies it was unclear whether MAN2A1-FER fusion also occurs in other types of human malignancies.

In this Example, we show that the MAN2A1-FER fusion gene occurs in multiple types of human malignancies. In particular, MAN2A1-FER was found in prostate cancer, liver cancer, non-small cell lung cancer, glioblastoma multiforme, ovarian cancer and esophageal adenocarcinoma. The expression of the MAN2A1-FER protein leads to carcinogenesis in vitro and in vivo, and the treatment of cancers positive for MAN2A1-FER with tyrosine kinase inhibitors led to dramatic improvement of survival of animals xenografted with cancers positive for the fusion gene. The FER domain of the MAN2A1-FER fusion translocates from cytoplasm to Golgi apparatus and leads to the phosphorylation of the N-terminus of EGFR and activation of EGFR signaling pathway. Expression of MAN2A1-FER generated a dramatic increase in the growth and invasion of cancers in vitro and in vivo, while removal of the fusion through knockout generated significant lower level of growth and metastasis. The presence of MAN2A1-FER increased the sensitivity of human cancers to FER kinase inhibitor crizotinib or EGFR kinase inhibitor canertinib both in vitro and in vivo. Hydrodynamic tail-vein injection of MAN2A1-FER gene resulted in liver cancer in mice with somatic Pten deletion. Taken together, these results show that MAN2A1-FER fusion gene is one of key drivers for human cancer development.

6.2 Materials and Methods

Cell Lines.

All cell lines, including PC3 (prostate cancer), Du145 (prostate cancer), H23, HUH7 and HEP3B were purchased from American Type Cell Culture (Manassas, Va.). PC3 cells were cultured with F12K medium supplemented with 10% fetal bovine serum (InVitrogen, Carlsbad, Calif.). DU145 and HEP3B cells were cultured with modified Eagle medium supplemented with 10% fetal bovine serum (InVitrogen). A-172, NIH3T3 and HUH7 cells were cultured with Dulbecco's modified eagle medium supplemental with 10% fetal bovine serum. H23 cells were cultured with RPMI1640 medium supplemented with 10% fetal bovine serum. The genomes of these cell lines were tested for a short tandem repeat (STR) DNA profile on eight different loci (CSF1PO, D13S317, D16S539, D5S818, D7S820, THO1, TPDX, and vWA) of the genomes by PCR using the following sets of primers:

```
CSF1PO:
                                     (SEQ ID NO: 76)
AACCTGAGTCTGCCAAGGACTAGC/

(SEQ ID NO: 77)
TTCCACACACCACTGGC CATCTTC,

D13S317:
                                     (SEQ ID NO: 78)
ACAGAAGTCTGGGATGTGGA/

(SEQ ID NO: 79)
GCCCAAAAAGACAGACAGAA,

D16S539:
                                     (SEQ ID NO: 80)
GATCCCAAGCTCTTCCTCTT/

(SEQ ID NO: 81)
ACGTTTGTGTGTGCATCTGT,

D5S818:
                                     (SEQ ID NO: 82)
GGGTGATTTTCCTCTTTGGT/

(SEQ ID NO: 83)
TGATTCCAATCATAGCCACA,

D7S820:
                                     (SEQ ID NO: 84)
TGTCATAGTTTAGAACGAACTAACG/

(SEQ ID NO: 85)
CTGAGGTATCAAAAACTCAGAGG,

TH01:
                                     (SEQ ID NO: 86)
GTGGGCTGAAAAGCTCCCGATTAT/

(SEQ ID NO: 87)
ATTCAAAGGGTATCTGGGCTCTGG,

TPOX:
                                     (SEQ ID NO: 88)
ACTGGCACAGAACAGGCACTTAGG/

(SEQ ID NO: 89)
GGAGGAACTGGGAACCAC ACAGGT, vWA:
                                     (SEQ ID NO: 90)
CCCTAGTGGATGATAAGAATAATCAGTATG/

(SEQ ID NO: 91)
GGACAGATGATAAAT ACATAGGATGGATGG.
```

These cell lines were authenticated because the short tandem repeat (STR) profiles of the cell lines perfectly matched those published by ATCC. ABC kit was purchased from Vector Labs, Inc., OH. ABC kit was purchased from Vector Labs (Youngstown, Ohio). Unless indicated otherwise, all signal transduction analysis on cells transformed with MAN2A1-FER fusion gene were starved without serum 24 hours before induction of MAN2A1-FER expression by tetracycline.

Tissue Samples.

One hundred and thirty-nine specimens of PCa, 10 matched blood samples and 20 organ donor prostates (OD), 102 non-small cell lung cancers, 61 ovarian cancers, 70 liver cancers, 156 glioblastoma multiforme, 27 esophageal adenocarcinoma and 269 prostate cancer samples were obtained from University of Pittsburgh Tissue Bank in compliance with institutional regulatory guidelines (Tables 5-10). Procedures of microdissection of PCa samples and DNA extraction were previously described[3]. The protocols of tissue procurement and procedure were approved by Institutional Review Board of University of Pittsburgh.

RNA Extraction, cDNA Synthesis and Taqman RT-PCR.

Microdissection was performed on slides of FFPE samples to obtain at least 50% cancer cells. Total RNA was extracted from epithelial cells with the Trizol method (InVitrogen, CA). The extraction procedure was performed according to manufacturer's recommendation. Random hexamer was used in the first strand cDNA synthesis with 1 ug of total RNA and Superscript II™ (InVitrogen, inc, CA). This was followed by Taqman PCR (94° C. for 2 min, then 94° C. for 30 seconds, 61° C. for 30 second, 72° C. for 30 second for 50 cycles) in Eppendorf Realplex™ cycler using primers TGGAAGTTCAAGTCAGCGCAG (SEQ ID NO:92)/GAAGTTTTATCCTTTAATGTGCCC (SEQ ID NO:93) and Taqman probe 5'-/56-FAM/TCAGAA ACA (SEQ ID NO:94)/ZEN/GCC TAT GAG GGA AAT T (SEQ ID NO:95)/3IABkFQ/-3'. β-actin Taqman RT-PCR was used quantity and quality controls using primers GCATGGGTCAGAAGGATTCCT (SEQ ID NO:96)/ GTGCTCGATGGGGTACTTCAG (SEQ ID NO:97) and Taqman probe 5'-/56-FAM/CGA CGA GGC (SEQ ID NO:98)/ZEN/CCA GAG CAA GAG (SEQ ID NO:99)/ 3IABkFQ/-3'. Samples with Ct less than 36 were called positive for MAN2A1-FER. When samples showed β-actin Ct higher than 35, nested Taqman RT-PCR for MAN2A1-FER was performed under this condition: 94° C. for 2 min, then 94° C. for 30 seconds, 61° C. for 30 second, 72° C. for 30 second for 25 cycles using primers CTGCTTCAG-GAAAACCTGTGG (SEQ ID NO:100)/TACATGTTT-TAACAGCAACAGAAG (SEQ ID NO:101). This was followed with a nested PCR using primers TGGAAGTTCAAGTCAGCGCAG (SEQ ID NO:102)/ GAAGTTTTATCCTTTAATGTGCCC (SEQ ID NO:103) and Taqman probe: 5'-/56-FAM/TCA GAA ACA (SEQ ID NO:104)/ZEN/GCC TAT GAG GGA AAT T (SEQ ID NO:105)/3IABkFQ/-3' under the this condition: 94° C. for 2 min, then 94° C. for 30 seconds, 61° C. for 30 second, 72° C. for 30 second for 40 cycles. Ct threshold of MAN2A1-FER detection: 30 cycles for formalin-fixed paraffin embedded tissues, 25 cycles for frozen tissues. No template negative control and MAN2A1-FER cDNA templates were used as negative and positive controls in each batch, respectively.

Vector Construction.

Full length cDNA of MAN2A1-FER was obtained from the cDNA library of prostate cancer patient sample PRCA159T using primers GACTCAGATGCTTAAGGA-GACTAGGTGCGGAGCAAG (SEQ ID NO:106)/GTACT-CACGTTCTAGATGTGAGTTTTCTCTTGATGATAGTG (SEQ ID NO:107) using AccuPrime Taq polymerase (ThermoFisher Scientific, Waltham, Mass.) under the following conditions: 94° C. for 2 min, then 40 cycles of 94° C. for 1 min, 62° C. for 1 minute, 72° C. for 5 min. This was followed by 72° C. for 10 min. The PCR product was then digested with AflII and XbaI, and ligated into similarly restricted pCDNA4-FLAG vector to create pCDNA4-MAN2A1-FER-FLAG. To construct pGST-MAN2A1-FER, a PCR was performed using primers GACTCAGATGG-GATCCATGAAGTTAAGCCGCCAGTTC (SEQ ID NO:108)/GTACTCACGTGCGGCCGCTGT-GAGTTTTCTCTTGATGATAGTG (SEQ ID NO:109) on a full length MAN2A1-FER cDNA template at the same condition as mentioned above. The PCR product was restricted with BamHI and NotI, and ligated into the similarly restricted pGEX-5x-3 vector to create pGST-MAN2A1-FER. To create pT3-MAN2A1-FER-FLAG, a PCR was performed on the template of pCDNA4-MAN2A1-FER-FLAG using primers GACTCA-GATGGTCGACGAGACTAGG TGCGGAGCAAG (SEQ ID NO:110)/GTACTCACGTGCGGCCGCTGT-GAGTTTTCTCTTGATGATAGTG (SEQ ID NO:111) on a full-length MAN2A1-FER complementary DNA template under the following condition: 94° C. for 2 min, then 40 cycles of 94° C. for 1 min, 62° C. for 1 minute, 72° C. for 5 min. The PCR product was restricted with SalI and NotI, ligated into similarly restricted pENTR vector. The vector was subsequently recombined pT3-eF1α vector by recombination using Gateway® Vector Conversion System to create pT3-MAN2A1-FER-FLAG. To construct ΔMAN2A1-FER-FLAG$^{K722A}$, QuikChange Multi Site-Directed Mutagenesis Kit from Stratagene, Inc was used. The mutagenesis primers are the following: pGCAA-CATGTAAAGAAGATCTTCCTCAGG (SEQ ID NO:112)/ pAACAGCAACAGAA GTTTTATCCTTTAATG (SEQ ID NO:113). To construct pGST-ΔEGFR$^{aa1-650}$, a PCR was performed on pCMV-EGFR DNA template[4] using primers GACTCAGATGGCTAGCATGCGAC CCTCCGGGACGGC (SEQ ID NO:114)/GTACT-CACGTAAGCTTTCATCCCAGTGGCGATGGACG (SEQ ID NO:115) under the following conditions: 94° C. for 2 min, then 40 cycles of 94° C. for 1 min, 62° C. for 1 minute, 72° C. for 5 min. This was followed by 72° C. for 10 min. The PCR product was restricted with NheI and HindIII, and ligated into similarly restricted pGEX-5x-3 to create pGST-ΔEGFRaa$^{1-650}$. To construct pCMV-EGFR$^{aa1-650}$, a PCR was performed on EGFR cDNA template using primers GACTCAGATGAAGCTTTGACTCCGTCCAGTATT-GATC (SEQ ID NO:116)/GTACTCACGTTTCTAGA-CATCCCAGTGGCGATGGACG (SEQ ID NO:117) at the same condition as above. The PCR product was restricted with HindIII and XbaI, ligated to similar restricted pCMVscript vector to create pCMV-EGFR$^{aa1-650}$.

For construction of pMAN2A1$^{int13}$-EGFP-FER$^{int14}$, extended long PCR was performed on 1 mg genome DNA from HUH7 cells using the following primers: GACTCA-GATGGCGGCCGCGAACATCAGAACTGGGAGAGG (SEQ ID NO:134)/GTACTCACGTAAGCTTCAG-GAGAATCACTTGAACCCG (SEQ ID NO:135). The PCR product was then digested with HindIII and NotI, and ligated into similarly digested pEGFP vector to create pMAN2A1$^{int13}$-EGFP. A synthetic sequence corresponding to splicing acceptor site of MAN2A1 intron 13/exon 14 (TAATGTTGGTTTTAC-CAAAAATATAAATGGTTTGCCTCTCAGTAGATAA-CATT TATCTTTAATAAATTCCCTTCCCTATCTTT-TAAAGATCTCTTTTCGAGCACATA T (SEQ ID NO:136)/TAATATGTGCTCGAAAAGAGATCTT-TAAAAGATAGGGAAGGGAATTTATTAA AGA-TAAATGTTATCTACTGAGAGGCAAACCATTTATAT-TTTTGGTAAAACCAA CAT (SEQ ID NO:137)) was ligated to ASE1 restricted pMAN2A1$^{int13}$-EGFP. Separately, a PCR was performed on HUH7 genome DNA using primers GACTCAGATGGAATTCAAGGTG-GAACACAGAAGGAGG (SEQ ID NO:138)/GTACT- CACGTGAATTCGATTACTTTAAATAACT-CACTTGGCTTCTTGCAGAGG TAGAGCTGAGAGAAG (SEQ ID NO:139) to generate a 1984-bp sequence corresponding to intron 14 of FER, including a 31-bp splice donor site sequence corresponding to FER exon 15/intron 15. The PCR was then restricted with EcoR1, and ligated into similarly restricted pMAN2A1$^{int13}$-EGFP to create pMAN2A1$^{int13}$-EGFP-FER$^{int14}$. For guide RNA NickaseNinga vector, the following guide RNA pair is used: ATAGCTAGAAGGTGGATCAC (SEQ ID NO:140)/ TAGCATTAAGGGCCCCCTAA (SEQ ID NO:141). The construction procedure followed the manual provided by the manufacturer (DNA 2.0, Menlo Park, Calif.).

Colony Formation and Matrigel Traverse Assays.

Colony formation assays were similar to those previously described.[5] PC-3, DU145, NIH3T3, Hep3B, A-172 and H23 cells that were transfected with pCDNA4-MAN2A1-FER-FLAG/pCDNA6-TO were used to evaluate the impact of addition of MAN2A1-FER on colony formation. HUH7 with MAN2A1-FER knockout or vector control were used to evaluate the impact of removal of MAN2A1-FER on colony formation. For colony formation assay, 5000 cells were cultured in 60-mm dishes or 1000 cells were cultured in 35-mm dishes. Triplicate experiments were performed for each cell clones. For cells transfected with pCDNA4-MAN2A1-FER-FLAG/pCDNA6-TO, the medium will be supplemented with 5 µg/ml tetracycline to induce the expression of MAN2A1-FER-FLAG. Medium was changed every 4 days. On the 10th day, the plates were stained with 1% crystal violet, and colonies with diameter of more than 2 mm were counted.

For Matrigel traverse assay[6], cells from each indicated clone were suspended in medium containing 0.1% bovine serum albumin added to the upper chamber at 1×10$^5$ cells/insert. A conditioned medium obtained by incubating NIH 3T3 cells for 24 hours in DMEM supplemented with 10% fetal bovine serum in the presence of 50 µg/ml ascorbic acid was placed in the lower compartment of the invasion chambers as chemoattractants. After 24 hours of culture, the upper surfaces of the inserts were wiped with cotton swabs, and the inserts were stained with hematoxylin and eosin (H&E). Each experiment was performed twice with each sample in triplicate. The cells that migrate through the Matrigel and the filter pores to the lower surface were counted under a light microscope with five random high-power fields per insert.

In Vitro Kinase Assay:

E. coli. harboring GST, GST-MAN2A1-FER and GST-FER were grown overnight in room temperature. The recombinant proteins were induced with 1 mM IPTG for 4 hours. GST, GST-MAN2A1-FER and GST-FER were purified by glutathione column, and diluted to 1 ng/µl with 1× kinase assay buffer provided by manufacturer (Cell Signaling, Inc, Danvers, Mass.). This was followed by combining 25 µl GST or GST-MAN2A1-FER or GST-FER and 25 µl substrate (3 µM poly EY[4:1]). The solutions were incubated at 37° C. for 60 minutes. The reactions were terminated by adding 25 µl of 2N NaOH stop solution to each reaction well. The kinase activities were quantified using the kit and protocols of ADP-Glo™ Kinase Assay from Promega, Inc, Madison, Wis.

Sucrose Gradient Centrifugation to Isolate Golgi Apparatus.

HEP3B cells (2×10$^8$) induced to express MAN2A1-FER-FLAG were re-suspended in 3 ml HM buffer (0.25 M sucrose, 10 mM Tris Cl, pH7.4), and homogenized in a Dounce homogenizer. This is followed by addition of 6 ml of 2.0 M sucrose gradient solution (0.8, 12, 1.6, 2.0 M). The sample was then overlaid with 6 ml of 1.2 M sucrose gradient solution and 3 ml of 0.8 M sucrose solution. The tube was subsequently underlaid with 2 ml of 1.6 M sucrose gradient solution by a syringe and metal cannula. The sample was then centrifuged at 110,000×g for 2 hours at 4° C. The factions of sample solution were then collected from the bottom of the tube. For Golgi isolation experiment, a Golgi isolation kit (Sigma-Aldrich, St. Louise, Mo.) was used. The procedure followed the manual provided by the manufacturer.

Cell Cycle Analysis.

PMF, DMF, NMF, HepMF, AMF, HMF, HEPAK, NMFΔK, HUH7/KO and HUH7/HC cells were cultured with the medium mentioned in "Cell lines" section to 40%-50% confluence. These cells were treated with medium containing no serum for 24 h to synchronize the culture to $G_0$ phase. The cultures were then switched to BrdU labeling medium (Sigma-Aldrich, Inc., St. Louise, Mo.) with 10% fetal bovine serum for 4 h. The cells were subsequently harvested and centrifuged at 500×g for 5 min, and re-suspended in 0.5 ml PBS. The cells were then incubated with anti-BrdU antibodies for 12 hours. This was followed by washing with Triton X-100 permeation buffer, and incubated with secondary antibodies labeled with FITC for 1 hour at room temperature. The cells were transferred to another tube and held in 4.5 ml 70% cold ethanol for 2 hours. Alternatively, the cells were then fixed and permeabilized with BD cytofix/cytoperm buffer. Cells were then resuspended in 50 mL BD cytofix/cytoperm buffer containing diluted anti-bromodeoxyuridine antibody conjugated with fluorescein isothiocyanate, and incubated at room temperature for 20 minutes. The cell pellets were stained in 1 ml 7-Aminoactinomycin D/triton X-100 staining for 30 min at room temperature. The DNA content and cell number were quantified through flow cytometry using a FACSCalibur Automated Benchtop Flow Cytometer (Becton Dickinson, Mass.). The data were quantified and analyzed through Cell Quest program or WinMDI software.

Immunoblot Analysis of MAN2A1, FER, MAN2A1-FER, and β-Actin.

MAN2A1-FER expression was examined in HUH7 cells. First, cells were washed with PBS and lysed by RIPA buffer (50 mM Tris-HCl at pH 7.4, 1% Nonidet P-40, 0.25% sodium deoxycholate, 150 mM NaCl, 1 mM EDTA, 1 mM phenylmethylsulfonyl fluoride, Aprotinin at 1 µg/mL, leupeptin at 1 µg/mL, pepstatin at 1 µg/mL, and 1 mM $Na_3VO_4$). The lysates were sonicated and centrifuged at 12,000 g at 4° C. for 30 minutes to remove the insoluble materials. The proteins were separated by sodium dodecyl sulfate-polyacrylamide gel electrophoresis (SDS-PAGE) in 8.5% polyacrylamide gels, and bands were blotted onto a polyvinylidene difluoride (PVDF) membrane. The membrane was blocked with 5% powdered skim milk in Tris-Tween 20 buffer (0.1 M Tris-HCl and 0.1% Tween-20, pH 7.4) for 1 hour at room temperature, followed by a 2-hour incubation with primary anti-MAN2A1 antibodies (1:1000 dilution, Santa Cruz), anti-FER antibodies (1:1000 dilution; Santa Cruz, Calif.), or anti-GAPDH antibodies (1:500 dilution; Santa Cruz). The membrane was then washed three times with Tris-Tween 20 buffer and incubated with a horseradish peroxidase-conjugated secondary antibody specific for rabbit (anti-GAPDH, 1:1000 dilution), mouse (anti-MAN2A1, 1:1000 dilution), or goat (anti-FER, 1:1000 dilution) for 1 hour at room temperature. The protein expression was detected with the ECL system (Amersham Life Science) according to the manufacturer's protocols. Similar immunoblotting was also performed on protein extracts from prostate cancer samples PRCa159T, PRCa23T, PRCa25T, PRCa20T, PRCa119T, and liver cancer cell line HEP3B.

Tumor Growth and Spontaneous Metastasis.

The xenografting procedure was described previously.[4-6,8] Briefly, approximately $5 \times 10^6$ viable PMF, DMF, HEPMF, GMF, HMF, and HUH7 and HUH7/ko cells suspended in 0.2 mL Hanks' balanced salt solution (Krackeler Scientific, Inc, Albany, N.Y.) were subcutaneously implanted in the abdominal flanks of 71 severe combined immunodeficient (SCID) mice to generate 1 tumor per mouse. The breakdown of the treated groups is the following: 12 for PMF cells; 12 for DMF cells; 11 for HEPMF cells; 12 for GMF cells, 12 for HMF cells, 6 for HUH7 cells; and 6 for HUH7/ko cells. Six mice from each of PMF, DMF, HEPMF, GMF, and HMF groups were fed with 5 mg/mL tetracycline water daily. Mice were observed daily, and their body weight and tumor size were recorded weekly. Tumor sizes were measured on weekly until the end of the sixth week after the xenografting. Mortality and metastases were recorded.

Treatment of Severe Combined Immunodeficient Mice Xenografted with Cancer Cells.

For kinase inhibitor treatment experiments, PMF, GMF, HUH7, and HUH7/ko cells ($2 \times 10^7$ cells) were xenografted into the subcutaneous region of SCID mice. Two weeks after xenografting, these mice were treated with dimethyl sulfoxide, crizotinib (12.5 mg/kg), canertinib (10 mg/kg), or the combination of these 2 drugs, 3 times a week, as indicated in FIG. 19, through intraperitoneal applications. After 7 weeks, all survived mice were killed, and necropsies were performed. For mice treated with control reagents, necropsies were performed when mice died from the xenografted cancers. Serial sections of formalin-fixed, paraffin-embedded lung, brain, liver, kidney, vertebra, and lymph node specimens were collected, stained with H&E, and examined microscopically.

Mice and Hydrodynamic Tail-Vein Injections.

Hydrodynamic-tail vein injections were performed as described previously.[8] Briefly, first Pten$^{tm1Hwu/J}$ mice of which exon 5 of Pten gene was flanked by loxP sites was treated with adeno-associated virus-cre ($1 \times 10^{10}$ pfu) through intraperitoneal injection to create Pten knockout in most hepatocytes. Next, 20 µg pT3-MAN2A1-FER-FLAG, along with the sleeping beauty transposase in a ratio of 25:1, were diluted in 2 mL normal saline (0.9% NaCl), filtered through 0.22-µm filter (Millipore), and injected into the lateral tail vein in 5 to 7 seconds. Mice were housed, fed, and monitored in accordance with the protocols approved by the Institutional Animal Care and Use Committee at the University of Pittsburgh School of Medicine.

6.3 Results

MAN2A1-FER Fusion Expression in Human Malignancies.

Figure 13A:
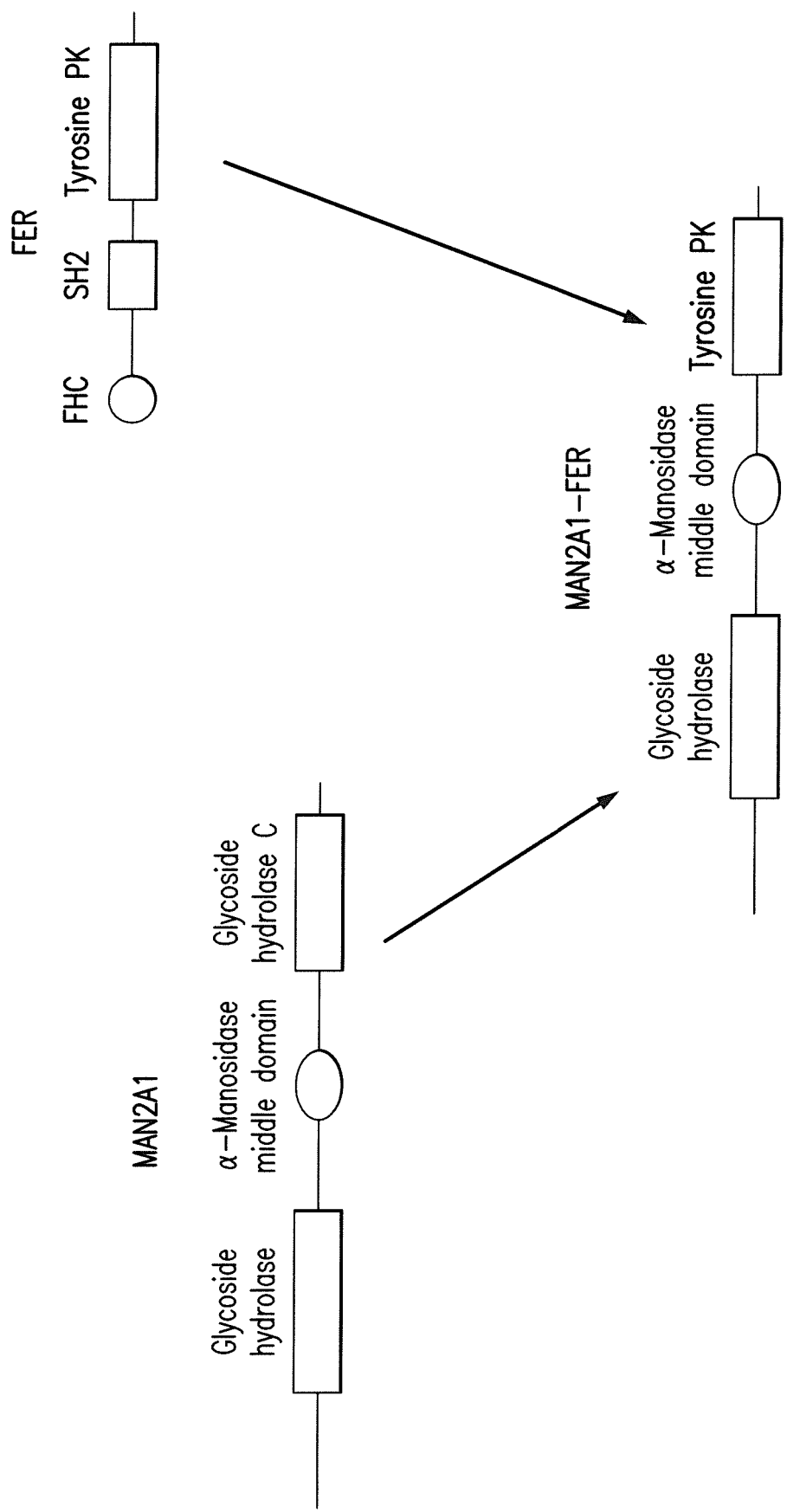
Figure 13B:
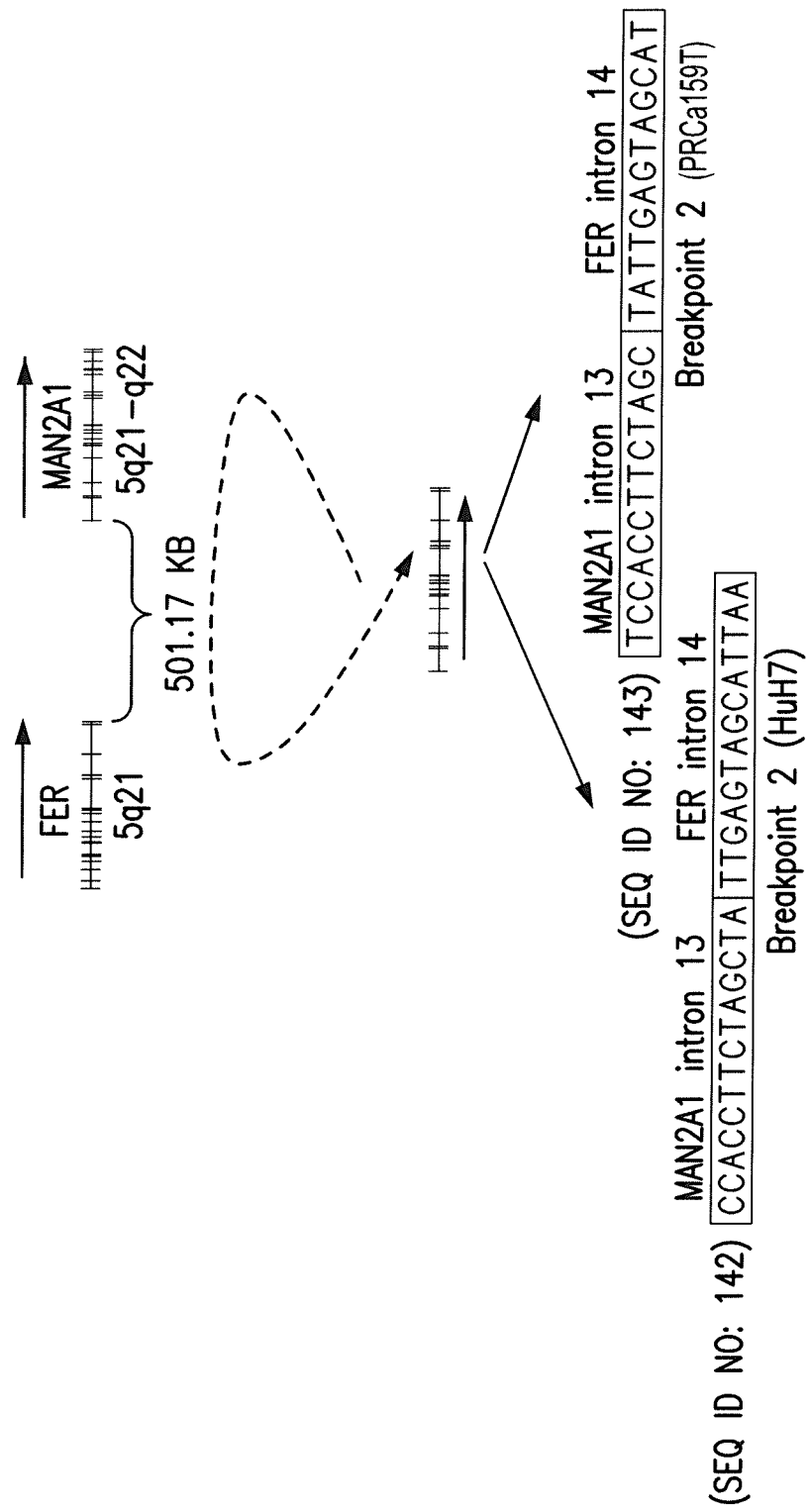
Figure 13D:
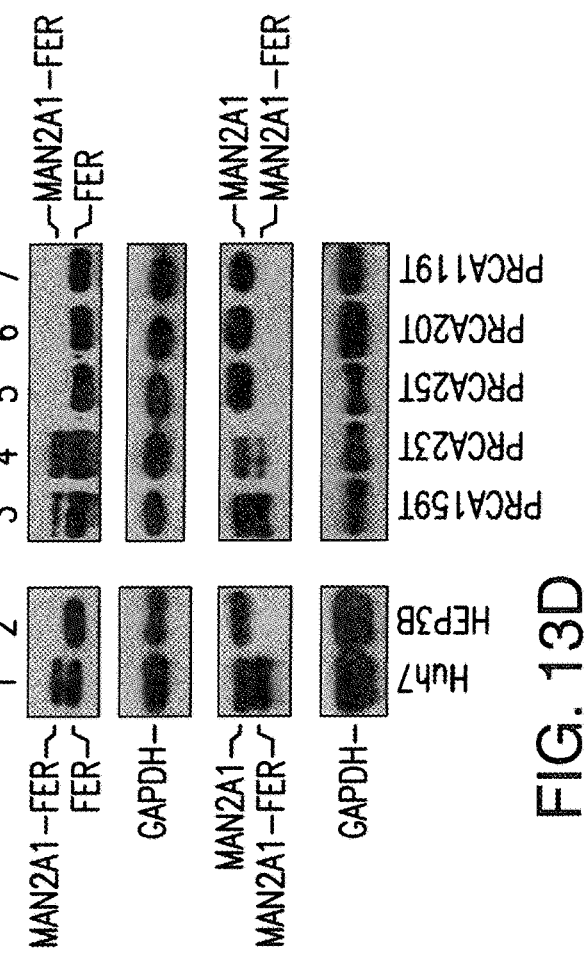
Figure 13C:
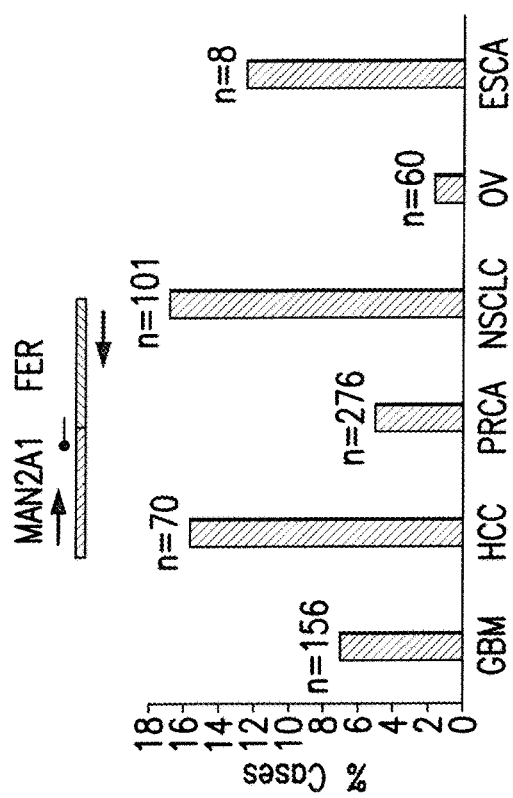

Fusion between MAN2A1 and FER resulted in the loss of 441 amino acids from the C-terminus of MAN2A1 and 571 amino acids from the N-terminus of FER. This produces major structural alterations in the protein (FIG. 13A). To investigate what type of human cancers harbors MAN2A1-FER fusion, we examined 6 different types of human cancers including prostate cancer, glioblastoma multiforme, non-small cell lung cancer, ovarian cancer, esophagus adenocarcinoma and liver cancer, using Taqman quantitative RT-PCR. All 6 types of these cancers were found positive for MAN2A1-FER fusion, ranging from 2-25.9% (FIG. 13C and Tables 5-10). This includes 16.8% (17/101) non-small cell lung cancer, 15.7% (11/70) liver cancer (FIG. 22), 7.1% (11/156) GBM, 25.9% (7/27) esophagus adenocarcinoma, 5.2% (14/269) prostate cancer, and 1.7% (1/60) ovarian cancer (FIG. 13C). All 20 organ donor prostate samples, 10 liver donor samples and 10 blood samples from prostate cancer patients were negative for MAN2A1-FER fusion. The chimeric MAN2A1-FER protein contains 954 amino acids, while MAN2A1 has 1144 and FER has 822 amino acids, respectively. Thus, the protein molecular weight of MAN2A1-FER chimera protein is projected to have a molecular weight 114 kd, while MAN2A1 has 137 kd and FER 99 kd.

To examine whether MAN2A1-FER fusion gene produces a stable chimera protein, we screened 15 human cancer cell lines derived from several different type cancers. HUH7, a hepatocellular carcinoma cell line, was found to express high level of MAN2A1-FER transcript. Through whole genome sequencing of prostate cancer positive for MAN2A1-FER (PRCA159T), a chromosome breakpoint was found located in intron 13 of MAN2A1 and intron 14 of FER (FIG. 13B). A separate MAN2A1-FER chromosome breakpoint was found in HUH7 cell line (FIG. 13B). Only 32 bps separate this breakpoint from that found in the prostate cancer sample. When immunoblots using antibodies specific for MAN2A1 or FER were performed, a protein band with a molecular weight 114 kd was recognized by both antibodies specific for MAN2A1 and FER. This protein band is absent in MAN2A1-FER transcript negative HCC cell line HEP3B (FIG. 13D). This suggests that MAN2A1-FER fusion gene produces a stable chimeric protein. To test whether MAN2A1-FER protein was also expressed in primary cancer samples, similar immunoblotting was performed on prostate cancer positive for MAN2A1-FER fusion. As shown in FIG. 13D, samples (PCA159T, PRCA23T, HCC #1, HCC #2 and HCC #5) that were positive for MAN2A1-FER transcript contained an extra protein band of molecular weight 114 kd recognized by antibodies specific for MAN2A1 and FER, while samples (PRCA25T, PRCA20T, PRCA119T, HCC #10, HCC #37, Normalliver #71 and Normalliver #72) that were negative for MAN2A1-FER contained no such protein. These experiments indicate that MAN2A1-FER protein is stably expressed when fusion transcript is present.

MAN2A1-FER is Located in Golgi Apparatus.

Figure 14A:
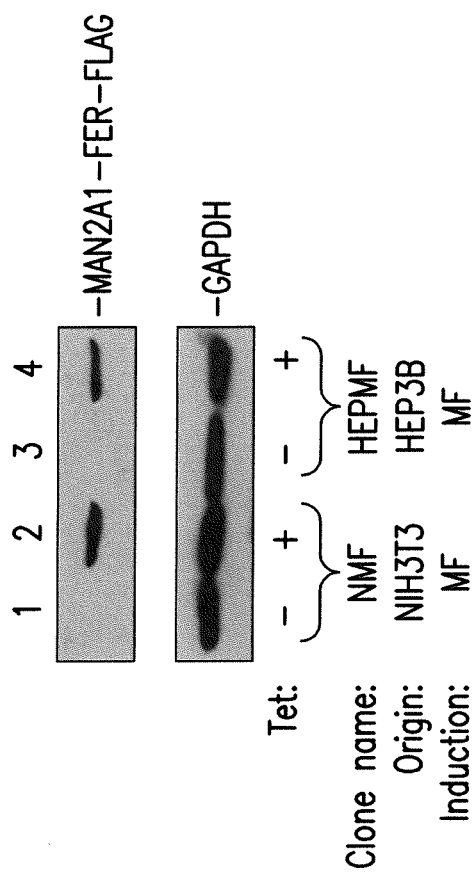
Figure 14B:
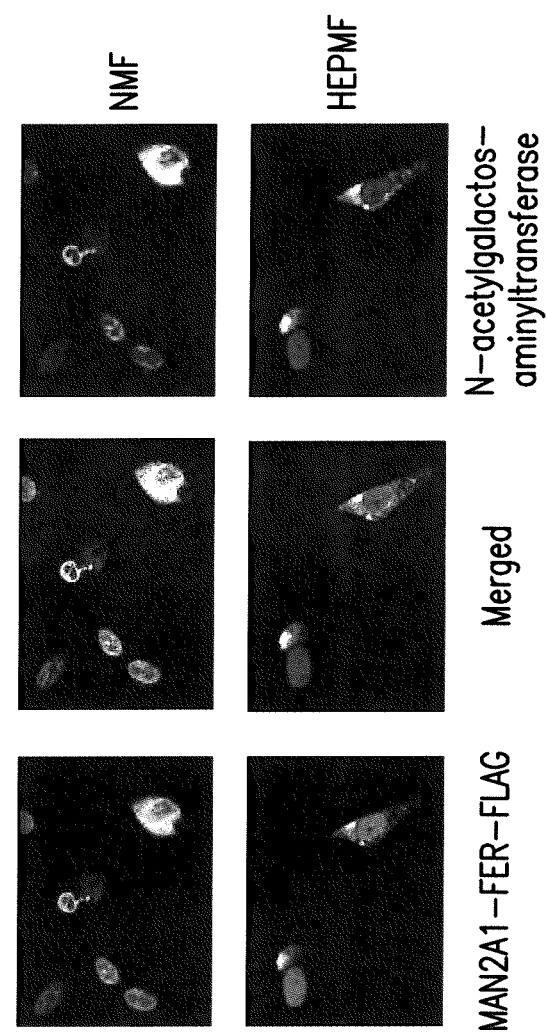

FER protein contains a FCH domain, which is the binding site for microtubules of the FER protein. In the MAN2A1-FER fusion, this domain is lost. Instead, MAN2A1-FER retains the signal peptide for Golgi location from MAN2A1. As a result, the kinase domain of FER is likely translocated to Golgi apparatus. To test this hypothesis, NIH3T3 and HEP3B cells were transfected with pCDNA4-MAN2A1-FER-FLAG/pCDNA6. Stable tetracycline inducible MAN2A1-FER-FLAG expression clones were selected (NMF and HEPMF, FIG. 14A). Co-immunostaining using antibodies specific for FLAG and resident Golgi protein N-acetylgalactosaminyltransferase showed that MAN2A1-FER-FLAG and N-acetylgalactosaminyltransferase were co-localized in Golgi apparatus (FIG. 14B). Sucrose gradient centrifugation separation of fractions of HEP3B cells transformed with MAN2A1-FER-FLAG showed that MAN2A1-FER-FLAG was located in the Golgi fraction, distinctly different from the wild type FER protein, which was found in the cytoplasm fraction (FIG. 14C). Finally, Golgi localization of MAN2A1-FER from HUH7 and NMF cells were also confirmed by a Golgi isolation method (FIG. 14D).

MAN2A1-FER Kinase Activates EGFR.

Figure 15B:
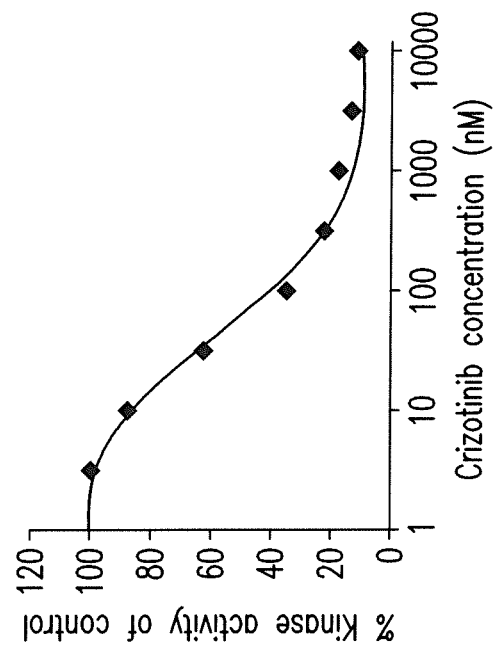
Figure 15A:
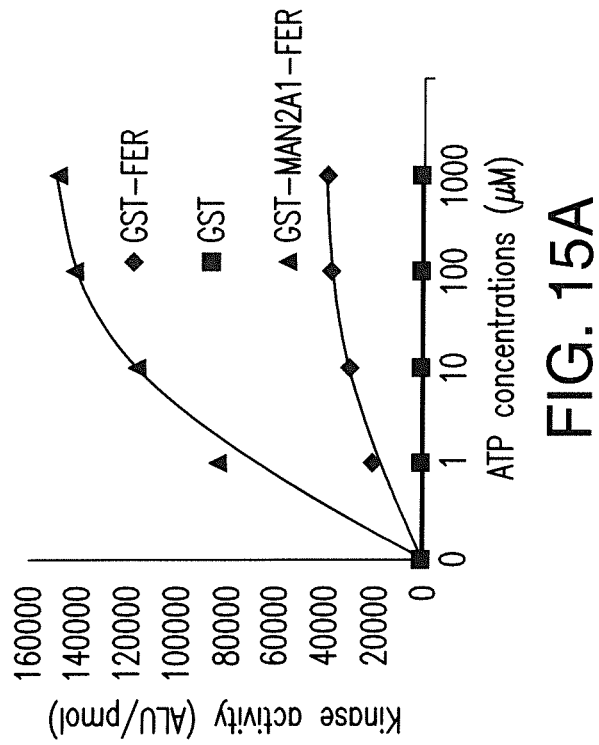

FER is a tyrosine kinase that plays a significant role in signal transduction. To test whether MAN2A1-FER retains its tyrosine kinase activity, MAN2A1-FER was ligated into pGEX-5x-3 vector to create pGST-MAN2A1-FER so that the fusion protein was expressed as GST-MAN2A1-FER chimera protein in E. coli. As shown in FIG. 15A, GST-MAN2A1-FER showed high level of tyrosine kinase activity when poly (EY 4:1) was used as a substrate. In addition, GST-MAN2A1-FER showed 4 fold higher kinase activities than GST-FER, suggesting that removal of SH2 domain inhibition from FER increased the tyrosine kinase activity of the fusion protein. Interestingly, the kinase activity of MAN2A1-FER is sensitive to crizotinib, a tyrosine kinase inhibitor originally developed for ALK and FER/FEZ, with an $IC_{50}$ ~29 nM (FIG. 15B; Table 3).

Figure 15C:
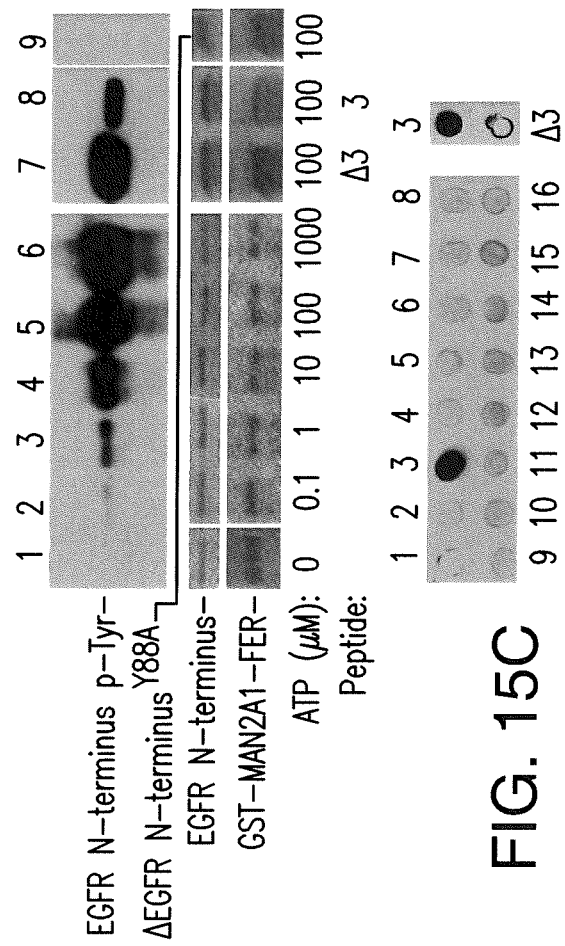

Since MAN2A1-FER fusion results in translocation of FER kinase to Golgi apparatus, the targets of FER kinase may be altered as a result. Epidermal growth factor receptor (EGFR) signaling activation has been shown to be one of the major mechanisms that drive the progression of human cancers[7], and only the N-terminus of EGFR is exposed to the lumens of Golgi apparatus. We hypothesize that EGFR N-terminus is the substrate of MAN2A1-FER kinase. To test this hypothesis, we used the N-terminus of EGFR (HisTAG-$EGFR^{aa1-650}$) as the substrate in our kinase assay. As shown in FIG. 15C, GST-MAN2A1-FER phosphorylated the recombinant HisTAG-$EGFR^{aa1-650}$ in an ATP dosage-dependent manner. To investigate which tyrosine residue was phosphorylated by GST-MAN2A1-FER, synthetic peptides corresponding to each tyrosine residue in the N-terminus of EGFR was chemically synthesized, and assayed for the phosphorylation by GST-MAN2A1-FER. The results showed that only the sequence corresponding to FLK-TIQEVAGYVLIALNTVER (peptide 3) in EGFR was phosphorylated by GST-MAN2A1-FER. This peptide contains a tyrosine residue at aa88 of EGFR. To validate whether Y88 in EGFR is indeed phosphorylated by GST-MAN2A1-FER, a peptide containing a mutation of this tyrosine (Y88A) was assayed for the protein kinase activity of GST-MAN2A1-FER. The result indicated that mutant peptide was not phosphorylated by the fusion protein. To verify whether the phosphorylation of HisTAG-$EGFR^{aa1-650}$ by GST-MAN2A1-FER fusion is the result of Y88 phosphorylation, HisTAG-$\Delta EGFR^{aa1-650}$ phosphorylation was performed by excessive amount of peptide 3. As shown in FIG. 15C (lanes 7-8), peptide 3, but not the mutant counterpart, partially blocked the phosphorylation of EGFR N-terminus by GST-MAN2A1-FER. No phosphorylation was found when Y88 was mutated to alanine in EGFR N-terminus (FIG. 15C). Thus, Y88 is the only GST-MAN3A1-FER phosphorylation site in EGFR N-terminus (FIG. 23).

Figures 15D, 15E:
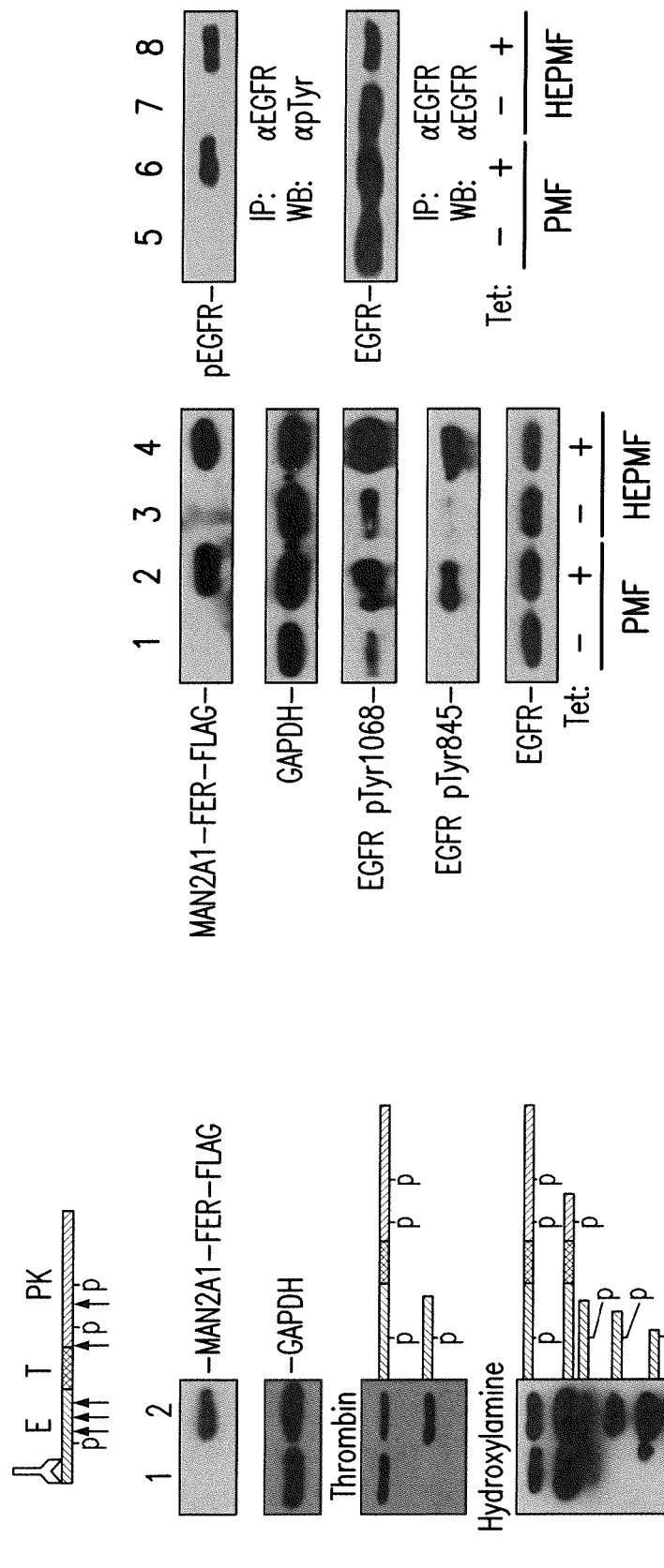
Figure 15G:
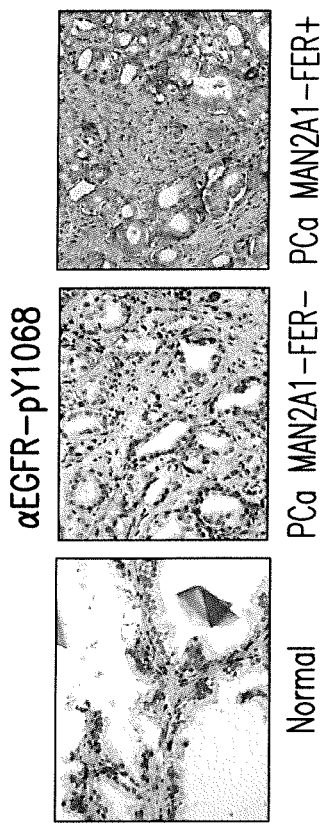
Figure 15F:
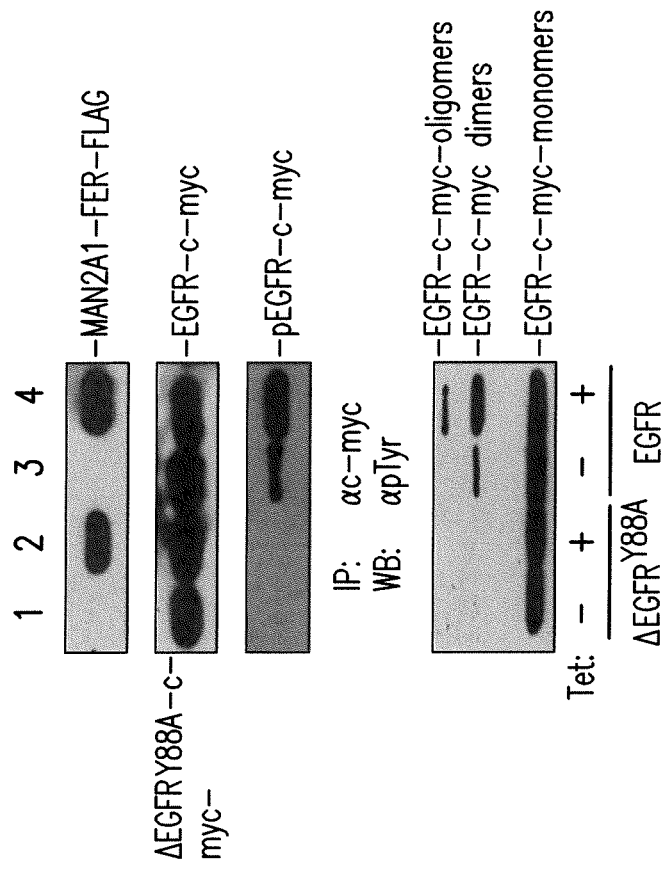

To investigate whether phosphorylation of the N-terminus of EGFR by MAN2A1-FER kinase occurs in vivo, HEPMF cells were induced with tetracycline to express MAN2A1-FER-FLAG. EGFR was partially fragmented with thrombin or hydroxylamine. The digested peptides were then immunoprecipitated with antibodies specific for the N-terminus of EGFR. The results showed that MAN2A1-FER expression resulted in phosphorylation of EGFR N-terminus, while uninduced controls were negative for the N-terminus EGFR phosphorylation (FIG. 15D). Expression of MAN2A1-FER led to activation of tyrosine kinase activity of EGFR, as evidenced by dramatic increase of autophosphorylation of $Y^{1068}$ and $Y^{848}$ in the kinase domain (FIG. 15E). To investigate whether N-terminus phosphorylation of EGFR is essential for MAN2A1-FER mediated EGFR activation, a mutant with a point mutation in amino acid 88 (Y88A) of EGFR was created. This mutant was transfected into HEPMF cells and induced to express MAN2A1-FER-FLAG. As shown in FIG. 15F, mutation of tyrosine 88 of EGFR abrogated the tyrosine kinase activation of EGFR as evidenced by negative autophosphorylation and dimerization when MAN2A1-FER was induced to express. The activation of EGFR was also identified in a prostate cancer sample that was found positive for MAN2A1-FER fusion (FIG. 15G), but not in a sample that was negative, suggesting a significant clinical relevance for the activation of EGFR induced by MAN2A1-FER.

Figures 16A, 16B, 16C, 16D:
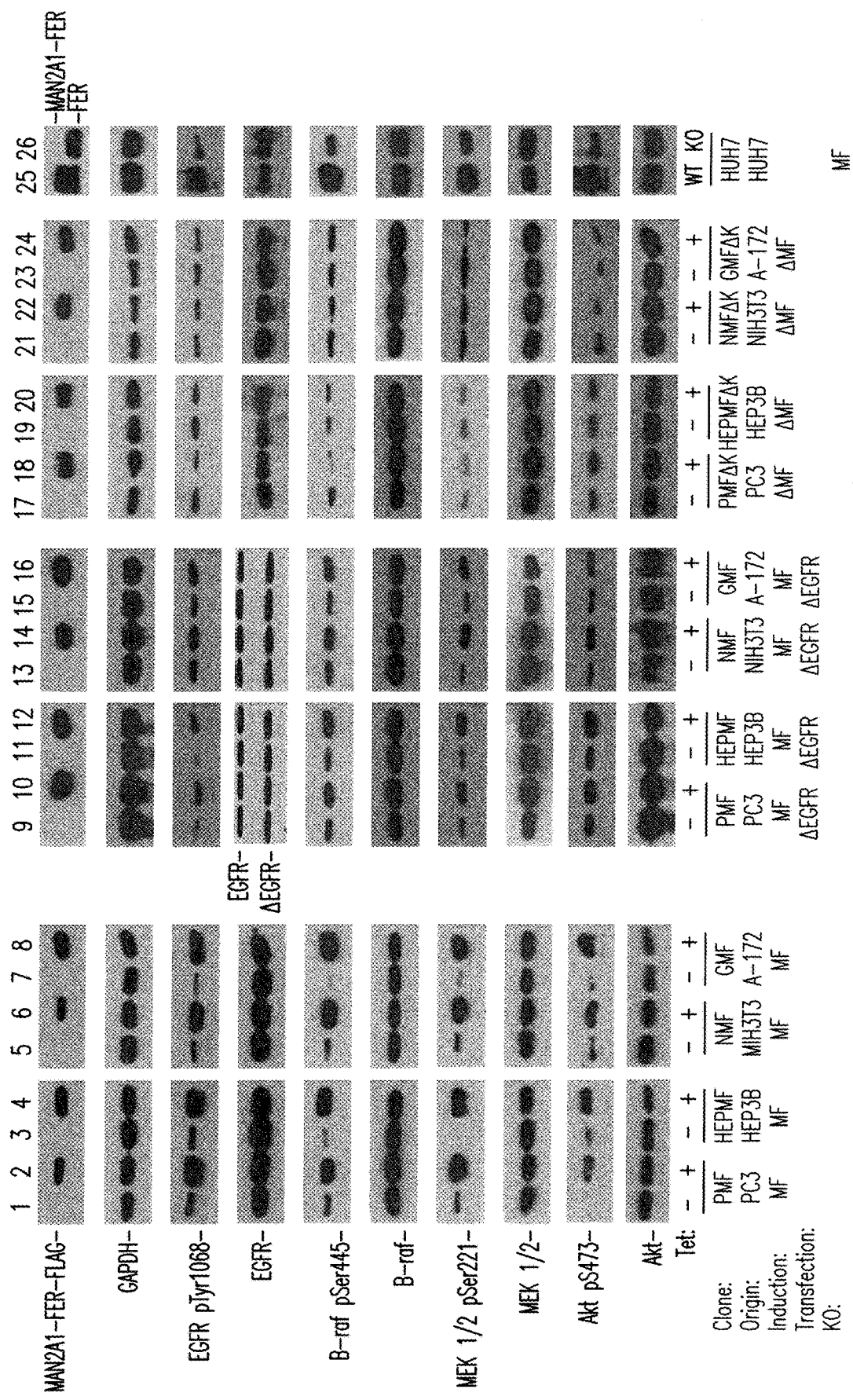

Activation of the kinase activity of EGFR by MAN2A1-FER may lead to cascade of pro-growth signaling in cancer cells. To examine whether expression of MAN2A1-FER activates EGFR signaling pathways, EGFR-B-raf-MEK and EGFR-Akt pathways were examined. As shown in FIG. 16, expression of MAN2A1 in 4 cell lines of different origins (PC3-prostate cancer, HEP3B-liver cancer, NIH3T3-mouse immortalized fibroblast and A-172, glioblastoma multiforme) led to activation B-raf, MEK and Akt kinases, while the kinase negative mutant of MAN2A1-FER failed to activate any of these kinases. To examine whether EGFR is the main activator of these kinases, a dominant negative mutant of EGFR ($\Delta EGFR^{aa1-650}$) that has its kinase domain deleted was transfected into these cell lines. The results indicated that the presence of $\Delta EGFR^{aa1-650}$ largely eliminated the activations of these kinases. The results indicated that the presence of $\Delta EGFR^{aa1-650}$ largely eliminated the activations of these kinases (FIG. 16B). The kinase-negative mutant of MAN2A1-FER failed to activate any of these kinases (FIG. 16C). Using CRISPR system, genome of MAN2A1-FER in HUH7 cells was interrupted such that no MAN2A-FER expression is present in the cell line (FIG. 16D, lanes 25-26). HUH7 cells with knockout of MAN2A1-FER showed significant decrease of phosphorylation of EGFR, B-raf, MEK, and Akt, suggesting that hyper-activation of these kinases in HUH7 cells are largely dependent on the MAN2A1-FER fusion.

MAN2A1-FER Accelerates Cell Growth and Invasion.

To examine the consequence of MAN2A1-FER induced activation of pro-growth signaling pathways, cell cycle analysis was performed on cell lines of 4 different origins (PC3 and DU145-prostate cancer, HEP3B-liver cancer, A-172-glioblastoma multiforme, H23-lung cancer) and NIH3T3 that were transformed with MAN2A1-FER-FLAG. As shown in FIG. 17A, induction of expression of MAN2A1-FER by tetracycline increased the S-phase of these cell lines dramatically: 2.1 fold for PC3, 52% for DU145, 42 fold for HEP3B, 40 fold for H23, 3.9 fold for A-172 and 2 fold for NIH3T3 cells. However, these pro-growth impacts completely disappeared when kinase negative mutant of MAN2A1-FER-FLAG was introduced into these cells (FIG. 17A). Expression of dominant negative mutant $\Delta EGFR^{aa1-650}$ also significantly attenuated the increase of S-phase induced by MAN2A1-FER-FLAG in HEP3B cells. Genomic interruption of MAN2A1-FER in HUH7 cells resulted in significant reduction of S-phase and M-phase cells.

Parallel to these cell cycle analyses, colony formation analysis of cells transformed with MAN2A1-FER-FLAG showed 90% to 2.7 fold increase of colonies when MAN2A1-FER-FLAG was induced (FIG. 17B). The impact of MAN2A1-FER-FLAG on colony formation disappeared when a MAN2A1-FER kinase mutant or dominant negative EGFR mutant was used. Interruption of MAN2A1-FER in the genome HUH7 cells resulted in 55% decrease in colony formation of these cells. Expression of MAN2A1-FER also resulted in higher levels of invasiveness (FIG. 17C). To examine the impact of MAN2A1-FER expression in vivo, PC3, DU145, HEP3B, A-172, H23 cells transformed with MAN2A1-FER were xenografted into subcutaneous tissues of severe combined immunodeficiency (SCID) mice. MAN2A1-FER-FLAG were induced through tetracycline water (5 µg/ml). As shown in FIG. 17D-F, expression of MAN2A1-FER-FLAG produced 2.3 fold larger volume of tumors for PC3 and DU145 tumors, 2.6 fold for HEP3B and 2.4 for A-172 tumors. There was a 55% drop in tumor volume when MAN2A1-FER was interrupted in HUH7 cells. Higher level of metastases was also seen in tumors expressing MAN2A1-FER: 3/36 for tumor negative for MAN2A1-FER versus 19/35 for MAN2A1-FER positive ($p<0.0001$, Table 11 and FIG. 24). Eighty-three percent (30/36) of SCID mice without MAN2A1-FER survived through 6 weeks while only 28.6% (10/35) mice with MAN2A1-FER did so ($p=4.5 \times 10^{-7}$).

MAN2A1-FER Positive Cancers are Sensitive to Crizotinib and Canertinib.

Since the kinase activity of MAN2A1-FER and EGFR activation are the drivers of MAN2A1-FER oncogenic activity, it is of interest to examine whether inhibition of the kinase activity of MAN2A1-FER or EGFR interrupts the oncogenic activity of MAN2A1-FER, and thus the growth of the tumors. To investigate this hypothesis, crizotinib, a MAN2A1-FER kinase inhibitor, and canertinib, an EGFR kinase inhibitor, were chosen to treat PC3, A-172 or HUH7 with or without MAN2A1-FER. The results indicate that the presence of MAN2A1-FER increased the sensitivity of cancer cells to crizotinib, ranging from 1.8 to 2.1 fold, depending on the cell lines (FIG. 18, Table 3). Interestingly, these cancer cell lines appear more sensitive to canertinib: All showed $IC_{50}$ values (50% inhibitory concentrations) below 15 nM (Table 3). The presence of MAN2A1-FER increased the sensitivity by 2.1 to 2.5 fold.

To investigate whether the increased sensitivity of malignant cell lines with MAN2A1-FER to these kinase inhibitors translates into better outcomes for the cancers treated with these drugs, PC3, A-172 and HUH7 cells with or without MAN2A1-FER were xenografted into the subcutaneous region of SCID mice. The tumors were allowed to grow for 2 weeks to an average size of 183 mm³. Then, these mice were treated with crizotinib (12.5 mg/kg), canertinib (10 mg/kg) or the combination of these 2 drugs, 3 times a week through peritoneal injection. When MAN2A1-FER is present, treatment of crizotinib reduced the final tumor sizes by an average of 78.6% ($p<0.001$) in comparison with DMSO controls for PC3 cells, 67.6% ($p<0.001$) for A-172 and 80.7% ($p<0.001$) for HUH7 cells. When MAN2A1-FER was not present, crizotinib was much less effective: an average 27.1% reduction of tumor sizes for PC3, 4% increase for A-172 and 27.6% reduction for HUH7 cells. When SCID mice were treated with canertinib, similar results were obtained: 85.0% ($p<0.001$) reduction of tumor size for PC3 cells, 73.2% ($p<0.001$) for A-172 and 81.7% ($p<0.001$) for HUH7, when MAN2A1-FER was present (FIG. 19A). This compared favorably against cell without MAN2A1-FER: 32.0% reduction for PC3, 19.2% for A-172 and 40.2% for HUH7 cells. The best results came from the combination of crizotinib and canertinib. The combination of crizotinib and canertinib significantly reduced tumor size: 92.2% ($p<0.001$) reduction of tumor size of PC3, 89.0% ($p<0.001$) for A-172 and 86.0% ($p<0.001$) for HUH7 cells, when MAN2A1-FER was present. Without MAN2A1-FER, the effectiveness was reduced to 46.5% for PC3 and 43.2% for HUH7 cells. The combination of crizotinib and canertinib was ineffective for A-172 tumor if MAN2A1-FER was not present (19.4% increase of tumor size). Treatment with either crizotinib or canertinib or the combination of these 2 drugs completely eliminated the metastasis of all tumors (PC3, A-172 and HUH7, 0%, 0/18) versus controls (61%, 11/18) ($p<0.001$), when MAN2A1-FER was present (FIG. 19B). The effects of these drugs on MAN2A1-FER negative cells, however, were largely insignificant: 2/18 for crizotinib or canertinib treated versus 1/18 for control. These results may reflect pervasive low metastasis rate of these malignant cells after MAN2A1-FER was removed. Treatment of crizotinib, canertinib or the combination of these 2 drugs completely eliminated the mortality of the mice xenografted with tumors positive for MAN2A1-FER (FIG. 19C). The mortality improvement effect by these drugs, however, was not observed when they were applied to tumors negative for MAN2A1-FER. These results clearly indicate that MAN2A1-FER is the driver of cancer progression. The presence of MAN2A1-FER drives EGFR signaling that sensitizes the cancer cells to drug specific for this pathway.

TABLE 3

$IC_{50}$ of crizotinib and canertinib.

| Cells | Treatment | IC50 (uM) |
|---|---|---|
| Crizotinib | | |
| PMF | Tet− | 43.35 |
|  | Tet+ | 20.82 |
| GMF | Tet− | 64.66 |
|  | Tet+ | 33.07 |
| HUH7 | WT | 28.85 |
|  | KO | 52.89 |
| Canertinib | | |
| PMF | Tet− | 25.05 |
|  | Tet+ | 10.91 |
| GMF | Tet− | 26.50 |
|  | Tet+ | 10.73 |
| HUH7 | WT | 14.73 |
|  | KO | 30.30 |

MAN2A1-FER Produces Spontaneous Liver Cancer.

Figure 20E:
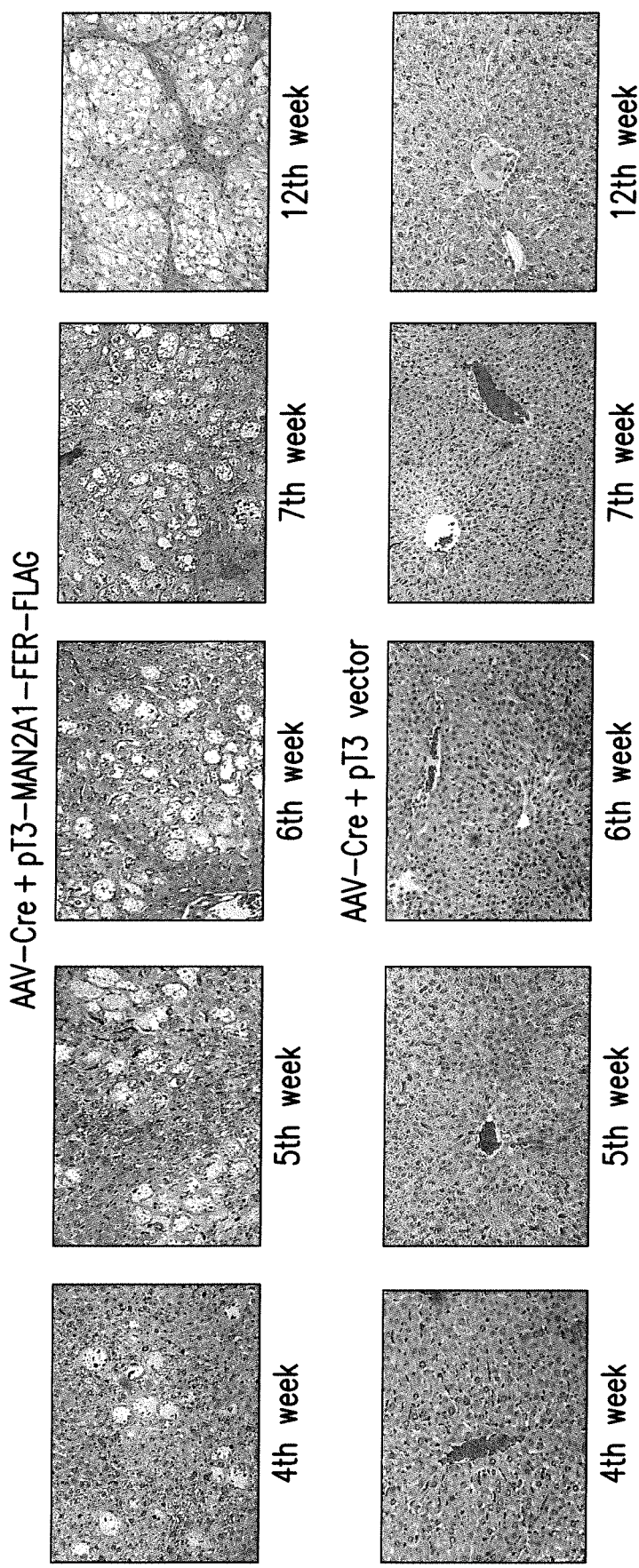

Among the 10 human liver cancer samples that were positive for MAN2A1-FER, 6 showed Pten deletions, suggesting a potential association between the 2 events for the cancer development. To investigate whether Pten deletion and MAN2A1-FER fusion are sufficient to generate cancers, a mouse somatic cancer model was developed to mimic somatic mutations in human cancers. In such model, Pten$^{tm1Hwu/J}$ mice of which exon 5 of Pten gene was flanked by loxP sites was treated with adeno-associated virus-Cre ($1 \times 10^{10}$ PFU) through intra-peritoneal injection to create Pten knockout in most hepatocytes. This was followed by tail vein hydrodynamic injection[8] of pT3-MAN2A1-FER-FLAG such that 1-2% hepatocytes were transfected with the vector (FIG. 20A). These mice was allowed to live up to 12/14 weeks or died from liver cancer naturally. All mice injected with pT3-MAN2A1-FER-FLAG developed hepatocellular carcinoma (FIG. 20B). These mice all had enlarged livers, with liver to body ratio more than 172% of the controls (FIG. 20C). Hyper activations of EGFR/Akt pathways were found in these mice (FIG. 20D). Clear morphological cancer cells were observed in as early as 4 weeks after introduction of pT3-MAN2A1-FER-FLAG through tail vein (FIG. 20E). The cancer islets expanded rapidly in 8 weeks such that most hepatic parenchyma was replaced with cancer cells at the end of 12 weeks. These cancer cells contained large nuclei and nucleoli, were rich in fatty vacuoles and had significant higher number of Ki-67 positive cells (FIG. 21). The glutamine synthetase staining pattern was lost in the cancers (FIG. 21). These features are characteristic of high grade liver cancer. Indeed, no mice survived through 14 weeks after introduction of pT3-MAN2A1-FER-FLAG. In contrast, AAV-cre/pT3 treated mice displayed no detectable pathological phenotype in the same period. Taken together, without being limited to a particular theory, these analyses suggest that MAN2A1-FER is one of the key drivers for human cancer progression.

TABLE 4

Synthetic peptides for phosphorylation assays (SEQ ID NOs: 118-133, respectively).

| Peptide name | Sequence |
|---|---|
| 1 | EVVLGNLEITYVQRNYDLSFL |
| 2 | NLEITYVQRNYDLSFLKTIQE |
| 3 | FLKTIQEVAGYVLIALNTVER |
| 4 | ENLQIIRGNMYYENSYALAVL |
| 5 | NLQIIRGNMYYENSYALAVLS |
| 6 | IRGNMYYENSYALAVLSNYDA |
| 7 | NSYALAVLSNYDANKTGLKEL |
| 8 | CKDTCPPLMLYNPTTYQMDVN |
| 9 | PPLMLYNPTTYQMDVNPEGKY |
| 10 | QMDVNPEGKYSFGATCVKK |
| 11 | ATCVKKCPRNYVVTDHGSCVR |
| 12 | SCVRACGADSYEMEEDGVRKC |
| 13 | VIISGNKNLCYANTINWKKLF |
| 14 | GPDNCIQCAHYIDGPHCVKTC |
| 15 | MGENNTLVWKYADAGHVCHLC |
| 16 | VCHLCHPNCTYGCTGPGLEGC |

6.4 Discussion

The presence of a fusion gene is one of the key features in human malignancies. MAN2A1-FER fusion is the result of recombination in the long arm of chromosome 5. The significant presence of MAN2A1-FER in 6 different human malignancies, e.g., liver cancers and esophageal adenocarcinoma, suggests that this fusion may play significant roles in the development of human cancers. A search of The Cancer Genome Atlas transcriptome sequencing data of 17 types of human cancers failed to detect MAN2A1-FER fusion. Such a discrepancy might result from a significantly smaller proportion of mapped read located at the 50 ends of both MAN2A1 and FER genes in the The Cancer Genome Atlas data (FIG. 25), because high numbers of reads in the 50 end of messenger RNA of MAN2A1 and FER are required for MAN2A1-FER detection. To our knowledge, MAN2A1-FER is the first example of translocation of a constitutively activated tyrosine kinase to Golgi apparatus in a fashion that leads to oncogenic activation of EGFR signaling pathways. Without being limited to a particular theory, it appears that the crucial link in this activation process is the phosphorylation of tyrosine residue 88 in the extracellular domain of EGFR. Without being limited to a particular theory, it appears that tyrosine 88 is the only tyrosine residue of EGFR phosphorylated by MAN2A1-FER, and phosphorylation of this residue is essential for MAN2A1-FER mediated activation and dimerization of EGFR. Tyrosine 88 is located in the interface of domain I/II of EGFR. This region is presumably involved in the initiation of EGFR dimerization. Mutations in this region have been reported and have been shown to be oncogenic[9], probably due to alteration in the domain conformation for dimerization[10]. It is possible that phosphorylation of tyrosine 88 similarly alters the conformation of EGFR dimerization domain and leads to oncogenic activation of the receptor. Despite the apparent enhancement of EGFR activation and dimerization, MAN2A1-FER does not appear to impact the speed of EGFR transportation from Golgi apparatus to plasma membrane (FIG. 26).

FER, a tyrosine kinase, is a well-documented oncogene[11]. Several studies showed that FER activates androgen receptor (AR) by phosphorylating Tyr223 in AR12. Some studies indicate that FER is an essential component of stem cell tyrosine kinase 1 (STK1)[13], mast cell growth factor receptor (kit)[14] signaling and c-met[19] signaling. Over-expression of FER is associated with poor clinical outcomes of breast cancer[15], renal cell carcinoma[16], non-small cell lung cancer[17] and hepatocellular carcinoma[18]. The kinase activity of FER is clearly maintained, and perhaps hyperactivated in MAN2A1-FER fusion due to removal SH2 domain in FER protein. The loss of FCH domain that is required for microtubule binding may make the MAN2A1-FER kinase unavailable for most of its physiological substrates. Thus, total alteration of substrate pattern may occur in vivo. It is possible that some of the over-expressions of FER detected in human cancers are in fact fusion gene associated with FER.

This analysis suggest that constitutive activation and translocation of FER kinase to Golgi apparatus leads to hyper-activation of EGFR signaling. The consequence of such activation not only leads to hyper-growth of cancers but also makes cancer cells susceptible to kinase inhibitors along the EGFR signaling pathways. Indeed, by targeting at the kinases of FER and EGFR, we showed that this approach is consistently effective against different types of human cancers positive for MAN2A1-FER both in vitro and in vivo. The effectiveness of these inhibitors was largely abrogated if MAN2A1-FER protein is removed from the cancer cells, even though the native FER protein is still present. Without being limited to a particular theory, these findings clearly argue that MAN2A1-FER fusion, rather than the native FER, is the driver of human cancers. The effectiveness of crizotinib and canertinib on MAN2A1-FER positive human malignancies has significant clinical implications: The presence of MAN2A1-FER fusion can be screened in these human cancers. Patients with positive MAN2A1-FER fusion can be treated with these drugs to achieve better clinical outcomes, particularly for those patients with metastasis and who are not suitable for surgery or radiation. The current study only provides examples of drug treatment for MAN2A1-FER fusion gene positive cancers. Likely, other kinase inhibitors targeting at MAN2A1-FER or EGFR signaling pathway can be effective against human cancers positive for this fusion. Thus, MAN2A1-FER/EGFR targeting may hold promise as an effective treatment for human cancers positive for this fusion gene such as liver cancers and other malignancies.

6.5 References

1. R. L. Siegel, K. D. Miller, and A. Jemal, C A: a cancer journal for clinicians 66 (1), 7 (2016).
2. Y. P. Yu, Y. Ding, Z. Chen et al., The American journal of pathology 184 (10), 2840 (2014).
3. Y. P. Yu, Y. Ding, R. Chen et al., The American journal of pathology (2013); J. H. Luo, Y. Ding, R. Chen et al., The American journal of pathology 182 (6), 2028 (2013); Y. P. Yu, C. Song, G. Tseng et al., The American journal of pathology 180 (6), 2240 (2012); Y. P. Yu, D. Landsittel, L. Jing et al., J Clin Oncol 22 (14), 2790 (2004); G. Yu, G. C. Tseng, Y. P. Yu et al., American Journal of Pathology 168 (2), 597 (2006); Y. P. Yu, F. Lin, R. Dhir et al., Analytical biochemistry 292 (2), 297 (2001).
4. Z. H. Chen, Y. P. Yu, G. Michalopoulos et al., The Journal of biological chemistry 290 (3), 1404 (2015).
5. L. Jing, L. Liu, Y. P. Yu et al., The American journal of pathology 164 (5), 1799 (2004); B. Ren, Y. P. Yu, G. C. Tseng et al., Journal of the National Cancer Institute 99 (11), 868 (2007).
6. Y. P. Yu, G. Yu, G. Tseng et al., Cancer research 67 (17), 8043 (2007); Y. C. Han, Z. L. Zheng, Z. H. Zuo et al., The Journal of pathology 230 (2), 184 (2013).
7. S. Y. Luo and D. C. Lam, Translational respiratory medicine 1 (1), 6 (2013); K. Gala and S. Chandarlapaty, Clin Cancer Res 20 (6), 1410; C. C. Lee, H. Y. Shiao, W. C. Wang et al., Expertopinion on investigational drugs 23 (10), 1333 (2014).
8. F. Liu, Y. Song, and D. Liu, Gene therapy 6 (7), 1258 (1999); J. Tao, E. Xu, Y. Zhao et al., Hepatology (Baltimore, Md. (2016)).
9. J. C. Lee, I. Vivanco, R. Beroukhim et al., PLoS medicine 3 (12), e485 (2006).
10. K. M. Ferguson, Annual review of biophysics 37, 353 (2008).
11. Q. L. Hao, N. Heisterkamp, and J. Groffen, Molecular and cellular biology 9 (4), 1587 (1989); J. J. Krolewski, R. Lee, R. Eddy et al., Oncogene 5 (3), 277 (1990).
12. J. Rocha, F. Z. Zouanat, A. Zoubeidi et al., Molecular and cellular endocrinology 381 (1-2), 140.
13. C. Guo and G. R. Stark, Proceedings of the National Academy of Sciences of the United States of America 108 (19), 7968.
14. E. Kwok, S. Everingham, S. Zhang et al., Mol Cancer Res 10 (7), 881; E. Voisset, S. Lopez, P. Dubreuil et al., Blood 110 (7), 2593 (2007).
15. I. A. Ivanova, J. F. Vermeulen, C. Ercan et al., Oncogene 32 (50), 5582.
16. Y. Miyata, S. Kanda, H. Sakai et al., Cancer science 104 (6), 681 (2013); C. Wei, S. Wu, X. Li et al., Oncology letters 5 (2), 473 (2013).
17. J. Ahn, P. Truesdell, J. Meens et al., Mol Cancer Res 11 (8), 952 (2013); M. Kawakami, S. Morita, M. Sunohara et al., International journal of clinical and experimental pathology 6 (4), 598.
18. H. Li, Z. Ren, X. Kang et al., BMC cancer 9, 366 (2009).
19. Fan G, Zhang S, Gao Y, et al. Genes Dev 2016; 30:1542-1557.

Various references and accession numbers are cited in this document, which are hereby incorporated by reference in their entireties.

TABLE 5

| | | | | (Non-Small Cell Lung Cancer) Batch 1 | | | | | | |
|---|---|---|---|---|---|---|---|---|---|---|
| Case | MF | Sex | Race | Primary_Site | age | T | N | M | Mets | histology |
| 1 | N | F | W | upper lobe | 78 | 2 | 0 | 0 | None | Squamous, NOS |
| 2 | N | M | W | upper lobe | 80 | 2 | 0 | 0 | None | Squamous, NOS |
| 3 | N | F | B | upper lobe | 58 | 2 | 0 | 0 | None | Squamous |
| 4 | N | M | W | upper lobe | 74 | 2 | 0 | 0 | None | Squamous NOS |
| 5 | N | F | W | lower lobe | 70 | 2 | 2 | 0 | None | Squamous, NOS |
| 6 | N | F | W | lower lobe | 76 | 1 | 0 | 0 | None | Squamous, NOS |
| 7 | P | F | B | upper lobe | 74 | 3 | 0 | 0 | None | Squamous, NOS |
| 8 | N | N/A | N/A | N/A | N/A | N/A | N/A | N/A | N/A | N/A |
| 9 | N | M | W | lower lobe | 80 | 3 | 0 | 0 | None | Squamous, NOS |
| 10 | N | F | W | upper lobe | 71 | 2 | 0 | 0 | None | Squamous, NOS |
| 11 | N | F | W | lower lobe | 82 | 1 | 0 | | None | Squamous, NOS |
| 12 | N | M | W | upper lobe | 75 | 2 | 0 | 0 | None | Squamous, NOS |
| 13 | N | M | W | lower lobe | 81 | 2 | 0 | 0 | None | Squamous, NOS |
| 14 | P | M | W | lower lobe | 80 | 2 | 1 | | None | Squamous, NOS |
| 15 | N | M | W | lower lobe | 72 | 2 | 1 | 0 | None | Squamous, NOS |
| 16 | N | M | W | lower lobe | 52 | 2 | 0 | 0 | None | Squamous, NOS |
| 17 | N | F | W | lower lobe | 71 | 2 | 0 | | None | Squamous, NOS |
| 18 | P | M | W | lower lobe | 71 | 2 | 1 | 0 | None | Squamous, NOS |
| 19 | N | F | W | upper lobe | 71 | 2 | 0 | 0 | None | Squamous, NOS |
| 20 | N | M | B | upper lobe | 65 | 1 | 2 | 0 | None | Squamous, NOS |
| 21 | N | M | W | lower lobe | 69 | 2 | 0 | x | None | Squamous, NOS |
| 22 | N | M | W | lower lobe | 73 | 2 | 1 | 0 | None | Squamous, NOS |
| 23 | P2 | F | W | upper lobe | 75 | 2 | 0 | 0 | None | Squamous, NOS |
| 24 | N | M | W | upper lobe | 71 | 2 | 1 | | None | Squamous, NOS |
| 25 | N | M | W | upper lobe | 74 | 2 | 1 | 0 | None | Squamous, NOS |
| 26 | N | N/A | N/A | N/A | N/A | N/A | N/A | N/A | N/A | N/A |
| 27 | P | M | W | upper lobe | 67 | 2 | 0 | 0 | None | Squamous, NOS |
| 28 | N | F | W | lower lobe | 62 | 2 | 0 | 0 | None | Squamous, NOS |
| 29 | N | M | W | lower lobe | 82 | 2 | 1 | 0 | None | Squamous, NOS |
| 30 | N | M | W | upper lobe | 67 | 2 | 1 | | None | Squamous, NOS |
| 31 | N | M | W | Bronchus | 74 | 2 | 0 | 0 | None | Squamous, NOS |
| 32 | N | M | W | upper lobe | 59 | 2 | 0 | 1 | CNS | Squamous, NOS |
| 33 | N | M | W | upper lobe | 83 | 2 | | x | None | Squamous, NOS |
| 34 | N | M | W | upper lobe | 64 | 2 | 0 | 0 | None | Squamous, NOS |
| 35 | N | F | W | upper lobe | 68 | 2 | 0 | 0 | None | Squamous, NOS |

TABLE 5-continued (Non-Small Cell Lung Cancer)
Batch 1

| Case | MF | Sex | Race | Primary_Site | age | T | N | M | Mets | histology |
|---|---|---|---|---|---|---|---|---|---|---|
| 36 | N | M | W | upper lobe | 73 | 2 | 1 | 0 | None | Basaloid carcinoma |
| 37 | N | M | W | upper lobe | 73 | 2 | 1 | 0 | None | Basaloid carcinoma |
| 38 | P2 | F | W | lower lobe | 76 | 1 | 0 | 0 | None | Squamous, NOS |
| 39 | P | F | W | upper lobe | 60 | 2 | 1 | 0 | None | Squamous, NOS |
| 40 | N | F | W | upper lobe | 56 | 1 | 2 | 0 | None | Squamous, NOS |
| 41 | N | M | B | middle lobe | 56 | 2 | 2 | 0 | None | Squamous, NOS |
| 42 | N | F | W | lower lobe | 74 | 2 | 0 | x | None | Squamous, NOS |
| 43 | N | F | W | upper lobe | 77 | 1 | 0 | 0 | None | Squamous, NOS |
| 44 | N | F | W | upper lobe | 49 | 2 | 0 | 0 | None | Squamous, NOS |
| 45 | N | F | W | upper lobe | 73 | 2 | 1 | x | None | Squamous, NOS |
| 46 | N | F | W | lower lobe | 65 | 2 | 1 | 0 | None | Squamous, NOS |
| 47 | N | M | W | middle lobe | 84 | 1 | 0 | 0 | None | Squamous, NOS |
| 48 | N | M | W | upper lobe | 78 | 2 | 1 | 0 | None | Squamous, NOS |
| 49 | N | F | W | upper lobe | 69 | 4 | 0 |   | None | Squamous, NOS |
| 50 | N | F | W | upper lobe | 71 | 1 | 0 | 0 | None | Squamous, NOS |
| 51 | N | F | W | upper lobe | 79 | 2 | 0 | 0 | None | Squamous, NOS |
| 52 | N | F | B | upper lobe | 61 | 1 | 0 | 0 | None | Squamous, NOS |
| 53 | N | M | W | upper lobe | 56 | 4 | x | x | None | Squamous, NOS |
| 54 | N | F | B | lower lobe | 63 | 1 | 0 | 0 | None | Squamous, NOS |
| 55 | N | F | W | lower lobe | 61 | 1 | 0 | 0 | None | Squamous, NOS |
| 56 | N | F | W | Bronchus | 60 | 4 | 1 | 0 | None | Squamous, NOS |
| 57 | N | M | W | lower lobe | 76 | 4 | 0 | 0 | None | Squamous, NOS |
| 58 | N | M | W | Lung | 65 | 3 | 2 | x | None | Squamous, NOS |
| 59 | N | F | W | lower lobe | 68 | 2 | 0 | 0 | None | Squamous, NOS |
| 60 | N | M | W | upper lobe | 76 | 4 | 1 | 0 | None | Squamous, NOS |
| 61 | N | M | B | lower lobe | 75 | 2A | 0 | x | None | Squamous, NOS |
| 62 | N | M | W | upper lobe | 68 | 1A | 0 | 0 | None | Squamous, NOS |
| 63 | N | F | B | middle lobe | 75 | 1 | 0 | 0 | None | Squamous, NOS |
| 64 | N | M | W | lower lobe | 66 | 1 | 2 | x | None | Squamous, NOS |
| 65 | N | N/A | N/A | N/A | N/A | N/A | N/A | N/A | N/A | N/A |
| 66 | N | M | W | lower lobe | 84 | 2 | 1 | 0 | None | Squamous, NOS |
| 67 | N | F | W | Lung | 55 | 4 | 0 | 0 | None | Squamous, NOS |
| 68 | N | F | W | upper lobe | 66 | 2 | 1 | 0 | None | Squamous, NOS |
| 69 | N | M | W | upper lobe | 84 | 2 | 0 | x | None | Squamous, NOS |
| 71 | P2 | F | W | upper lobe | 53 | 1 | 2 | x | None | Squamous, NOS |
| 72 | N | F | W | N/A | 66 | 1 | 0 | x | Adjacent organs | Squamous, NOS |
| 73 | N | F | W | upper lobe | 57 | 2 | 0 | x | None | Squamous, NOS |
| 74 | N | N/A | N/A | N/A | N/A | N/A | N/A | N/A | N/A | N/A |
| 75 | P | M | A | upper lobe | 64 | 4 | 2 | x | liver | Squamous, NOS |
| 76 | P2 | M | W | upper lobe | 52 | 2 | 0 | x | None | Squamous, NOS |
| 77 | P | M | W | N/A | 74 | 2 | 2 | x | CNS | Squamous, NOS |
| 78 | N | F | W | upper lobe | 44 | 1 | 2 | x | Adjacent organs | Squamous, NOS |
| 79 | N | M | W | upper lobe | 57 | 3 | 0 | x | Adjacent organs | Squamous, NOS |
| 80 | N | M | W | lower lobe | 80 | 2 | 2 | x | None | Squamous, NOS |
| 81 | N | M | W | upper lobe | 60 | 1 | 2 | x | Adjacent organs | Squamous, NOS |
| 82 | N | M | W | lower lobe | 74 | 2 | 0 | x | Adjacent organs | Squamous, NOS |
| 83 | N | F | W | lower lobe | 65 | 2 | 1 | x | None | Squamous, NOS |
| 84 | P2 | M | W | lower lobe | 44 | 2 | 0 | x | None | Squamous, NOS |
| 85 | N | F | W | upper lobe | 82 | 2 | 2 | x | Adjacent organs | Squamous, NOS |
| 86 | N | F | W | lower lobe | 56 | 2 | 0 | x | None | Squamous, NOS |
| 87 | P2 | M | W | upper lobe | 76 | 2 | 2 | x | None | Squamous, NOS |
| 88 | P | M | W | upper lobe | 63 | 2 | 0 | x | None | Squamous, NOS |
| 89 | N | M | W | upper lobe | 57 | 2 | 1 | x | None | Squamous, NOS |
| 90 | N | M | W | upper lobe | 67 | 1 | 0 | x | None | Squamous, NOS |
| 91 | N | F | W | upper lobe | 41 | 2 | 0 | x | None | Squamous, NOS |
| 92 | N | F | W | lower lobe | 51 | 4 | 0 | x | None | Squamous, NOS |
| 93 | P | M | B | upper lobe | 75 | 2 | 1 | x | None | Squamous, NOS |
| 94 | N | F | W | upper lobe | 69 | 2 | 1 | x | None | Squamous, NOS |
| 95 | N | F | W | lower lobe | 68 | 1 | 0 | x | Adjacent organs | Squamous, NOS |
| 96 | N | F | W | lower lobe | 65 | 2 | 1 | x | None | Squamous, NOS |
| 97 | N | M | W | upper lobe | 58 | 1 | 0 | x | None | Squamous, NOS |
| 98 | P | M | W | upper lobe | 65 | 3 | 1 | 1 | Adjacent organs | Squamous, NOS |
| 99 | N | F | W | upper lobe | 60 | 2 | 0 | x | None | Squamous, NOS |
| 100 | N | F | W | lower lobe | 50 | 4 | 0 | x | Adjacent organs | Squamous, NOS |
| 101 | P | M | W | upper lobe | 65 | 1 | 0 | x | None | Squamous, NOS |
| 102 | N | M | W | upper lobe | 75 | 4 | 0 | x | Adjacent organs | Squamous, NOS |

N = negative
P = positive
P2 = Nested RT-PCR positive

TABLE 6

(liver cancer)

| Case | MF | sex | Race | Age | recur. | Patient Survival Days |
|---|---|---|---|---|---|---|
| 90 | P | M | W | 81 | NO | 426 |
| 120 | P | M | W | 51 | NO | 998 |
| 122 | P | M | W |  | Yes | N/A |
| 92 | N | M | W | 78 | NO | 1577 |
| 119 | P | M | W | 55 | Yes | 3894 |
| 121 | P | M | W | 51 | Yes | 968 |
| 163 | P | F | W | 68 | NO | 3519 |
| 162 | N | M | W | 86 | NO | 28 |
| 112 | N | F | W | 44 | Yes | 492 |
| 113 | N | M | W | 79 | NO | 43 |
| 135 | P | F | W | 74 | NO | 4037 |
| 95 | N | M | W | 76 | Yes | 927 |
| 94 | N | M | W | 88 | Yes | 900 |
| 117 | P | M | W | 60 | Yes | 515 |
| 140 | N | M | W | 85 | Yes | 740 |
| 110 | P | M | W | 73 | Yes | 1802 |
| 111 | N | M | W | 66 | Yes | 1115 |
| 134 | N | F | W | 39 | Yes | 199 |
| 136 | N | M | W | 89 | Yes | 173 |
| 138 | N | F | B | 70 | NO | 7485 |
| 114 | P | M | W | 76 | Yes | 194 |
| 141 | N | M | W | 84 | Yes | 1396 |
| 142 | N | M | B | 41 | NO | 28 |
| 137 | P | M | W | 61 | Yes | 9311 |
| 139 | N | M | W | 83 | NO | 878 |
| 96 | N | M | W | 83 | NO | 28 |
| 165 | N | M | W | 82 | Yes | 482 |
| 164 | N | M | W | 87 | NO | 214 |
| 109 | N | F | W | 59 | Yes | 756 |
| 159 | N | M | W | 76 | Yes | 1431 |
| 160 | N | M | W | 78 | Yes | 139 |
| 108 | N | M | W | 75 | Yes | 1416 |
| 152 | N | F | W | 75 | Yes | 276 |
| 115 | N | M | W | 66 | NO | 8783 |
| 146 | N | M | W | 85 | NO | 45 |
| 156 | N | M | W | 70 | NO | 489 |
| 157 | N | M | W | 84 | NO | 2954 |
| 151 | N | M | W | 80 | Yes | 265 |
| 149 | N | F | W | 67 | Yes | 1014 |
| 148 | N | M | W | 82 | NO | 19 |
| 81 | N | F | W | 81 | NO | 6737 |
| 154 | N | M | W | 78 | Yes | 394 |
| 178 | N | M | W | 61 | Yes | 856 |
| 153 | N | M | W | 83 | NO | 176 |
| 169 | N | M | W | 71 | Yes | 1776 |
| 88 | N | M | W | 82 | NO | 6326 |
| 89 | N | F | W | 63 | NO | 227 |
| 168 | N | M | W | 81 | Yes | 381 |
| 85 | N | M | W | 56 | Yes | 638 |
| 173 | N | M | A | 71 | Yes | 2435 |
| 87 | N | M | W | 69 | NO | 174 |
| 86 | N | F | W | 77 | NO | 3376 |
| 182 | N | M | W | 64 | NO | 40 |
| 179 | N | F | W | 84 | NO | 3019 |
| 99 | N | M | W | 77 | NO | 61 |
| 98 | N | M | W | 78 | NO | 3190 |
| 102 | N | M | W | 67 | NO | 4960 |
| 97 | N | M | W | 74 | Yes | 1695 |
| 177 | N | M | W | 70 | NO | 3835 |
| 2 | N | M | A | 63 | NO | 1500 |
| 184 | N | M | W | 66 | Yes | 678 |
| 7 | N | F | W |  | NO | N/A |
| 27 | N | f | W |  | NO | N/A |
| 6 | N | M | W | 74 | NO | 1473 |
| 12 | N | f | W |  | NO | N/A |
| 10 | N | f | W |  | NO | N/A |
| 23 | N | F | W | 67 | NO | 1317 |
| 17 | N | M | W | 57 | NO | 1365 |
| 28 | N | F | W |  | NO | N/A |
| 71 | N | M | W | 51 | NO | 792 |

N = negative
P = positive

TABLE 7

(prostate cancer)

| PROSTATE | MF | TNM | Reccur. | Gleason | Age | Race | PSA pre-operative |
|---|---|---|---|---|---|---|---|
| DB237 | N | T2bN0MX | y | 6.0 | 70s | W | 6.3 |
| FB120 | N | T3aN0MX | y | 7.0 | 60s | W | 61.1 |
| FB174 | N | T3aN0MX | y | 7.0 | 60s | W | 6.9 |
| FB183 | N | T2cN0MX | y | 7.0 | 60s | W | 9.7 |
| FB238 | P2 | T3bN0MX | y | 7.0 | 60s | W | 15.9 |
| FB421 | N | T3aN0MX | y | 7.0 | 60s | W | 4.5 |
| FB76 | N | T2c N0 MX | n | 7 | 60s | W | 6.53 |
| FB94 | N | T2cN0MX | y | 7.0 | 60s | W | 5.1 |
| GB195 | N | T2cN0MX | y | 7.0 | 60s | W | 10.1 |
| GB368 | P2 | T2c N0 MX | n | 7 | 60s | W | 6.53 |
| GB400 | N | T3bN0MX | y | 7.0 | 60s | W | 3.5 |
| HB021 | N | T2bN0MX | y | 6.0 | 50s | W | 5.9 |
| HB033 | N | T2cN0MX | n | 7.0 | 50s | W | 8.4 |
| HB207 | N | T3bN0MX | y | 9.0 | 60s | W | 6.3 |
| HB235 | N | T3bN1MX | y | 9.0 | 60s | W | 4.6 |
| HB261 | N | T3aN0MX | n | 7.0 | 50s | W | 5.4 |
| HB303 | P2 | T3a N0 MX | n | 7 | 60s | W | 5.5 |
| HB305 | P | T3bN0MX | y | 6.0 | 60s | W | 10.1 |
| HB327 | P | T2c N0 MX | n | 8 | 60s | W | 9.5 |
| HB340 | N | T2c N0 MX | n | 7 | 60s | W | 9.57 |
| HB466 | N | T2aN0MX | n | 7.0 | 60s | W | 4.0 |
| HB48 | N | T2aN0MX | n | 6.0 | 60s | W | 4.5 |
| HB492 | N | T2c N0 MX | n | 7 | 60s | W | 7.4 |
| HB504 | N | T3bN0MX | y | 8.0 | 50s | U | 70.0 |
| HB526 | N | T3bN0MX | y | 6.0 | 60s | W | 8.7 |
| HB568 | P | T3bN0MX | y | 7.0 | 60s | W | 4.4 |
| HB591 | P | T3bN1MX | y | 7.0 | 60s | W | 13.6 |
| HB603 | N | T3aN1MX | y | 7.0 | 60s | W | 8.4 |
| IB112 | N | T3aN0MX | y | 7.0 | 60s | U | 4.7 |
| IB134 | N | T3bN0MX | n | 9.0 | 70s | W | 15.7 |

TABLE 7-continued (prostate cancer)

| PROSTATE | MF | TNM | Reccur. | Gleason | Age | Race | PSA pre-operative |
|---|---|---|---|---|---|---|---|
| IB136 | N | T3bN1MX | y | 8.0 | 50s | W | 19.6 |
| IB273 | N | T2bN0MX | y | 7.0 | 50s | W | 4.3 |
| IB289 | N | T2a N0 MX | n | 7 | 70s | W | 9.96 |
| IB298 | N | T3bN0MX | y | 7.0 | 60s | W | 5.3 |
| IB362 | N | p3aN0MX | y | 7.0 | 60s | W | 4.6 |
| IB483 | N | T2bN0MX | y | 7.0 | 50s | W | 5.2 |
| JB154 | N | T3aN0MX | y | 9.0 | 60 | W | 4.6 |
| JB197 | N | T3bN0MX | y | 7.0 | 50s | W | 11.2 |
| JB426 | N | T2cN0MX | y | 7 | 60s | W | 5.7 |
| JB770 | N | T2cN0MX | y | 8 | 60s | W | 2.38 |
| PR018 | N | T3aN0MX | y | 7 | 60s | W | 9 |
| PR079 | N | T3aN0MX | y | 7.0 | 60s | W | 5.1 |
| PR236 | N | T3bN0MX | y | 10.0 | 60s | W | 9.9 |
| PR300 | N | T3bN1MX | y | 7.0 | 50s | W | 20.3 |
| PR303 | N | T3bN0MX | y | 6.0 | 70s | W | 10.5 |
| PR306 | N | T3bN0MX | y | 7.0 | 60s | W | 11.5 |
| PR310 | N | T3bN0MX | y | 7.0 | 60s | W | 5.1 |
| PR434 | N | T3aN0MX | y | 7.0 | 60s | W | 6.4 |
| PR521 | N | T2bN0MX | y | 7.0 | 50s | W | 6.4 |
| PR534 | N | T2b N0 MX | n | 6 | 60s | W | 8.4 |
| PR79 | N | T3aN0MX | y | 7.0 | 60s | W | 5.1 |
| TP08-S0226 | N | T4N1MX | y | 9.0 | 60s | W | 8.5 |
| TP08-S0530 | N | T3bN0MX | y | 7.0 | 60s | W | 11.1 |
| TP08-S0542 | N | T2cN0MX | y | 7.0 | 50s | W | 4.3 |
| TP08-S0721 | N | T3bN1MX | y | 10 | 50s | W | 29.3 |
| TP09-S0006 | N | T3bN1MX | y | 8 | 50s | W | 4.9 |
| TP09-S0420 | N | T3bN1MX | y | 7 | 50s | W | 14.6 |
| TP09-S0704 | N | T4 N1 MX | y | 9 | 60s | W | 55 |
| TP09-S0721 | N | T3bN1MX | y | 10.0 | 50s | W | 29.3 |
| TP10-S0564 | N | T3aN1MX | y | 7.0 | 50s | W | 3.8 |
| TP10-S0565 | N | T3bN1MX | y | 9 | 60s | W | 9.8 |
| TP10-S0638 | N | T3bN1MX | y | 10 | 50s | W | 9.17 |
| TP10-S0640 | N | T3bN1MX | y | 10 | 60s | W | 13.1 |
| TP10-S0703 | N | T3bN1MX | y | 8.0 | 60s | W | 7.2 |
| TP10-S0704 | N | T3aN1MX | y | 9 | 60s | W | 4.5 |
| TP10-S093 | N | T3aN0MX | y | 7 | 60s | W | 4.1 |
| TP10-S0964 | N | T3bN1MX | y | 9 | 60s | w | 8.9 |
| TP10-S1113 | N | T3aN1MX | y | 9.0 | 60s | W | 84.7 |
| TP11-S0155 | N | T3bN1MX | y | 8.0 | 50s | W | 7.0 |
| TP11-S0272 | N | T3aN1MX | y | 7.0 | 60s | W | 4.2 |
| TP11-S0354 | N | T3aN1MX | y | 8.0 | 60s | W | 6.4 |
| TP11-S0463 | N | T3bN1MX | y | 7.0 | 60s | W | 6.4 |
| TP13-0666 | N | T2a N0 MX | n | 6 | 50s | W | 6.9 |
| TP12-S1030 | N | T2c N0 MX | n | 7 | 50s | W | 3.4 |
| TP12-S1060 | N | T2c N0 MX | n | 7 | 60s | AA | 1.85 |
| TP12-S0048 | N | T3a N0 MX | n | 8 | 70s | w | 7.9 |
| TP12-S0102 | N | T3a N1 MX | n | 7 | 60s | W | 10.7 |
| TP12-S0114 | N | T3bN1MX | y | 8.0 | 60s | W | 10.8 |
| TP12-S0246 | N | T2c N1 MX | n | 7 | 50s | W | 3.9 |
| TP12-S0337 | N | T2a N1 MX | y | 7 | 60s | W | 13.8 |
| TP12-S0340 | N | T3b N1 MX | n | 9 | 50s | W | 5.5 |
| TP12-S0373 | N | T3aN1MX | y | 7.0 | 60s | W | 4.4 |
| TP12-S0456 | N | T3a N1 MX | n | 8 | 60s | W | 6 |
| TP12-S0608 | N | T3a N1 MX | y | 8 | 60s | W | 20.3 |
| TP12-S0624 | N | T3b N1 MX | n | 7 | 70s | W | 3.3 |
| TP12-S0765 | N | T3a N0 MX | n | 7 | 60s | W | 4.98 |
| TP12-S0786 | N | T3b N1 MX | y | 7 | 60s | W | 4.5 |
| TP12-S0790 | N | T3a N0 MX | y | 7 | 60s | W | 24.2 |
| TP12-S0795 | N | T3a N0 MX | n | 7 | 60s | W | 24.2 |
| TP12-S0805 | N | T3a N1 MX | n | 7 | 60s | W | 7.6 |
| TP12-S0816 | N | T3a N0 MX | n | 7 | 60s | W | 6.46 |
| TP12-S0914 | N | T2a N1 MX | n | 7 | 60s | W | 7 |
| TP12-S0915 | N | T3a NX MX | n | 7 | 60s | W | 5 |
| TP12-S0928 | N | T3a N0 MX | n | 7 | 70s | W | 5.3 |
| TP12-S0943 | N | T3a N1 MX | y | 9 | 50s | W | 10.3 |
| TP12-S0954 | N | T3b N0 MX | y | 7 | 60s | W | 15.7 |
| TP12-S0967 | N | T3a N0 MX | n | 7 | 60s | W | 6.03 |
| TP12-S0981 | N | T3b N0 MX | n | 7 | 60s | W | 56.4 |
| TP12-S1032 | N | T3a N0 MX | n | 7 | 60s | W | 9.2 |
| TP12-S1059 | P | T3a N0 MX | y | 8 | 50s | W | 10.6 |
| TP12-S1189 | N | T2c N0 MX | n | 7 | 60s | W | 18.49 |
| TP12-S1197 | N | T2c N0 MX | n | 7 | 60s | W | 5.02 |
| TP12-S1224 | N | T2c N0 MX | n | 7 | 60s | W | 4.9 |
| TP12-S1303 | N | T3b N1 MX | y | 9 | 60s | W | 9.87 |
| Tp12-S1308 | N | T3a N1 MX | y | 9 | 60s | W | 5.84 |
| TP12-S1309 | N | T3a N1 MX | n | 9 | 60s | W | 3.1 |

TABLE 7-continued (prostate cancer)

| PROSTATE | MF | TNM | Reccur. | Gleason | Age | Race | PSA pre-operative |
|---|---|---|---|---|---|---|---|
| TP12-SO048 | N | T3a N0 MX | n | 8 | 60s | W | 7.9 |
| TP12-SO246 | N | T2c N1 MX | n | 7 | 50s | W | 3.9 |
| TP12-SO337 | N | T2a N1 MX | y | 7 | 60s | W | 13.8 |
| TP12-SO340 | N | T3b N1 MX | y | 9 | 50s | W | 5.5 |
| TP12-SO466 | N | T3b N1 MX | y | 8 | 60s | W | 6.1 |
| TP12-SO608 | N | T3a N1 MX | y | 8 | 60s | W | 20.3 |
| TP13-S0035 | N | T3b N1 MX | n | 7 | 60s | AA | 21.8 |
| TP13-S0043 | N | T3a N0 MX | y | 8 | 60s | W | 22 |
| TP13-S0109 | N | T3b N1 MX | y | 8 | 70s | W | 21.46 |
| TP13-S0248 | N | T3b N1 MX | y | 8 | 60s | W | 6.8 |
| TP13-S0314 | N | T3a N0 MX | y | 7 | 60s | W | 3.6 |
| TP13-S0370 | N | T3a N1 MX | n | 8 | 60s | W | 5.3 |
| TP13-S0438 | N | T3a N1 MX | n | 9 | 60s | W | 4.6 |
| TP13-S0456 | N | T3a N0 MX | y | 9 | 50s | W | 29.9 |
| TP13-S0464 | N | T3b N1 MX | y | 9 | 50s | W | 10 |
| TP13-S0546 | N | T3b N1 MX | y | 7 | 60s | W | 9.77 |
| TP13-S0571 | N | T3b N1 MX | y | 9 | 60s | W | 9 |
| TP13-S0573 | N | T3b N1 MX | y | 8 | 50s | W | 13.9 |
| TP13-S0582 | N | T2c N1 MX | y | 8 | 60s | W | 2.57 |
| TP13-S0657 | N | T3b N1 MX | y | 8 | 60s | W | 40 |
| TP13-S0686 | N | T3b N1 MX | y | 9 | 50s | W | 9.3 |
| TP13-S0698 | N | T4 N1 MX | y | 9 | 60s | W | 63.6 |
| TP14-S0008 | N | T3a N1 MX | y | 7 | 50s | W | 6.4 |
| TP14-S0087 | N | T3b N1 MX | y | 7 | 60s | W | 8 |
| TP14-S0093 | N | T3b N1 MX | y | 9 | 60s | W | 8.28 |
| TP14-S0128 | N | T3a N1 MX | y | 9 | 50s | W | 4.87 |
| TP14-S0145 | N | T3a N1 MX | n | 7 | 40s | W | 15.19 |
| TP14-S0159 | N | T2c N0 MX | y | 9 | 60s | W | 45.9 |
| TP14-S0221 | N | T3a N1 MX | y | 8 | 60s | W | 36.2 |
| TP14-S0228 | N | T3a N1 MX | y | 7 | 60s | W | 5.17 |
| TP13-S0570 | N | T3b N1 MX | y | 9 | 60s | W | 7.02 |
| 99-7270 | N | T3BN1MX | n | 9.0 | 70s | W | 15.9 |
| 99-678 | N | T3bN0MX | n | 9 | 70s | W | 10.8 |
| 159T | P | T2cN0MX | y | 8 | 60s | W | 2.18 |
| 158T | N | T3aN0MX | y | 7 | 60s | W | 4.2 |
| 165T | N | T3bN1MX | y | 10 | 50s | W | 19.3 |
| 171T | N | T3bN1MX | y | 10 | 50s | W | 10.17 |
| 49T | N | T3bN1MX | y | 7 | 50s | W | 13.6 |
| 184-33 | N | T2bN0MX | N/A | N/A | N/A | N/A | N/A |
| 83-2972 | N | T3aN0MX | N/A | N/A | N/A | N/A | N/A |
| 30-994308 | N | T3bN0MX | N/A | N/A | N/A | N/A | N/A |
| 34 T | N | T2cN0MX | N/A | N/A | N/A | N/A | N/A |
| 3B 82-8142 | N | T2cN0MX | N/A | N/A | N/A | N/A | N/A |
| 4A 85-5327 | N | T3aN0MX | N/A | N/A | N/A | N/A | N/A |
| 5A-84876 | N | T3aN0MX | N/A | N/A | N/A | N/A | N/A |
| 5J 87-12362 | N | T3bN0MX | N/A | N/A | N/A | N/A | N/A |
| 86-3176 5L | N | T3bN1MX | N/A | N/A | N/A | N/A | N/A |
| 8Q-98-12033 | N | T3bN0MX | N/A | N/A | N/A | N/A | N/A |
| 98-11462 T | N | T3bN0MX | N/A | N/A | N/A | N/A | N/A |
| 98-13745 T | N | T3bN0MX | N/A | N/A | N/A | N/A | N/A |
| 98-14481 | N | T3aN0MX | N/A | N/A | N/A | N/A | N/A |
| 98-25313 T | N | T2bN0MX | N/A | N/A | N/A | N/A | N/A |
| 98-2644 T | N | T2bN0MX | N/A | N/A | N/A | N/A | N/A |
| 98-2671 T | N | T3aN0MX | N/A | N/A | N/A | N/A | N/A |
| 98-28278 T | N | T4N1MX | N/A | N/A | N/A | N/A | N/A |
| 98-29671 T | N | T3bN0MX | N/A | N/A | N/A | N/A | N/A |
| 98-6647 T | N | T2cN0MX | N/A | N/A | N/A | N/A | N/A |
| 98-8432 T | N | T3bN1MX | N/A | N/A | N/A | N/A | N/A |
| 98-9122 T | N | T3bN1MX | N/A | N/A | N/A | N/A | N/A |
| 99-1199 | N | T3bN1MX | N/A | N/A | N/A | N/A | N/A |
| 99-1199 T | N | T4 N1 MX | N/A | N/A | N/A | N/A | N/A |
| 99-15733 T | N | T3bN1MX | N/A | N/A | N/A | N/A | N/A |
| 99-15922 T | N | T3aN1MX | N/A | N/A | N/A | N/A | N/A |
| 99-16464 T | N | T3bN1MX | N/A | N/A | N/A | N/A | N/A |
| 99-16947 T | N | T3bN1MX | N/A | N/A | N/A | N/A | N/A |
| 99-19381 T | N | T3bN1MX | N/A | N/A | N/A | N/A | N/A |
| 99-19425 T | N | T3bN1MX | N/A | N/A | N/A | N/A | N/A |
| 99-4308 T | N | T3aN1MX | N/A | N/A | N/A | N/A | N/A |
| 99-4336 T | N | T3aN0MX | N/A | N/A | N/A | N/A | N/A |
| 99-5396 T | N | T3bN1MX | N/A | N/A | N/A | N/A | N/A |
| 99-6837 T | N | T3aN1MX | N/A | N/A | N/A | N/A | N/A |
| 99-7221 T | N | T3bN1MX | N/A | N/A | N/A | N/A | N/A |
| 99-7504 T | N | T3aN1MX | N/A | N/A | N/A | N/A | N/A |
| 99-8629 T | N | T3aN1MX | N/A | N/A | N/A | N/A | N/A |
| 99-8741 T | N | T3bN1MX | N/A | N/A | N/A | N/A | N/A |
| DU 92-17293 | N | T2a N0 MX | N/A | N/A | N/A | N/A | N/A |

TABLE 7-continued (prostate cancer)

| PROSTATE | MF | TNM | Reccur. | Gleason | Age | Race | PSA pre-operative |
|---|---|---|---|---|---|---|---|
| DU 92-17293 | N | T2c N0 MX | N/A | N/A | N/A | N/A | N/A |
| ER1 8713205 | N | T2c N0 MX | N/A | N/A | N/A | N/A | N/A |
| H 84-9731 | N | T3a N0 MX | N/A | N/A | N/A | N/A | N/A |
| H S94-12443 | N | T3a N1 MX | N/A | N/A | N/A | N/A | N/A |
| IB110 T | N | T3bN1MX | N/A | N/A | N/A | N/A | N/A |
| IB111 T | N | T2c N1 MX | N/A | N/A | N/A | N/A | N/A |
| IB180 T | N | T2a N1 MX | N/A | N/A | N/A | N/A | N/A |
| IB378 T | N | T3b N1 MX | N/A | N/A | N/A | N/A | N/A |
| IB071 T | N | T3aN1MX | N/A | N/A | N/A | N/A | N/A |
| R10 | N | T3a N1 MX | N/A | N/A | N/A | N/A | N/A |
| R13 | N | T3a N1 MX | N/A | N/A | N/A | N/A | N/A |
| R13 | N | T3b N1 MX | N/A | N/A | N/A | N/A | N/A |
| R16 | N | T3a N0 MX | N/A | N/A | N/A | N/A | N/A |
| R18 | N | T3b N1 MX | N/A | N/A | N/A | N/A | N/A |
| R19 | N | T3a N0 MX | N/A | N/A | N/A | N/A | N/A |
| R19 | N | T3a N0 MX | N/A | N/A | N/A | N/A | N/A |
| R26 | N | T3a N1 MX | N/A | N/A | N/A | N/A | N/A |
| R3 | N | T3a N0 MX | N/A | N/A | N/A | N/A | N/A |
| R57T | N | T2a N1 MX | N/A | N/A | N/A | N/A | N/A |
| R59T | N | T3a NX MX | N/A | N/A | N/A | N/A | N/A |
| R6TT | N | T3a N0 MX | N/A | N/A | N/A | N/A | N/A |
| 19 | N | T3aN1M0 | y | 9 | 50s | W | 4.42 |
| 252 | N | T4N0M0 | y | 7 | 60s | W | 42 |
| 265 | N | T2bN0M0 | y | 8 | 50s | B | 4.53 |
| 452 | N | T2bN0M0 | y | 7 | 60s | W | 5.12 |
| 366 | N | T3bN0M0 | y | 7 | 50s | B | 4.01 |
| 538 | P | T2bN0M0 | y | 7 | 60s | W | 10.7 |
| 47 | P | T2bN0M0 | y | 7 | 50s | W | 9.92 |
| 97 | N | T2bN0M0 | y | 7 | 50s | W | 4.1 |
| 370 | N | T3bN1M0 | y | 8 | 50s | W | 10.76 |
| 405 | N | T2bN1M0 | y | 7 | 60s | W | 15.44 |
| 448 | N | T3bN0M0 | y | 7 | 60s | W | 7.1 |
| 485 | P | T2bN0M0 | y | 7 | 60s | W | 5.91 |
| 498 | N | T2bN0M0 | ND | 6 | 50s | W | 4.68 |
| 551 | N | T2bN0M0 | ND | 6 | 40s | W | 4.8 |
| 494 | N | T2bN0M0 | ND | 7 | 60s | W | 2.38 |
| 629 | N | T2bN0M0 | ND | 6 | 70s | B | 3.2 |
| 643 | N | T2bN0M0 | ND | 7 | 60s | W | 7.16 |
| 646 | N | T2bN0M0 | ND | 7 | 60s | W | 4.9 |
| 473 | N | T2bN0M0 | ND | 7 | 60s | A | 4.64 |
| 470 | N | T2bN0M0 | ND | 7 | 70s | W | 6.8 |
| 482 | N | T2bN0M0 | ND | 6 | 70s | W | 2.84 |
| 15 | N | T2bN0M0 | n | 6 | 40s | W | 5.12 |
| 501 | N | T2bN0M0 | n | 7 | 60s | W | 3.93 |
| 274 | P | T2bN0M0 | n | 7 | 60s | W | 3.9 |
| 343 | N | T2bN0M0 | n | 6 | 60s | W | 10.77 |
| 599 | N | T2bN0M0 | n | 7 | 40s | W | 8.9 |
| 45 | N | T2bN0M0 | n | 7 | 50s | W | 6.58 |
| 86 | N | T2bN0M0 | n | 7 | 60s | W | 2.1 |
| 99 | N | T2bN0M0 | n | 7 | 70s | H | 6.26 |
| 85 | N | T2aN0M0 | n | 7 | 40s | W | 4.8 |
| 0361 TP | N | T1CN1Mx | yes | 6 | 60s | N/A | 12 |
| 0404 TP | N | T3aN0Mx | yes | 7 | 50s | N/A | 2.9 |
| 0425TP | N | T2AN0MX | yes | 7 | 50s | N/A | 5.1 |
| 0428 TP | N | T2AN1MX | yes | 9 | 60s | N/A | 4.13 |
| 0451 TP | N | T1CN0Mx | yes | 6 | 60s | N/A | 5.2 |
| 0506TP | P | T1CN0Mx | yes | 7 | 60s | N/A | 4.95 |
| 0531TP | N | T1CN1MX | yes | 7 | 40s | N/A | 42 |
| 0558 TP | N | N/A | yes | 7 | 40s | N/A | 5 |
| 0611TP | N | N/A | yes | 9 | 60s | N/A | 6.3 |
| 0633TP | N | N/A | yes | 77 | 60s | N/A | 4.3 |
| 0666 TP | N | T2BN0MX | yes | 7 | 70s | N/A | 7.9 |
| 0817TP | N | T2CN0MX | yes | 7 | 60s | N/A | 5.6 |
| 4706TP | N | T3BN0Mx | yes | 7 | 60s | N/A | 6.7 |
| 5565TP | N | N/A | ND | 8 | NA | N/A | N/A |
| 7225TP | N | N/A | ND | 10 | NA | N/A | N/A |
| 7519TP | N | T2cN0Mx | ND | 9 | 60s | N/A | 4 |
| 7653TP | N | T3bN0Mx | ND | 9 | 40s | N/A | 27 |
| 7677TP | N | N/A | ND | 8 | 50s | N/A | N/A |
| 7682TP | N | T3bN0Mx | ND | 9 | 50s | N/A | 3.7 |
| 7967TP | N | N/A | ND | 9 | N/A | N/A | N/A |
| 8099TP | N | N/A | ND | 8 | 50s | N/A | N/A |
| 0402 TP | N | T1CN0Mx | no | 7 | 50s | N/A | 4.5 |
| 0405 TP | N | T3aN0Mx | no | 7 | 70s | N/A | 5 |
| 0505TP | N | T1CN0Mx | no | 8 | 40s | N/A | 7 |

TABLE 7-continued (prostate cancer)

| PROSTATE | MF | TNM | Reccur. | Gleason | Age | Race | PSA pre-operative |
|---|---|---|---|---|---|---|---|
| 0650 TP | N | T2BN0MX | no | 6 | 50s | N/A | 2.5 |
| 0735TP | N | T3AN0Mx | no | 7 | 60s | N/A | 4.2 |
| 0812TP | N | T2CN0Mx | no | 7 | 60s | N/A | 5 |
| 0827TP | N | T2CN0Mx | no | 7 | 60s | N/A | N/A |
| 0830TP | N | T2CN0Mx | no | 7 | 60s | N/A | 4.47 |
| 4279TP | N | T2AN0Mx | no | 6 | 60s | N/A | 4 |
| 4747TP | N | T2CN0Mx | no | 7 | 50s | N/A | 5.7 |
| 4775TP | N | T3AN0Mx | no | 7 | 50s | N/A | 5 |
| 4987TP | N | T2CN0Mx | no | 7 | 50s | N/A | 5.4 |
| 5187TP | N | T2CN0Mx | no | 7 | 60s | N/A | 4.6 |
| 5223TP | N | T2CN0Mx | no | 6 | 50s | N/A | 4.1 |
| 6216TP | N | T2CN0Mx | no | 7 | 60s | N/A | 4.6 |

N = negative
P = positive
P2 = positive in nested RT-PCR

TABLE 8

(Ovarian cancer)

| Anon# | MF | Age | Grade | pT | pN | pM | Recur (mon) | recurr. Site | Surv since 1st Recur |
|---|---|---|---|---|---|---|---|---|---|
| TB15-127 | N | 90 | Grade I | 1A | X | 0 | 0 | None | 0 |
| TB15-128 | N | 59 | ND | 3B | 0 | 0 | 0 | None | 0 |
| TB15-129 | N | 41 | ND | 1 | 0 | 0 | 0 | None | 0 |
| TB15-130 | N | 83 | Grade I | 2A | 0 | 0 | 0 | None | 0 |
| TB15-131 | N | 61 | Grade III | 1C | 0 | 0 | 0 | None | 0 |
| TB15-132 | N | 70 | Grade III | 2C | 0 | 0 | 0 | None | 0 |
| TB15-133 | N | 44 | Grade I | 1C | 0 | X | 0 | None | 0 |
| TB15-134 | N | 42 | Grade III | 2A | 0 | X | 0 | None | 0 |
| TB15-135 | N | 61 | Grade II | 1C | 0 | 0 | 0 | None | 0 |
| TB15-136 | N | 57 | Grade II | 1A | 0 | 0 | 0 | None | 0 |
| TB15-137 | N | 52 | Grade III | 1C | 0 | 0 | 51 | None | 33 |
| TB15-138 | N | 35 | Grade IV | 1C | 0 | 0 | 0 | None | 0 |
| TB15-139 | N | 55 | Grade I | 3B | 0 | X | 0 | None | 0 |
| TB15-140 | N | 56 | Grade I | 1C | 0 | X | 0 | None | 0 |
| TB15-141 | N | 42 | Grade III | 1C | 0 | 0 | 0 | None | 0 |
| TB15-142 | N | 44 | Grade II | 1B | 0 | X | 0 | None | 0 |
| TB15-143 | N | 58 | Grade III | 1C | 0 | 0 | 0 | None | 0 |
| TB15-144 | N | 50 | ND | 1A | 0 | 0 | 0 | None | 0 |
| TB15-145 | N | 45 | Grade IV | 1C | 0 | X | 0 | None | 0 |
| TB15-146 | N | 49 | Grade III | 1C | 0 | 0 | 0 | None | 0 |
| TB15-147 | N | 55 | Grade III | 3B | 0 | 0 | 0 | None | 0 |
| TB15-148 | N | 44 | Grade III | 1C | 0 | X | 0 | None | 0 |
| TB15-149 | N | 69 | Grade II | 3B | 0 |  | 0 | None | 0 |
| TB15-150 | N | 63 | Grade III | 3C | X | X | 0 | None | 0 |
| TB15-151 | N | 42 | Grade II | 1A | 0 | 0 | 0 | None | 0 |
| TB15-152 | N | 50 | Grade III | 1A | 0 | 0 | 0 | None | 0 |
| TB15-153 | N | 75 | Grade I | 1A | 0 | 0 | 0 | None | 0 |
| TB15-154 | N | 59 | Grade III | 2A | 0 | 0 | 0 | None | 0 |
| TB15-156 | N | 42 | Grade II | 1C | 0 | 0 | 0 | None | 0 |
| TB15-157 | N | 50 | ND | 1C | 0 | 0 | 0 | None | 0 |
| TB15-180 | N | 57 | ND | 3C | 1 | 0 | 0 | None | 0 |
| TB15-181 | N | 56 | Grade III | 3C | 1 | X | 0 | None | 0 |
| TB15-182 | N | 68 | ND | 3C | 1 | 0 | 10 | Lymph nodes | 29 |
| TB15-183 | N | 81 | Grade III | 3C | 1 | 0 | 0 | None | 0 |
| TB15-184 | N | 51 | Grade III | 3 | 1 | 1 | 16 | None | 59 |
| TB15-185 | N | 51 | Grade II | 3C | 1 | 1 | 0 | None | 0 |
| TB15-186 | N | 57 | Grade III | 3C | X | 1 | 0 | Pleura | 0 |
| TB15-187 | N | 41 | Grade III | 3C | 1 | 0 | 0 | None | 0 |
| TB15-188 | N | 70 | Grade III | 3C | X | 1 | 0 | Liver | 0 |
| TB15-189 | N | 66 | Grade IV | 3C | 1 | 0 | 36 | generalized | 21 |
| TB15-190 | N | 65 | Grade III | 3C | 1 | 0 | 0 | None | 0 |
| TB15-191 | N | 61 | Grade III | 3C | 0 | 1 | 19 | Peritoneum | 15 |
| TB15-192 | N | 52 | ND | 3C | 0 | 1 | 0 | Pleura | 0 |
| TB15-193 | P | 70 | Grade III | 3C | 0 | 0 | 18 | Lymph nodes | 20 |
| TB15-194 | N | 50 | Grade IV | 3C | 1 | 0 | 0 | None | 0 |
| TB15-195 | N | 69 | Grade III | 3C | 0 | 0 | 8 | generalized | 1 |
| TB15-196 | N | 57 | Grade III | 3C | 1 | 0 | 8 | None | 62 |
| TB15-197 | N | 61 | Grade III | 3C | 1 | 0 | 47 | generalized | 11 |
| TB15-198 | N | 48 | Grade III | 3C | 1 | 0 | 0 | None | 0 |
| TB15-199 | N | 78 | Grade III | 3C | 1 | 1 | 9 | None | 21 |

TABLE 8-continued (Ovarian cancer)

| Anon# | MF | Age | Grade | pT | pN | pM | Recur (mon) | recurr. Site | Surv since 1st Recur |
|---|---|---|---|---|---|---|---|---|---|
| TB15-207 | N | 64 | Grade II | 3C | 0 | 1 | 0 | None | 0 |
| TB15-208 | N | 52 | Grade III | 3C | 1 | 1 | 0 | None | 0 |
| TB15-209 | N | 66 | Grade III | 3C | 0 | 0 | 34 | None | 47 |
| TB15-210 | N | 71 | Grade III | 3C | 1 | 0 | 0 | None | 0 |
| TB15-211 | N | 78 | Grade III | 3C |   | 1 | 0 | None | 0 |
| TB15-212 | N | 79 | Grade III | 3C | 1 | 1 | 0 | None | 0 |
| TB15-213 | N | 77 | Grade III | 3C | X | 1 | 0 | None | 0 |
| TB15-214 | N | 72 | Grade III | 3C | 1 | 0 | 6 | None | 5 |
| TB15-215 | N | 68 | Grade III | 3C | 0 | 1 | 0 | None | 0 |
| TB15-216 | N | 69 | ND | 3C | 1 | 0 | 3 | generalized | 82 |

N = negative
P = positive
P2 = positive in nested RT-PCR

TABLE 9

(Esophageal adenocarcinoma)

| Esophagus cancer # | | MAN2A1-FER status |
|---|---|---|
| 11 | 994,995 TE | P |
| 12 | 15995 TE | P2 |
| 13 | 16115 TE | P2 |
| 14 | 18787 TE | N |
| 15 | 41791 TE | N |
| 16 | 40320 TE | P2 |
| 17 | 40498 TE | P |
| 18 | 41081 TE | P2 |
| 19 | 15938 TE | N |
| 20 | 16806 TE | N |
| 21 | 18734 TE | N |
| 22 | 19061 TE | P2 |
| 23 | 43526 TE | N |
| 24 | 44636 TE | N |
| 25 | 43872 TE | N |
| 26 | 43888 TE | N |
| 27 | 41285 TE | N |
| 28 | 41701 TE | N |
| 29 | 41744 TE | N |
| 30 | 42709 TE | P2 |
| 31 | 44231 TE | N |
| 32 | 44014 TE | N |
| 33 | 44267 TE | N |
| 34 | 43075 TE | N |
| 35 | 40776 TE | N |

N = negative
P = positive
P2 = positive in nested RT-PCR

TABLE 10

(Glioblastoma)

| case# | area | dx | MF | race | sex | age at dx yr | age at death | survival days |
|---|---|---|---|---|---|---|---|---|
| 1 | fr, r | gbm | n | w | f | 43.22466 | 43.909589 | 250 |
| 2 | occ, l | gbm | n | w | m | 42.72877 | 43.4438356 | 261 |
| 3 | temp, r | gbm | n | w | m | 56.28493 | 57.8958904 | 588 |
| 4 | fr, l | gbm | n | aa | m | 47.24932 | 49.0082192 | 642 |
| 5 | temp-par, l | gbm | n | w | m | 45.39726 | 47.2520548 | 677 |
| 6 | temp, l | gbm | n | w | m | 42.63562 | 44.5260274 | 690 |
| 7 | temp, r | gbm | n | w | f | 53.13699 | 56.1671233 | 1106 |
| 8 | par, r | gbm | n | w | f | 44.57534 | 52.260274 | 2805 |
| 9 | x | gbm |   | w | f | 77.08493 | 85.2410959 | 2977 |
| 10 | x | gbm | p | w | f | 65.21096 | 66.3013699 | 398 |
| 11 | x | gbm | p | w | f | 69.95616 | 71.7643836 | 660 |
| 12 | x | gbm, r/r | p | w | f | 63.72877 | 64.9835616 | 458 |
| 13 | x | gbm | p | w | m | 78.35616 | 78.5506849 | 71 |
| 14 | x | gbm | p | w | m | 56.19726 | 57.060274 | 315 |
| 15 | x | gbm | p | w | f | 85.03288 | 86.0191781 | 360 |
| 16 | x | gbm | p2 | w | f | 60.35068 | 68.3342466 | 2914 |
| 17 | x | gbm | p2 | w | m | 63.48767 | 64.8164384 | 485 |
| 18 | temp, r | gbm | n | aa | m | 55.30685 | 55.5369863 | 11 |
| 19 | occ, r | gbm | n | w | f | 69.27945 | 70.2712329 | 362 |
| 20 | x | gbm | P2 | w | m | 65.76164 | 66.0712329 | 113 |
| 21 | x | gbm | P2 | w | m | 42.80822 | 43.0712329 | 96 |
| 22 | temp, r | gbm | n | w | f | 61.97534 | 62.9972603 | 373 |
| 23 | temp, l | gbm | n | w | m | 69.16986 | 70.1232877 | 348 |
| 24 | x | gbm | n | w | m | 48.31781 | 49.1835616 | 316 |
| 25 | x | gbm | n | w | m | 43.35616 | 44.0027397 | 236 |

TABLE 10-continued (Glioblastoma)

| case# | area | dx | MF | race | sex | age at dx yr | age at death | survival days |
|---|---|---|---|---|---|---|---|---|
| 26 | fr, l | gbm | n | w | m | 70.54247 | 70.6493151 | 39 |
| 27 | tem-par, l | gbm | n | w | m | 64.46301 | 67.2109589 | 1003 |
| 28 | x | gbm, r/r | n | w | m | 57.19726 | 57.6136986 | 152 |
| 29 | temp, l | gbm | n | w | m | 53.35616 | 59.6657534 | 2303 |
| 30 | par, r | gbm | n | w | f | 75.75616 | 77.6164384 | 679 |
| 31 | temp, r | gbm | n | w | m | 50.99178 | 52.1863014 | 436 |
| 32 | x | gbm, r/r | n | w | m | 67.80548 | 67.9890411 | 67 |
| 33 | x | gbm, r/r | n | w | f | 46.44384 | 46.7260274 | 103 |
| 34 | par, r | gbm | n | w | m | 37.30411 | 40.0630137 | 1007 |
| 35 | fr, l | gbm | n | w | f | 69.83288 | 70.3945205 | 205 |
| 36 | fr, l | gbm | n | w | m | 73.86027 | 75.0849315 | 447 |
| 37 | par-occ, r | gbm | n | w | f | 78.1863 | 79.1287671 | 344 |
| 38 | x | gbm | n | w | m | 33.4411 | 34.3972603 | 349 |
| 39 | x | gbm | n | w-mw | f | 78.3589 | 89.1452055 | 3937 |
| 40 | x | gbm, r/r | n | w | m | 58.12329 | 58.5972603 | 173 |
| 41 | temp, l | gbm | n | w | m | 65.86849 | 66.1643836 | 108 |
| 42 | par, l | gbm | n | w | f | 69.53973 | 76.2328767 | 2443 |
| 43 | x | gbm | n | w | f | 60.40548 | 62.2547945 | 675 |
| 44 | temp, l | gbm | n | w-pv | f | 75.66027 | 76.4876712 | 302 |
| 45 | temp, l | gbm, r/r | n | ns | m | 64.83014 | 69.0767123 | 1550 |
| 46 | fr, l | gbm | n | ns | f | 62.4411 | 62.9561644 | 188 |
| 47 | temp, l | gbm | n | w | m | 44.36438 | 45.5753425 | 442 |
| 48 | x | gbm | n | me | m | 44.4274 | 45.8356164 | 514 |
| 49 | x | gbm | n | w | m | 52.15342 | 52.4164384 | 96 |
| 50 | x | gbm | n | w | f | 56.73151 | 57.9260274 | 436 |
| 51 | x | gbm | n | w | m | 56.77808 | 57.0958904 | 116 |
| 52 | x | gbm | n | w | m | 75.72055 | 75.9205479 | 73 |
| 53 | x | gbm, r/r | n | w | m | 55.65479 | 55.8575342 | 74 |
| 54 | x | gbm | n | w | m | 55.70411 | 56.0958904 | 143 |
| 55 | x | gbm | n | w | f | 75.72055 | 76.6684932 | 346 |
| 56 | x | gbm | n | w | f | 43.70137 | 44.2712329 | 208 |
| 57 | x | gbm | n | w | f | 81.33699 | 81.3863014 | 18 |
| 58 | x | gbm | n | w | m | 48.61096 | 49.0657534 | 166 |
| 59 | x | gbm, r/r | n | w | f | 38.23014 | 40.1835616 | 713 |
| 60 | x | gbm | n | w | m | 78.61644 | 79.3863014 | 281 |
| 61 | x | gbm | n | w | f | 74.37534 | 74.9369863 | 205 |
| 62 | x | gbm, r/r | n | w | f | 72.97808 | 73.1835616 | 75 |
| 63 | x | gbm | n | w | f | 25.93973 | 35.4821918 | 3483 |
| 64 | x | gbm | n | w | f | 82.20274 | 82.7232877 | 190 |
| 65 | x | gbm | n | w | m | 72.67671 | 72.7753425 | 36 |
| 66 | x | gbm | n | w | m | 68.39904 | 69.8465753 | 532 |
| 67 | x | gbm | n | w | m | 72.6274 | 73.230137 | 220 |
| 68 | x | gbm | n | w | f | 75.72055 | 76.8931507 | 428 |
| 69 | x | meningioma | n | w | f | 32.87123 | 33.8493151 | 357 |
| 70 | x | gbm, r/r | n | w | m | 60.43014 | 60.6191781 | 69 |
| 71 | x | gbm, r/r | n | w | f | 63.53151 | 63.9726027 | 161 |
| 72 | x | gbm | n | w | f | 69.4274 | 70.1315068 | 257 |
| 73 | x | gbm | n | w-pv | m | 60.32603 | 61.7424658 | 517 |
| 74 | x | gbm, r/r | n | w | m | 45.72055 | 46.4246575 | 257 |
| 75 | x | gbm | n | w | m | 61.04658 | 61.5041096 | 167 |
| 76 | x | gbm, r/r | n | w | f | 58.25753 | 58.9753425 | 262 |
| 77 | x | gbm | n | w | m | 77.70685 | 78.260274 | 202 |
| 78 | x | gbm, giant | n | w | f | 62.86575 | 63.1150685 | 91 |
| 79 | x | gbm from gr2 | n | w | f | 82.0411 | 83.6164384 | 575 |
| 80 | x | gbm | n | w | m | 58.03836 | 58.8219178 | 286 |
| 81 | x | gbm | n | w | f | 55.89863 | 57.2547945 | 495 |
| 82 | x | gbm | n | w | m | 65.11507 | 67.0328767 | 700 |
| 83 | x | gbm | n | ns | m | 80.86575 | 81.2739726 | 149 |
| 84 | x | gbm | n | w | m | 54.41096 | 54.6657534 | 93 |
| 85 | x | gbm, sm cell | n | w | m | 61.66301 | 63.909589 | 820 |
| 86 | x | gbm | n | ns | f | 60.57534 | 60.6164384 | 15 |
| 87 | x | gbm | n | aa | f | 44.08219 | 52.2767123 | 2991 |
| 88 | x | gbm | n | w | f | 51.92055 | 54.4958904 | 940 |
| 89 | x | gbm, r/r | n | w | m | 61.83562 | 66.7479452 | 1793 |
| 90 | x | gbm | n | w | m | 58.80822 | 61.0821918 | 830 |
| 91 | x | gbm, r/r | n | w | f | 60.43288 | 61.8465753 | 516 |
| 92 | x | gbm | n | w | m | 71.24384 | 71.6328767 | 142 |
| 93 | x | gbm | n | w | m | 65.62466 | 66.5260274 | 329 |
| 94 | x | gbm | n | w | f | 56.66301 | 58.9506849 | 835 |
| 95 | x | gbm | n | w | m | 55.95342 | 57.7863014 | 669 |
| 96 | x | gbm | n | w | m | 84.60274 | 85.3589041 | 276 |

TABLE 10-continued

| | | | | | | (Glioblastoma) | | |
|---|---|---|---|---|---|---|---|---|
| case# | area | dx | MF | race | sex | age at dx yr | age at death | survival days |
| 97 | x | gliosarc | n | w | f | 71.88493 | 72.8849315 | 365 |
| 98 | temp, r | gbm | n | w | m | 28.32329 | 34.2493151 | 2163 |
| 99 | x | gbm | n | w | m | 73.0411 | 73.690411 | 237 |
| 100 | x | gbm | n | w | f | 73.74247 | 73.9013699 | 58 |
| 101 | x | gbm | n | w | m | 80.53425 | 81.0273973 | 180 |
| 102 | x | gbm | n | w | m | 84.04384 | 84.139726 | 35 |
| 103 | x | gbm | n | w | f | 61.06575 | 66.6931507 | 2054 |
| 104 | x | gbm | n | w | m | 72.20822 | 72.2712329 | 23 |
| 105 | x | gbm | n | w | m | 51.73425 | 57.4739726 | 2095 |
| 106 | x | gbm | n | w | m | 58.34521 | 63.8931507 | 2025 |
| 107 | x | gbm, r/r | n | w | m | 44.24658 | 44.8520548 | 221 |
| 108 | x | gbm | n | w | f | 53.74795 | 55.0054795 | 459 |
| 109 | x | gbm | n | w | m | 75.04658 | 75.2136986 | 61 |
| 110 | x | gbm | n | w | f | 38.71507 | 40.4273973 | 625 |
| 111 | x | gbm | n | w | m | 49.85205 | 51.9561644 | 768 |
| 112 | par, l | aa | n | w | f | 60.80274 | 61.7452055 | 344 |
| 113 | temp, l | gbm | n | w | m | 61.18082 | 62.0931507 | 333 |
| 114 | temp, l | gbm | n | w | m | 60.32603 | 63.7972603 | 1267 |
| 115 | x | gbm, r/r | n | w | m | 74.30685 | 74.3863014 | 29 |
| 116 | front, l | gbm | n | w | m | 89.71507 | 89.8027397 | 32 |
| 117 | temp, l | gliosarc | n | w | m | 80.50959 | 80.7479452 | 87 |
| 118 | par, r | gbm | n | w | f | 82.38356 | 82.4849315 | 37 |
| 119 | par, l | gbm | n | w | f | 58.62466 | 59.0246575 | 146 |
| 120 | temp, l | gbm | n | w | m | 60.86027 | 63.2520548 | 873 |
| 121 | x | gbm | n | w | f | 79.13151 | 80.0109589 | 321 |
| 122 | temp, r | gbm | n | ns | f | 54.4411 | 56.2410959 | 657 |
| 123 | fr, r | gbm | n | ns | f | 75.58356 | 76.1342466 | 201 |
| 124 | x | gbm | n | w | f | 43.46027 | 45.8054795 | 856 |
| 125 | x | gbm | n | w | m | 59.30959 | 59.3369863 | 10 |
| 126 | fr, r | gbm | n | w | m | 56.84932 | 59.1726027 | 848 |
| 127 | fr, r | gbm | n | w | m | 66.87671 | 67.0739726 | 72 |
| 128 | fr, l | gbm | n | w | m | 56.83562 | 58.4986301 | 607 |
| 129 | x | gbm | n | w | f | 72.16438 | 73.4849315 | 482 |
| 130 | par-occ, r | gbm | n | w | f | 50.42466 | 52.6739726 | 821 |
| 131 | occ, l | gbm | n | w | f | 81.90137 | 82.2356164 | 122 |
| 132 | x | gbm | n | w | f | 64.53151 | 66.7342466 | 804 |
| 133 | x | gbm | n | w | m | 58.28767 | 60.4547945 | 791 |
| 134 | x | gbm | n | w | f | 59.30411 | 61 | 619 |
| 135 | fr, l | gbm | n | w | f | 74.08219 | 75.2054795 | 410 |
| 136 | fr, l | gbm | n | w | m | 57.97534 | 60.1232877 | 784 |
| 137 | par, r | gbm | n | w | f | 72.99726 | 73.7917808 | 290 |
| 138 | fr, l | gbm | n | ns | f | 72.07671 | 72.6027397 | 192 |
| 139 | par, r | gbm | n | w | f | 74.63288 | 74.8520548 | 80 |
| 140 | x | gbm | n | w | m | 87.73973 | 88.7890411 | 383 |
| 141 | fr, r | gbm | n | w | f | 43.22466 | 43.909589 | 250 |
| 142 | occ, l | gbm | n | w | m | 42.72877 | 43.4438356 | 261 |
| 143 | temp, r | gbm | n | w | m | 56.28493 | 57.8958904 | 588 |
| 144 | fr, l | gbm | n | aa | m | 47.24932 | 49.0082192 | 642 |
| 145 | temp-par, l | gbm | n | w | m | 45.39726 | 47.2520548 | 677 |
| 146 | temp, l | gbm | n | w | m | 42.63562 | 44.5260274 | 690 |
| 147 | temp, r | gbm | n | w | f | 53.13699 | 56.1671233 | 1106 |
| 148 | par, r | gbm | n | w | f | 44.57534 | 52.260274 | 2805 |
| 149 | temp, l | gliosarc | n | w | m | 80.50959 | 82.7479452 | 87 |
| 150 | par, r | gbm | n | w | f | 82.38356 | 84.4849315 | 135 |
| 151 | par, l | gbm | n | w | f | 58.62466 | 49.0246575 | 126 |
| 152 | temp, l | gbm | n | w | m | 60.86027 | 63.2520548 | 873 |
| 153 | x | gbm | n | w | f | 79.13151 | 85.0109589 | 221 |
| 154 | temp, r | gbm | n | ns | f | 54.4411 | 55.2410959 | 647 |
| 155 | fr, r | gbm | n | ns | f | 75.58356 | 76.4542466 | 231 |
| 156 | x | gbm | n | w | f | 72.16438 | 53.4849315 | 382 |

N = negative
P = positive
P2 = positive in nested RT-PCR

TABLE 11

Metastasis of SCID mice xenografted with cancer cells expressing MAN2A1-FER

| Cells | Treatment | Mouse number | Metastasis |
|---|---|---|---|
| PMF | Tet+ | #1 | Lung |
| | | #2 | Not detected |
| | | #3 | Not detected |
| | | #4 | Not detected |
| | | #5 | Not detected |
| | | #6 | Liver |
| | Tet− | #1 | Not detected |
| | | #2 | Lung |
| | | #3 | Not detected |
| | | #4 | Not detected |
| | | #5 | Not detected |
| | | #6 | Not detected |
| DMF | Tet+ | #1 | Not detected |
| | | #2 | Lung |
| | | #3 | Not detected |
| | | #4 | Lung |
| | | #5 | Not detected |
| | | #6 | Liver |
| | Tet− | #1 | Not detected |
| | | #2 | Not detected |
| | | #3 | Not detected |
| | | #4 | Lung |
| | | #5 | Not detected |
| | | #6 | Not detected |
| HEPMF | Tet+ | #1 | Lung |
| | | #2 | Lung |
| | | #3 | Not detected |
| | | #4 | Liver |
| | | #5 | Not detected |
| | Tet− | #1 | Not detected |
| | | #2 | Not detected |
| | | #3 | Not detected |
| | | #4 | Lung |
| | | #5 | Not detected |
| | | #6 | Not detected |
| GMF | Tet+ | #1 | Liver |
| | | #2 | Not detected |
| | | #3 | Not detected |
| | | #4 | Lung |
| | | #5 | Lung |
| | | #6 | Not detected |
| | Tet− | #1 | Not detected |
| | | #2 | Not detected |
| | | #3 | Not detected |
| | | #4 | Not detected |
| | | #5 | Not detected |
| | | #6 | Not detected |
| HUH7 | WT | #1 | Liver |
| | | #2 | Liver |
| | | #3 | Liver |
| | | #4 | Lung |
| | | #5 | Liver |
| | | #6 | Lung |
| | KO | #1 | Not detected |
| | | #2 | Not detected |
| | | #3 | Not detected |
| | | #4 | Not detected |
| | | #5 | Not detected |
| | | #6 | Not detected |
| HMF | Tet+ | #1 | Not detected |
| | | #2 | Lung |
| | | #3 | Not detected |
| | | #4 | Not detected |
| | | #5 | Not detected |
| | | #6 | Liver |
| | Tet− | #1 | Not detected |
| | | #2 | Not detected |
| | | #3 | Not detected |
| | | #4 | Not detected |
| | | #5 | Not detected |
| | | #6 | Not detected |

---

What is claimed is:

1. A method of treating a subject in need thereof, wherein the method comprises performing one or more of cryotherapy, radiation therapy, chemotherapy, hormone therapy, high-intensity focused ultrasound and frequent monitoring to achieve an anti-neoplastic effect in the subject, wherein the subject does not have prostate cancer; and
wherein the subject has at least one condition selected from the group consisting of a premalignant condition, a neoplastic condition, a cancer, and combination thereof; and wherein the subject has a MAN2A1-FER fusion gene.

2. The method of claim 1, wherein the subject has a pre-malignant or neoplastic condition.

3. The method of claim 1, wherein the subject has a cancer.

4. The method of claim 3, wherein the cancer is breast cancer, liver cancer, lung cancer, non-small cell lung cancer, cervical cancer, endometrial cancer, pancreatic cancer, ovarian cancer, gastric cancer, thyroid cancer, glioblastoma multiforme, colorectal cancer, sarcoma, diffuse large B-cell lymphoma, or esophageal adenocarcinoma.

5. The method of claim 3, wherein the cancer is not lung adenocarcinoma, glioblastoma multiforme or hepatocellular carcinoma.

6. The method of claim 1, wherein the MAN2A1-FER fusion gene is detected by FISH analysis or by reverse transcription polymerase chain reaction.

7. A method of treating a subject in need thereof, comprising administering a therapeutic effective amount of an inhibitor specific for a MAN2A1-FER fusion genes contained within the one or more cells, or a therapeutic effective amount of an agent that inhibits the product of the MAN2A1-FER fusion genes contained within the one or more cells, or a therapeutic effective amount of an siRNA targeting the MAN2A1-FER fusion genes contained within the one or more cells,
wherein the subject has at least one condition selected from the group consisting of a premalignant condition, a neoplastic condition, a cancer, and combination thereof;
wherein the subject does not have prostate cancer.

8. The method of claim 7, wherein the subject has a cancer.

9. The method of claim 8, wherein the cancer is breast cancer, liver cancer, lung cancer, non-small cell lung cancer, cervical cancer, endometrial cancer, pancreatic cancer, ovarian cancer, gastric cancer, thyroid cancer, glioblastoma multiforme, colorectal cancer, sarcoma, diffuse large B-cell lymphoma, or esophageal adenocarcinoma.

10. The method of claim 8, wherein the cancer is not lung adenocarcinoma, glioblastoma multiforme or hepatocellular carcinoma.

11. The method of claim 7, wherein the subject has a pre-malignant or neoplastic condition.

12. The method of claim 7, wherein the MAN2A1-FER fusion genes is detected by FISH analysis or by reverse transcription polymerase chain reaction.

13. A method of treating a subject comprising administering a therapeutic effective amount of one or more inhibitors specific for the MAN2A1-FER fusion gene contained within the cell, wherein the subject does not have prostate cancer; and wherein a MAN2A1-FER gene is present in a cell of the subject.

14. The method of claim 13, wherein the subject has a pre-malignant or neoplastic condition.

15. The method of claim 13, wherein the one or more inhibitors includes a combination of canertinib and crizotinib.

16. A method of treating a subject, comprising (i) determining the presence of a MAN2A1-FER fusion gene in a cell of the subject; and (ii) where if the MAN2A1-FER fusion gene is present in the cell, then administering a therapeutic effective amount of a FER inhibitor, or an EGFR inhibitor, or a FER inhibitor and an EGFR inhibitor, wherein the subject does not have prostate cancer.

17. The method of claim 16, wherein the EGFR inhibitor is canertinib, and the FER inhibitor is crizotinib.

18. The method of claim 16, wherein the subject has a cancer, and wherein the cancer is breast cancer, liver cancer, lung cancer, non-small cell lung cancer, cervical cancer, endometrial cancer, pancreatic cancer, ovarian cancer, gastric cancer, thyroid cancer, glioblastoma multiforme, colorectal cancer, sarcoma, diffuse large B-cell lymphoma, or esophageal adenocarcinoma.

19. The method of claim 16, wherein the subject has a cancer, and wherein the cancer is not lung adenocarcinoma, glioblastoma multiforme or hepatocellular carcinoma.

20. The method of claim 16, wherein the MAN2A1-FER fusion gene is detected by FISH analysis or by reverse transcription polymerase chain reaction.

21. A method of determining a treatment for a subject having one or more cells that contains one or more fusion genes, comprising
i) providing a sample from the subject;
ii) determining whether one or more cells of the subject contains a MAN2A1-FER fusion gene; and
iii) if the one or more fusion genes are_detected in the one or more cells of the subject, then instructing the administration of a therapeutically effective amount of one or more inhibitors specific to the MAN2A1-FER fusion gene, wherein the subject does not have prostate cancer.

* * * * *

SEQUENCE LISTING

<160> NUMBER OF SEQ ID NOS: 145

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcaaatacta tttcagaaac agcctatgag ggaaattttg gtgaagtata taagggcaca      60

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
cagccuauga gggaaauuuu gguga                                           25

```
<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucaccaaaau uucccucaua ggcuguu                                         27

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccactacca tgccctcttc acaggtgtca tggagaaact ccagctgggc ccagaga       57

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ugcccucuuc acagguguca uggag                                          25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuccaugaca ccugugaaga gggcaug                                        27

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtcagaatc caagtcaagt caggattcct tgttctggga atgtcagtgg aatctgctcc   60
tgc                                                                  63

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 8
gucaggauuc cuuguucugg gaatg                                            25

<210> SEQ ID NO 9
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cauucccaga acaaggaauc cugacuu                                          27

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttttaagact caccaagggc aaataagaag ccaactccaa caggtggaag agtacca         57

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gacucaccaa gggcaaauaa gaagc                                            25

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gcuucuuauu ugcccuuggu gagucuu                                          27

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgtcacagtt actagatata atgaaaatac ctggagtaga acagaaaaat tattatgtct      60
```

```
<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
augaaaauac cuggaguaga acaga                                           25

<210> SEQ ID NO 15
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ucuguucuac uccagguauu uucauua                                         27

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aactacctgc actttgggga gcctaagtcc tggacagtaa gcaagcctgg atctgagaga     60

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gagccuaagu ccuggacagu aagca                                           25

<210> SEQ ID NO 18
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugcuuacugu ccaggacuua ggcuccc                                         27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
agcatctgga gttccgcctg ccggtggtat ttttgaatat gtggaatctg gcccaatggg    60
agctg                                                                65

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
ccgccugccg gugguauuuu ugaat                                          25

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auucaaaaau accaccggca ggcggaa                                        27

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgcttggat gagaagcagt gtaagcagtg tgcaaacaag gtgactggaa gcacctgctc    60
aatggctg                                                             68

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
acaaggugac uggaagcacc ugctc                                          25

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gagcaggugc uuccagucac cuuguuu                                        27

```
<210> SEQ ID NO 25
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagccaaccg atactttct ccaaattta agacacagca ggatgccaat gcctcttccc    60
tcttagac                                                           68

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cuccaaauuu uaagacacag cagga                                        25

<210> SEQ ID NO 27
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uccugcugug ucuuaaaauu uggagaa                                      27

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcaagatcat tgctcctcct gagc                                         24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgctgtcacc ttcaccgttc cagt                                         24

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 30
tcccattgac acctttccca c					21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaggcttcc aggtacaaca g					21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcccagttgc agaaaggaat g					21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttgattttc agtggcaggc c					21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gactacgtct catgcctttc c					21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttctcatcag gctggtcctt c					21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gatgtggtgg aatatgccaa gg                                        22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aaatccatgt gctgtggcac c                                         21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgcaatgagg aagaagggaa c                                         21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cataaatctg gaatagggct cag                                       23

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
taaaagctaa agttaaatac ctgtttgaaa atggta                         36

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcactcataa agaagagctt gaatttggaa atgac                          35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 42
atagctttga taaactgctc tccagaatgt tg                                    32

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccaactcac ccagattggc tgcaatgccg tcag                                  34

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgccaatact agtgtggctt ttcatggcct gccac                                 35

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcagaaacag cctatgaggg aaatttggt ga                                     32

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactcaccaa gggcaaataa gaagccaact ccaacag                               37

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taagcagtgt gcaaacaagg tgactggaag cacctgctca at                         42

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 48
gcatctggag ttccgcctgc cggtggtatt tttgaatatg          40

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccagtcagtc aggattcctt gttctgggaa tgtcagtgg          39

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gttactagat ataatgaaaa tacctggagt agaacagaaa          40

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccactaccat gccctcttca caggtgtcat ggagaaactc ca          42

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aactacctgc actttgggga gcctaagtcc tggacagtaa gcaagcc          47

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatgtttaaa tttggaacgt ggactttggg gcaggt          36

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
taataatcaa cctagctacc ctaaactcct                                    30

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctcattatg ttgccgaagg ggatatcacc acca                               34

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttttctccaa attttaagag acagcaggat gccaa                              35

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaatttggaa cgtggacttt ggg                                           23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagaccatct tactggaagt tcc                                           23

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggtactctt ccacctgttg g                                             21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 60
ttggcatgat agaccagtcc c                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagcaccaag ggaatgtgta g                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgctgtcgt gtacccttaa c                                              21

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggtaagggta gtattgggta gc                                             22

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccagggctgg aattactatg g                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aagcaccagt ctgcacaatc c                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 66
ttgatgtctg ctcccatcag g                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgatatcgtg gccagctaac c                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aacacgccct acctgtactt c                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgagcaaag acagcaacac c                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggaagttca agtcagcgca g                                              21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gctgtctttg tgtgcaaact cc                                             22

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 72
gtgactgctt ggatgagaag c                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccagcatgca gcttttctga g                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agtaggcgcg agctaagcag g                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggacagtct gaatcatgtc c                                              21

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aacctgagtc tgccaaggac tagc                                           24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ttccacacac cactggccat cttc                                           24

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 78
acagaagtct gggatgtgga                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcccaaaaag acagacagaa                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gatcccaagc tcttcctctt                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgtttgtgt gtgcatctgt                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gggtgatttt cctctttggt                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgattccaat catagccaca                    20

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgtcatagtt tagaacgaac taacg                                    25

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ctgaggtatc aaaaactcag agg                                      23

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gtgggctgaa aagctcccga ttat                                     24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
attcaaaggg tatctgggct ctgg                                     24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
actggcacag aacaggcact tagg                                     24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggaggaactg ggaaccacac aggt                                     24

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 90
ccctagtgga tgataagaat aatcagtatg                                          30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggacagatga taaatacata ggatggatgg                                          30

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tggaagttca agtcagcgca g                                                   21

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gaagttttat cctttaatgt gccc                                                24

<210> SEQ ID NO 94
<211> LENGTH: 9
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94 tcagaaaca                                                                  9

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
gcctatgagg gaaatt                                                         16

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 96
gcatgggtca aaggattcc t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtgctcgatg gggtacttca g                                             21

<210> SEQ ID NO 98
<211> LENGTH: 9
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98 cgacgaggc                                                            9

<210> SEQ ID NO 99
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ccagagcaag ag                                                       12

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctgcttcagg aaaacctgtg g                                             21

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tacatgtttt aacagcaaca gaag                                          24

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 102
tggaagttca agtcagcgca g                                              21

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaagttttat cctttaatgt gccc                                           24

<210> SEQ ID NO 104
<211> LENGTH: 9
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104 tcagaaaca                                                             9

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gcctatgagg gaaatt                                                    16

<210> SEQ ID NO 106
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gactcagatg cttaaggaga ctaggtgcgg agcaag                              36

<210> SEQ ID NO 107
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gtactcacgt tctagatgtg agttttctct tgatgatagt g                        41

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 108
gactcagatg ggatccatga agttaagccg ccagttc                                37

<210> SEQ ID NO 109
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtactcacgt gcggccgctg tgagttttct cttgatgata gtg                         43

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gactcagatg gtcgacgaga ctaggtgcgg agcaag                                 36

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gtactcacgt gcggccgctg tgagttttct cttgatgata gtg                         43

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gcaacatgta aagaagatct tcctcagg                                          28

<210> SEQ ID NO 113
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aacagcaaca gaagttttat cctttaatg                                         29

<210> SEQ ID NO 114
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gactcagatg gctagcatgc gaccctccgg gacggc        36

<210> SEQ ID NO 115
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gtactcacgt aagctttcat cccagtggcg atggacg        37

<210> SEQ ID NO 116
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gactcagatg aagctttgac tccgtccagt attgatc        37

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gtactcacgt ttctagacat cccagtggcg atggacg        37

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Glu Val Val Leu Gly Asn Leu Glu Ile Thr Tyr Val Gln Arg Asn Tyr
1               5                   10                  15

Asp Leu Ser Phe Leu
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Leu Glu Ile Thr Tyr Val Gln Arg Asn Tyr Asp Leu Ser Phe Leu
1               5                   10                  15

Lys Thr Ile Gln Glu
            20

```
<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Phe Leu Lys Thr Ile Gln Glu Val Ala Gly Tyr Val Leu Ile Ala Leu
1               5                   10                  15

Asn Thr Val Glu Arg
            20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Glu Asn Leu Gln Ile Ile Arg Gly Asn Met Tyr Tyr Glu Asn Ser Tyr
1               5                   10                  15

Ala Leu Ala Val Leu
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asn Leu Gln Ile Ile Arg Gly Asn Met Tyr Tyr Glu Asn Ser Tyr Ala
1               5                   10                  15

Leu Ala Val Leu Ser
            20

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Arg Gly Asn Met Tyr Tyr Glu Asn Ser Tyr Ala Leu Ala Val Leu
1               5                   10                  15

Ser Asn Tyr Asp Ala
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 124

Asn Ser Tyr Ala Leu Ala Val Leu Ser Asn Tyr Asp Ala Asn Lys Thr
1               5                   10                  15

Gly Leu Lys Glu Leu
            20

<210> SEQ ID NO 125
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Lys Asp Thr Cys Pro Pro Leu Met Leu Tyr Asn Pro Thr Thr Tyr
1               5                   10                  15

Gln Met Asp Val Asn
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Pro Leu Met Leu Tyr Asn Pro Thr Thr Tyr Gln Met Asp Val Asn
1               5                   10                  15

Pro Glu Gly Lys Tyr
            20

<210> SEQ ID NO 127
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Met Asp Val Asn Pro Glu Gly Lys Tyr Ser Phe Gly Ala Thr Cys
1               5                   10                  15

Val Lys Lys

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Thr Cys Val Lys Lys Cys Pro Arg Asn Tyr Val Val Thr Asp His
1               5                   10                  15

Gly Ser Cys Val Arg
            20
```

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Cys Val Arg Ala Cys Gly Ala Asp Ser Tyr Glu Met Glu Glu Asp
1               5                   10                  15

Gly Val Arg Lys Cys
            20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val Ile Ile Ser Gly Asn Lys Asn Leu Cys Tyr Ala Asn Thr Ile Asn
1               5                   10                  15

Trp Lys Lys Leu Phe
            20

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Pro Asp Asn Cys Ile Gln Cys Ala His Tyr Ile Asp Gly Pro His
1               5                   10                  15

Cys Val Lys Thr Cys
            20

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Gly Glu Asn Asn Thr Leu Val Trp Lys Tyr Ala Asp Ala Gly His
1               5                   10                  15

Val Cys His Leu Cys
            20

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val Cys His Leu Cys His Pro Asn Cys Thr Tyr Gly Cys Thr Gly Pro
1               5                   10                  15

Gly Leu Glu Gly Cys
            20

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gactcagatg gcggccgcga acatcagaac tgggagagg                              39

<210> SEQ ID NO 135
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gtactcacgt aagcttcagg agaatcactt gaacccg                                37

<210> SEQ ID NO 136
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
taatgttggt tttaccaaaa atataaatgg tttgcctctc agtagataac atttatcttt       60
aataaattcc cttccctatc ttttaaagat ctcttttcga gcacatat                   108

<210> SEQ ID NO 137
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
taatatgtgc tcgaaaagag atctttaaaa gatagggaag ggaatttatt aaagataaat       60
gttatctact gagaggcaaa ccatttatat ttttggtaaa accaacat                   108

<210> SEQ ID NO 138
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gactcagatg gaattcaagg tggaacacag aaggagg                                37

-continued

<210> SEQ ID NO 139
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gtactcacgt gaattcgatt actttaaata actcacttgg cttcttgcag aggtagagct      60
gagagaag                                                              68

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
atagctagaa ggtggatcac                                                 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tagcattaag ggcccccctaa                                                20

<210> SEQ ID NO 142
<211> LENGTH: 28
<212> TYPE: DNA
<213> ORGANISM: Homo sapiens

<400> SEQUENCE: 142
ccaccttcta gctattgagt agcattaa                                        28

<210> SEQ ID NO 143
<211> LENGTH: 26
<212> TYPE: DNA
<213> ORGANISM: Homo sapiens

<400> SEQUENCE: 143
tccaccttct agctattgag tagcat                                          26

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Phe Leu Lys Thr Ile Gln Glu Val Ala Gly Tyr Val Leu Ile Ala Leu
1               5                   10                  15

Asn Thr Val Glu Arg
            20

-continued

```
<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Phe Leu Lys Thr Ile Gln Glu Val Ala Gly Ala Val Leu Ile Ala Leu
1               5                   10                  15

Asn Thr Val Glu Arg
            20
```